(12) United States Patent
Almirante et al.

(10) Patent No.: US 11,980,618 B2
(45) Date of Patent: May 14, 2024

(54) NITRIC OXIDE RELEASING PHOSPHODIESTERASE TYPE 5 INHIBITOR

(71) Applicant: NICOX S.A., Valbonne (FR)

(72) Inventors: Nicoletta Almirante, Milan (IT);
Stefania Brambilla, Merone (IT);
Laura Storoni, Cesano Maderno (IT);
Francesco Impagnatiello, Milan (IT);
Elena Bastia, Milan (IT)

(73) Assignee: NICOX S.A., Valbonne (FR)

( * ) Notice: Subject to any disclaimer, the term of this patent is extended or adjusted under 35 U.S.C. 154(b) by 404 days.

(21) Appl. No.: 17/265,134

(22) PCT Filed: Jul. 31, 2019

(86) PCT No.: PCT/EP2019/070597
§ 371 (c)(1),
(2) Date: Feb. 1, 2021

(87) PCT Pub. No.: WO2020/030489
PCT Pub. Date: Feb. 13, 2020

(65) Prior Publication Data
US 2021/0322413 A1    Oct. 21, 2021

(30) Foreign Application Priority Data

Aug. 6, 2018 (EP) .................................. 18187482
Dec. 4, 2018 (EP) .................................. 18210147

(51) Int. Cl.
| | | |
|---|---|---|
| *A61K 31/506* | (2006.01) |
| *A61K 31/197* | (2006.01) |
| *A61K 31/519* | (2006.01) |
| *A61K 45/06* | (2006.01) |
| *A61P 27/06* | (2006.01) |
| *C07D 403/14* | (2006.01) |
| *C07D 487/04* | (2006.01) |

(52) U.S. Cl.
CPC .......... *A61K 31/506* (2013.01); *A61K 31/197* (2013.01); *A61K 31/519* (2013.01); *A61K 45/06* (2013.01); *A61P 27/06* (2018.01); *C07D 403/14* (2013.01); *C07D 487/04* (2013.01)

(58) Field of Classification Search
CPC .. A61K 31/506; A61K 31/197; A61K 31/519; A61K 45/06; A61K 9/0048; A61K 31/21; A61K 47/186; A61K 47/20; A61K 47/44; A61K 47/55; A61P 27/06; A61P 27/02; C07D 403/14; C07D 487/04
See application file for complete search history.

(56) References Cited

U.S. PATENT DOCUMENTS

| | | | |
|---|---|---|---|
| 2002/0168424 A1 | 11/2002 | Shahinpoor et al. | |
| 2008/0280914 A1* | 11/2008 | Serno ................. | A61K 31/4985 514/250 |
| 2018/0118677 A1 | 5/2018 | Almirante et al. | |

FOREIGN PATENT DOCUMENTS

| | | | |
|---|---|---|---|
| CN | 102498088 A | 6/2012 | |
| EP | 2826491 A1 | 1/2015 | |
| EP | 3088388 A1 | 11/2016 | |
| JP | 2011511022 A | 4/2011 | |
| JP | 2017534658 A | 11/2017 | |
| WO | WO2008075152 A1 * | 6/2008 | .......... C07D 249/08 |
| WO | WO2010096320 A2 * | 8/2010 | |
| WO | WO2011075655 A1 * | 6/2011 | .......... A61K 31/497 |
| WO | 2016155906 A1 | 10/2016 | |
| WO | 2016156104 A1 | 10/2016 | |
| WO | 2017085056 A1 | 5/2017 | |
| WO | 2018215433 A1 | 11/2018 | |

OTHER PUBLICATIONS

Haroldo A. Flores Toque, "Synthesis and Pharmacological Evaluation of Sildenafil Analogues for Treatment of Erectile Dysfunction", Journal of Medicinal Chemistry, vol. 5, No. 9, May 1, 2008, pp. 2807-2815.
International Search Report and Written Opinion issued in corresponding International Application No. PCT/EP2019/070597 dated Nov. 7, 2019.
Park et al., "Mirodenafil for the Treatment of Erectile Dysfunction: A Systematic Review of the Literature," World Journal of Men's Health, Apr. 25, 2014, vol. 32, No. 1, p. 18.

* cited by examiner

*Primary Examiner* — Joseph K McKane
*Assistant Examiner* — David M Shim
(74) *Attorney, Agent, or Firm* — ArentFox Schiff LLP

(57) ABSTRACT

The invention relates to nitric oxide releasing phosphodiesterase type 5 (PDE5) inhibitors of formula or a stereoisomer or a pharmaceutically acceptable salt thereof:

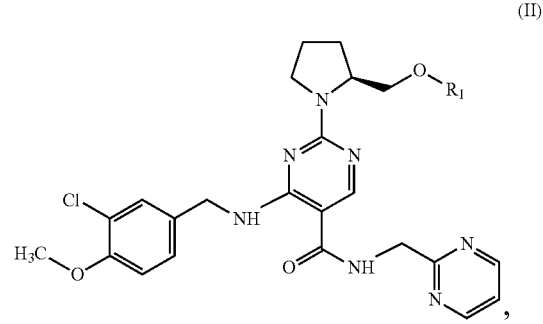

useful for the treatment of ocular condition associated with elevated intraocular pressure such as ocular hypertension, glaucoma or retinopathies.

14 Claims, No Drawings

NITRIC OXIDE RELEASING PHOSPHODIESTERASE TYPE 5 INHIBITOR

This application is a 35 U.S.C.§ 371 National Phase of PCT Application No. PCT/EP2019/070597, filed Jul. 31, 2019, which claims priority to European Application No. 18187482.7, filed Aug. 6, 2018, which claims priority to European Application No. 18210147.7, filed Dec. 4, 2018, the disclosures of which are hereby incorporated by reference herein.

The invention relates to nitric oxide releasing phosphodiesterase type 5 (PDE5) inhibitors. The invention further provides compositions and methods for treating an ocular condition associated with elevated intraocular pressure such as ocular hypertension and glaucoma.

Glaucoma is a progressive disease which leads to optic nerve damage and, ultimately, total loss of vision. Since there is a good correlation between intraocular pressure control and prevention/reduction of glaucomatous damage in POAG (Primary Open-Angle Glaucoma) patients, several therapeutic agents have been developed to treat ocular hypertension (Heijl A. et al. Arch Ophthalmol. 2002; 120: 1268-1279; Garway Heath et al. The Lancet 2015; 385: 1295-1304; Heijl A. The Lancet 2015; 385: 1264-1266).

It is known that elevated intraocular pressure can be at least partially controlled by administering drugs which either increase the outflow of aqueous humor from the eye, such as a prostaglandin analog (such as latanoprost or bimatoprost) or reduce the production of aqueous humor within the eye such as beta-blockers (such as timolol, betaxolol, levobunolol) and carbonic anhydrase inhibitors (such as acetazolamide, dorzolamide or brinzolamide).

Unfortunately, many of the drugs conventionally used to treat ocular hypertension have a variety of side effects. For example, prostaglandin therapy causes eye irritation and hyperemia of varying severity and duration. Beta-blockers show serious pulmonary side effects, depression, fatigue, confusion, impotence, hair loss, heart failure and bradycardia. The side effects associated with carbonic anhydrase inhibitors include fatigue, anorexia, depression, paresthesias and serum electrolyte abnormalities.

It is known that nitric oxide (NO) plays an important role in numerous physiological processes; in the eye specifically nitric oxide plays an important role in physiological intraocular pressure regulation by facilitating the trabecular meshwork and Schlemm's canal aqueous humor outflow (Cavet et al., Invest Ophthalmol Vis Sci. 2014, 5005-5015).

Several studies have demonstrated that NO donors decrease intraocular pressure by increasing trabecular meshwork and Schlemm's canal aqueous humor outflow.

At cellular level, nitric oxide binds to the soluble guanylate cyclase enzyme (sGC) and increases the production of cyclic guanosine monophosphate (cGMP) in the trabecular meshwork and in the Schlemm's canal tissues where it activates a series of mechanisms that facilitate conventional aqueous humor drainage to finally reduce intraocular pressure (Cavet et al., Invest Ophthalmol Vis Sci. 2014, 5005-5015).

For example U.S. Pat. No. 4,590,207 discloses ophthalmic solution containing isosorbide mononitrate as the active ingredient for treating and/or preventing ocular hypertension and glaucoma.

EP 2 993 172 B1 discloses nitric oxide releasing carnosine analogues for the use in the treatment and/or prophylaxis of glaucoma and ocular hypertension. Results of studies in animal models showed that the nitric oxide releasing carnosine analogues have a greater TOP-lowering effect than isosorbide mononitrate (5-ISMN) and that the TOP-lowering effect lasts up to about 2 hours after the topical administration.

WO 2014/063923 discloses nitric oxide donor compounds having a quinone based structure and their use in the treatment and/or prophylaxis of glaucoma and ocular hypertension.

In general, however, NO donor compounds that do not require activation by endogenous enzymes typically release nitric oxide rapidly; as a result of the rapid rate of nitric oxide release it is difficult to deliver sufficient quantities of NO to target tissues for extended periods of time.

One potential method to provide sustained efficacy would require that the NO donor compound is administered multiple times; however, this method of treatment exposes the patients to potentially higher side effect liability compared to single ocular dosing schedule. An excess of NO may elicit unwanted effects including oxidative stress and inflammatory markers biosynthesis (Colasanti & Suzuki, Trends Pharmacol Sci. 2000 21:249-252).

Another potential method to provide sustained activity over time is by reducing the degradation of cyclic guanosine monophosphate (cGMP) with a phosphodiesterase type 5 (PDE5) inhibitor.

The prior art suggests the use of a combination of a cyclic phosphodiesterase type 5 (PDE5) inhibitor and a nitric oxide (NO) donor for treating glaucoma or ocular hypertension; for example US 2002/0168424 discloses a topical drug for the treatment of glaucoma which comprises a mixture of a nitric oxide (NO) donor such as the nitrovasodilators minoxidil, nitroglycerin, L-arginine, isosorbide dinitrate or nitroprusside, and a phosphodiesterase type 5 (PDE5) inhibitor such as sildenafil citrate. This combination increases blood circulation to the optic nerve and has ocular hypotensive activity.

US 2002/0168424 does not disclose any experimental data related to the intraocular pressure lowering activity of the combinations and it does not suggest the effective doses of individual compounds used.

WO 2017/085056 discloses dual-pharmacology NO-releasing PDE5 inhibitors that are useful in the treatment of a variety of diseases where a disturbed cGMP balance occurs and/or PDE inhibition is thought to be beneficial, in particular for the treatment of diabetic patients; glaucoma is cited among a list of a number of preferred diseases.

In the dual-pharmacology NO-releasing PDE5 inhibitors the nitric oxide precursor is the nitrooxy group (ONO2) that is directly linked to a hydroxyl group (nitrate ester) of the PDE5 inhibitor molecules.

WO 2017/085056 discloses in vitro studies on rat aortic rings showing that the NO-releasing PDE5 inhibitors are able to activate soluble guanilate cyclase and have a higher PDE5 inhibitory activity than the known PDE5 inhibitor sildenafil. However, WO 2017/085056 does not disclose any experimental data related to the intraocular pressure lowering activity of NO-releasing PDE5 inhibitors.

Regarding phosphodiesterase type 5 (PDE5) inhibitors, also for this class of compounds the prior art suggests their potential therapeutic use in the treatment of glaucoma, for example:

U.S. Pat. No. 4,975,428 discloses the use of the PDE inhibitor bemarinone as agent for reducing intraocular pressure.

WO 01/60825 discloses a series of pyrazolo[4,3-d]pyrimidin-7-one derivatives as PDE5-inhibitors; glaucoma is mentioned as one of the potential therapeutic uses of these compounds.

EP 0 463 756 discloses a series of pyrazolo[4,3-d]pyrimidin-7-one derivatives as PDE5-inhibitors as antianginal agents; glaucoma is mentioned among a number of potential therapeutic uses of these compounds.

EP 1 074 258 discloses a method for treating glaucomatous optic neuropathy associated with chronic glaucoma, chronic (idiopathic) open-angle glaucoma and macular (dry) degeneration by systemic (oral or parenteral) administration of the PDE5-inhibitors and in particular sildenafil citrate.

There is, therefore, a continuing need for compounds for use in the therapeutic treatment of ocular diseases associated with elevated intraocular pressure.

The present invention provides novel nitric oxide releasing phosphodiesterase type 5 (NO-PDE5) inhibitors in which the nitric oxide precursor is a NO-releasing molecule (NO donor) linked to the PDE5 inhibitor through an enzymatic cleavable bond.

The nitric oxide releasing phosphodiesterase type 5 (NO-PDE5) inhibitors of the invention showed better efficacy and a longer duration compared to either the respective PDE5 or the NO-donor as evidenced by the greater $E_{max}$ (defined as maximum intraocular-lowering effect at a given dose) and $E_{480min}$ (IOP-lowering at the last time point analyzed) observed for NO-PDE5 and the NO-donor, respectively. Therefore the nitric oxide releasing phosphodiesterase type 5 (NO-PDE5) inhibitors of the invention are expected to provide an alternative treatment for various diseases and conditions in which the lowering of intraocular pressure is desired, for example glaucoma, ocular hypertension and other conditions associated with increased ocular pressure.

The invention provides compounds of formula (I) stereoisomers or salts thereof:

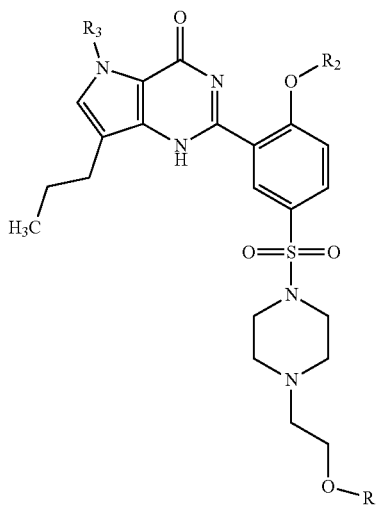
(I)

wherein:
$R_1$ is the residue of a nitric oxide releasing molecule having the following formula:

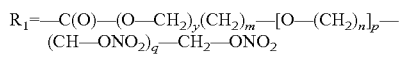

$R_1 = -C(O)-(O-CH_2)_y(CH_2)_m-[O-(CH_2)_n]_p-(CH-ONO_2)_q-CH_2-ONO_2$ wherein:
y is 1 or 0;
p is 1 or 0;
q is 1 or 0;
m is an integer ranging from 1 to 10; preferably m is from 1 to 6;

n is an integer ranging from 1 to 6; preferably n is 1 or 2;
$R_2$ is ethyl or n-propyl;
$R_3$ is methyl or ethyl;
with the proviso that when $R_2$ is ethyl, $R_3$ is methyl or when $R_2$ is n-propyl, $R_3$ is ethyl.

When y=0, $R_1$ is preferably selected from the group consisting of:

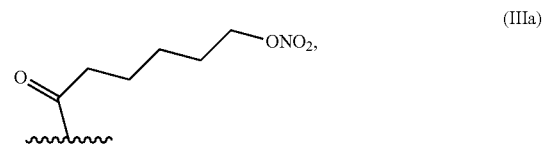
(IIIa)

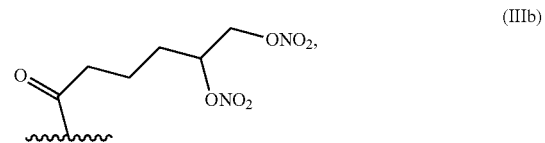
(IIIb)

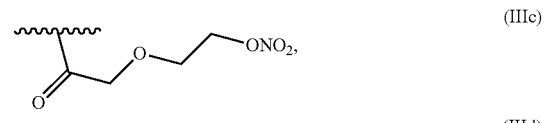
(IIIc)

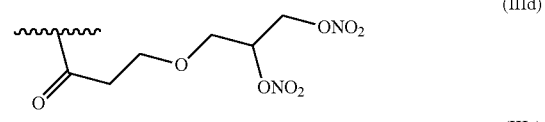
(IIId)

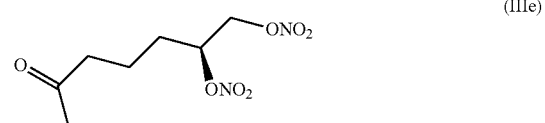
(IIIe)

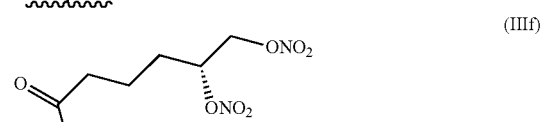
(IIIf)

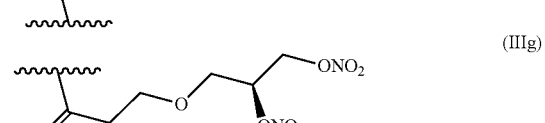
(IIIg)

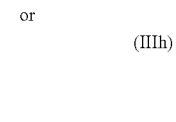
or

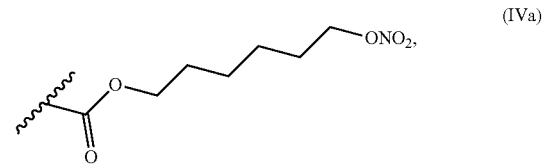
(IIIh)

When y=1, $R_1$ is preferably selected from the group consisting of:

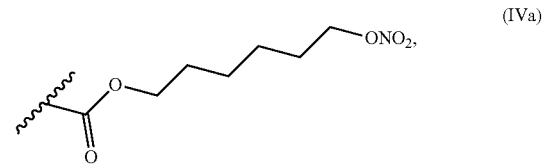
(IVa)

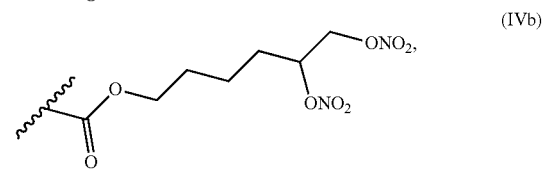
(IVb)

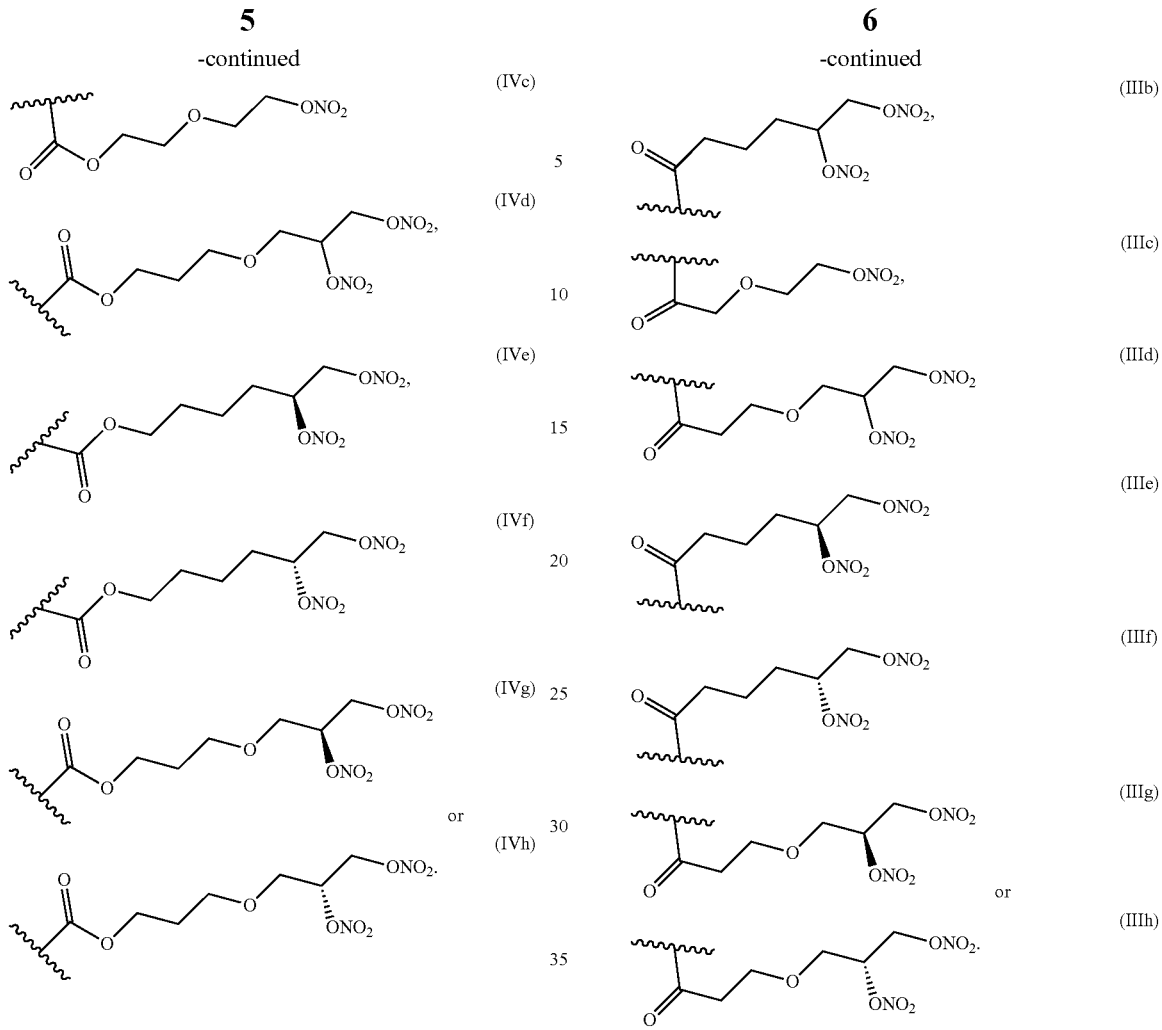

Another embodiment of the invention provides compounds of formula (I) stereoisomers or salts thereof as defined above wherein:

R₁ is the residue of a nitric oxide releasing molecule having the following formula:

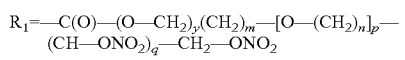

wherein:

y is 1 or 0;

p is 1 or 0;

q is 1 or 0;

m is an integer ranging from 1 to 10; preferably m is from 1 to 6;

n is an integer ranging from 1 to 6; preferably n is 1 or 2;

R₂ is n-propyl and R₃ is ethyl.

When y=0, R₁ is preferably selected from the group consisting of:

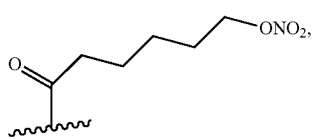

When y=1, R₁ is preferably selected from the group consisting of:

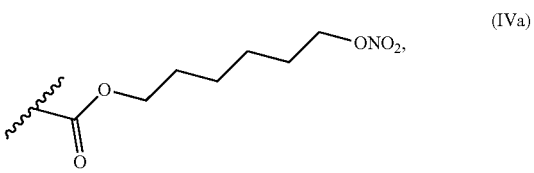

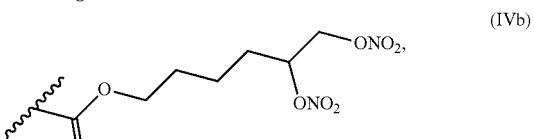

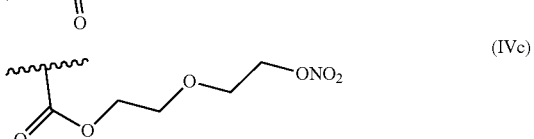

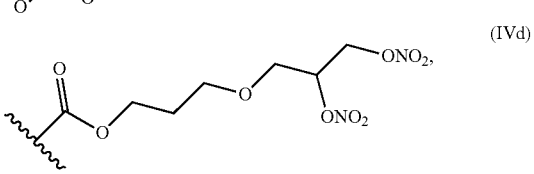

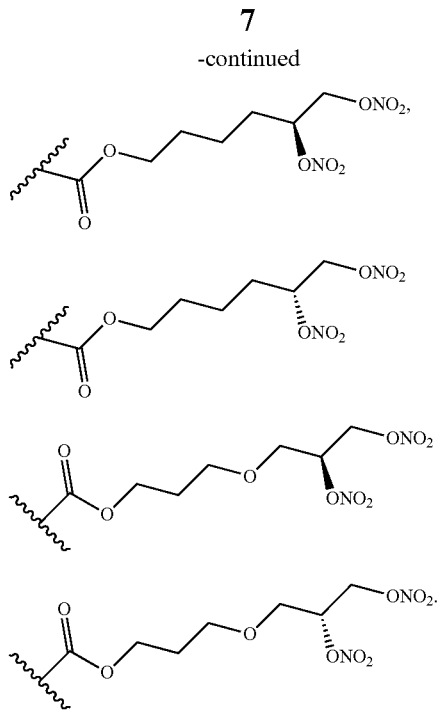

Another embodiment of the invention provides compounds of formula (I) stereoisomers or salts thereof as defined above wherein:

$R_2$ is n-propyl and $R_3$ is ethyl;

$R_1$ is the residue of a nitric oxide releasing molecule having the following formula:

$$R_1 = -C(O) - (O - CH_2)_y (CH_2)_m - [O - (CH_2)_n]_p - (CH - ONO_2)_q - CH_2 - ONO_2$$

y=0 and $R_1$ is selected from the group consisting of:

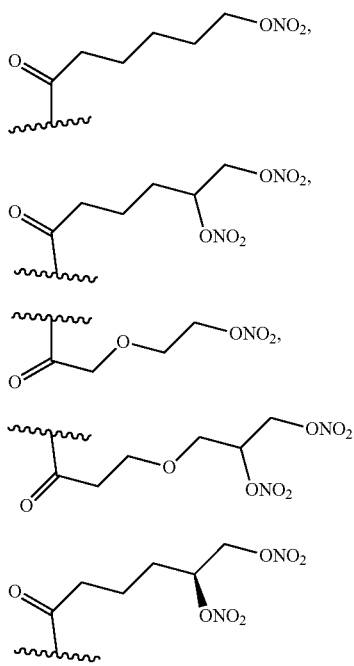

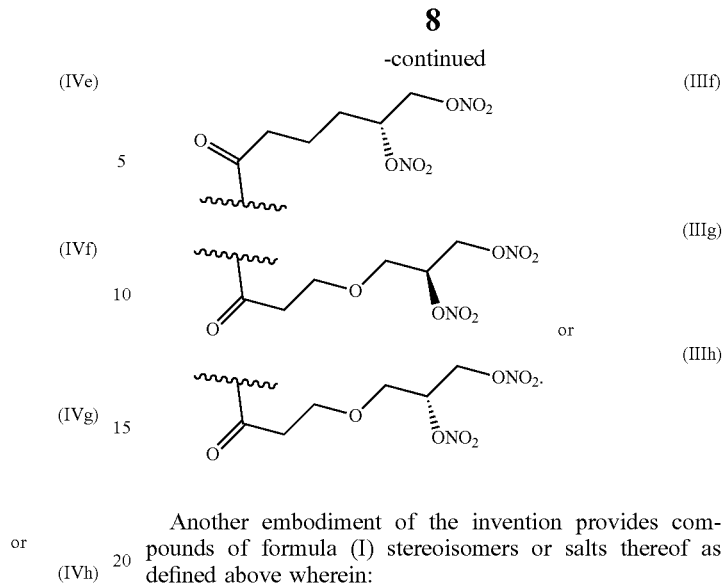

Another embodiment of the invention provides compounds of formula (I) stereoisomers or salts thereof as defined above wherein:

$R_2$ is n-propyl and $R_3$ is ethyl;

$R_1$ is the residue of a nitric oxide releasing molecule having the following formula:

$$R_1 = -C(O) - (O - CH_2)_y (CH_2)_m - [O - (CH_2)_n]_p - (CH - ONO_2)_q - CH_2 - ONO_2$$

y=1 and $R_1$ is selected from the group consisting of:

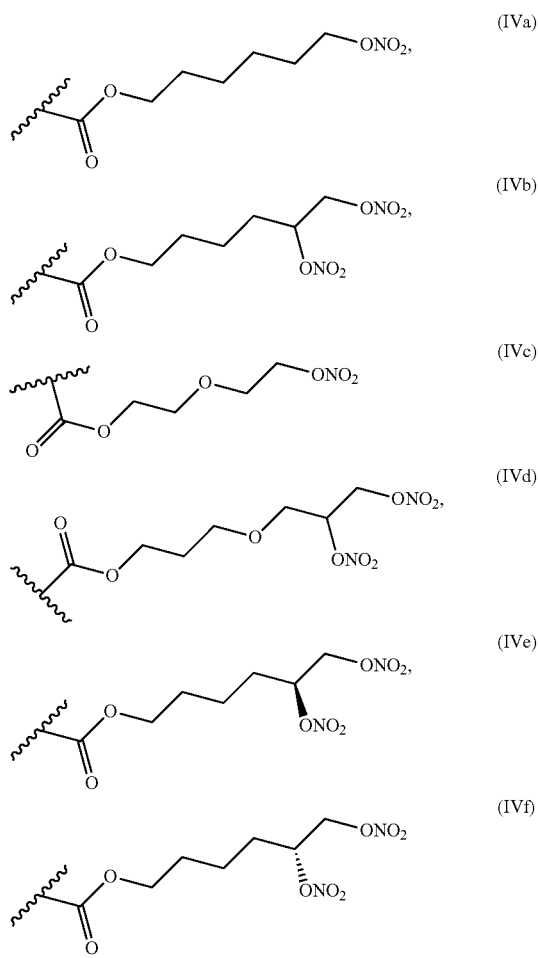

(IVg)
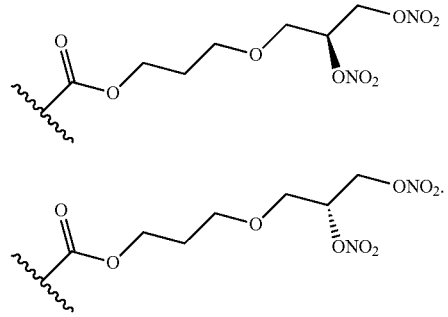

or (IVh)
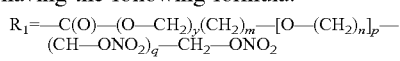

Another embodiment of the invention provides compounds of formula (I) stereoisomers or salts thereof as defined above wherein:
$R_1$ is the residue of a nitric oxide releasing molecule having the following formula:
$$R_1 = -C(O)-(O-CH_2)_y(CH_2)_m-[O-(CH_2)_n]_p-(CH-ONO_2)_q-CH_2-ONO_2$$
wherein:
y is 1 or 0;
p is 1 or 0;
q is 1 or 0;
m is an integer ranging from 1 to 10; preferably m is from 1 to 6;
n is an integer ranging from 1 to 6; preferably n is 1 or 2;
$R_2$ is ethyl and $R_3$ is methyl.

When y=0, $R_1$ is preferably selected from the group consisting of:

(IIIa)
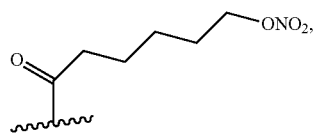

(IIIb)
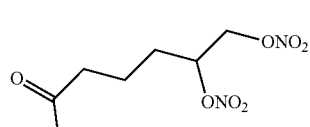

(IIIc)
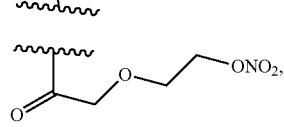

(IIId)
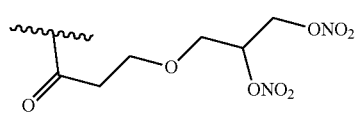

(IIIe)
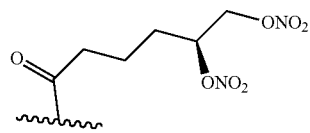

(IIIf)
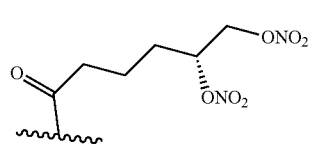

(IIIg)
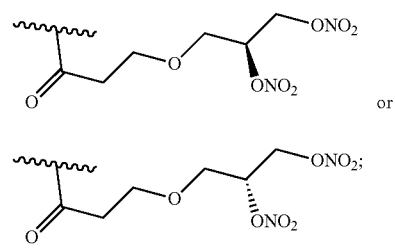

or (IIIh)
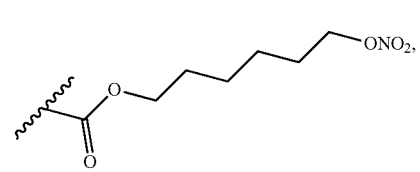

When y=1, $R_1$ is preferably selected from the group consisting of:

(IVa)
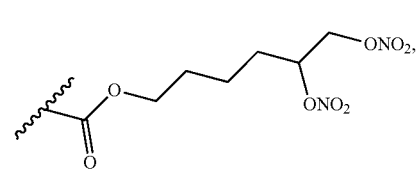

(IVb)
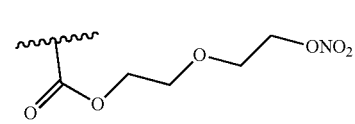

(IVc)
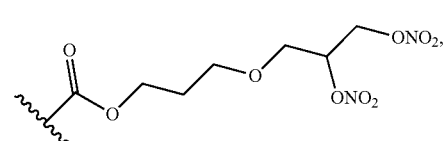

(IVd)
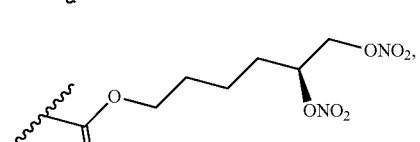

(IVe)
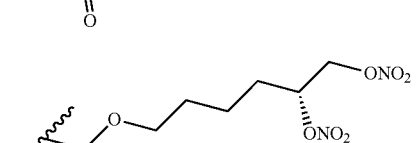

(IVf)
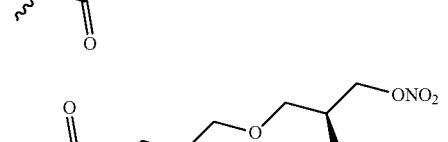

(IVg)
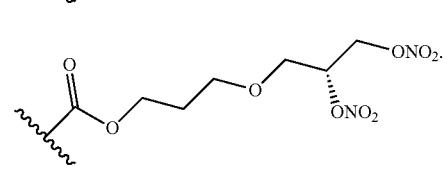

or (IVh)

Another embodiment of the invention provides compounds of formula (I) stereoisomers or salts thereof as defined above wherein:
$R_2$ is ethyl and $R_3$ is methyl;
$R_1$ is the residue of a nitric oxide releasing molecule having the following formula:
y=0 and $R_1$ is selected from the group consisting of:

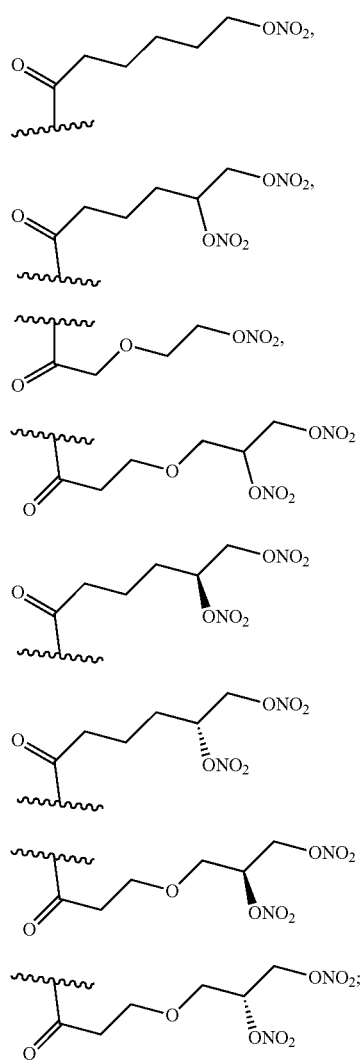

Another embodiment of the invention provides compounds of formula (I) stereoisomers or salts thereof as defined above wherein:
$R_2$ is ethyl and $R_3$ is methyl;
$R_1$ is the residue of a nitric oxide releasing molecule having the following formula:
y=1 and $R_1$ is selected from the group consisting of:

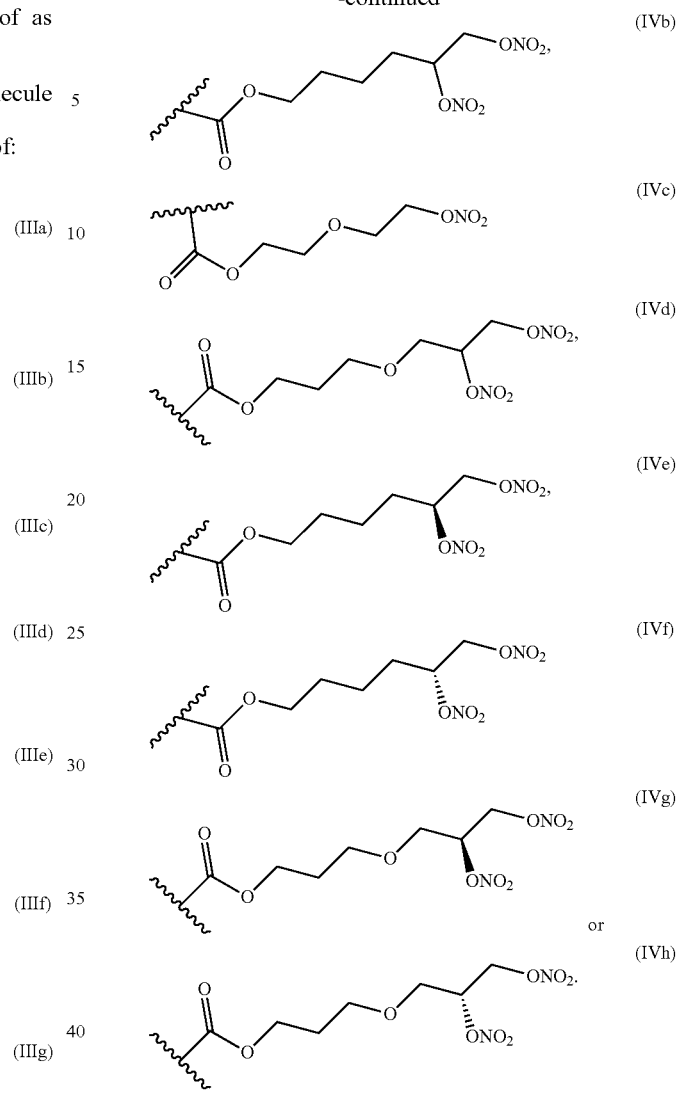

Another embodiment of the invention provides compounds of formula (II) stereoisomers or salts thereof

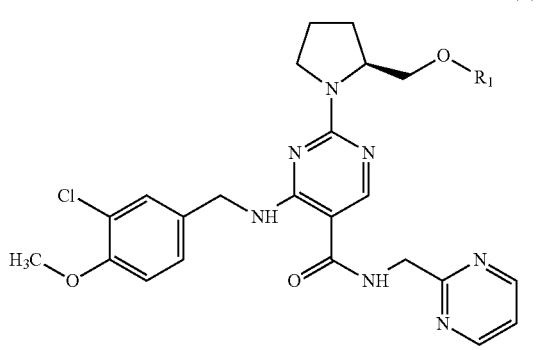

wherein $R_1$ is the residue of a nitric oxide releasing molecule having the following formula:

$R_1$=—C(O)—(O—CH$_2$)$_y$(CH$_2$)$_m$—[O—(CH$_2$)$_n$]$_p$—(CH—ONO$_2$)$_q$—CH$_2$—ONO$_2$ wherein:

y is 1 or 0 p is 1 or 0;

q is 1 or 0;

m is an integer ranging from 1 to 10; preferably m is from 1 to 6;

n is an integer ranging from 1 to 6; preferably n is 1 or 2;

where y=0, $R_1$ is preferably selected from the group consisting of:

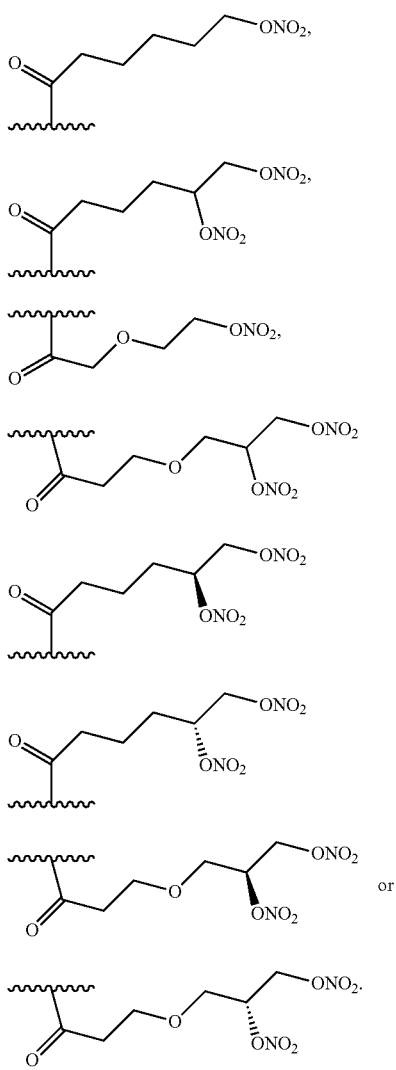

When y=1, $R_1$ is preferably selected from the group consisting of:

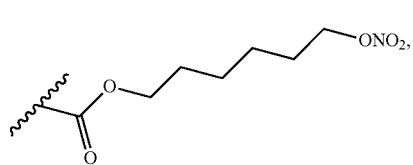

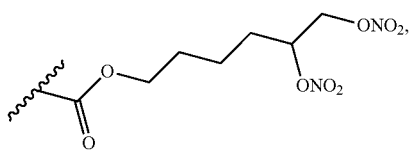

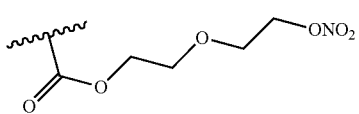

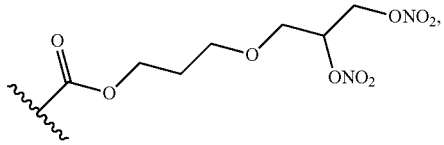

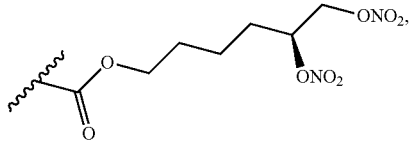

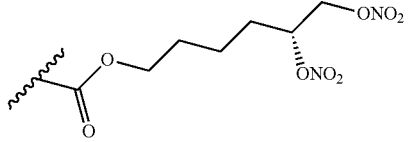

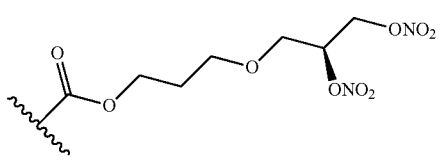

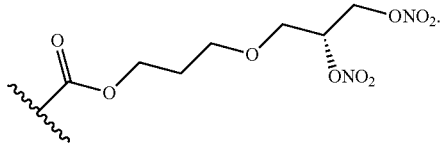

or

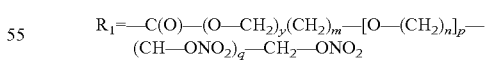

Another embodiment of the invention provides compounds of formula (II) stereoisomers or salts thereof as defined above wherein $R_1$ is the residue of a nitric oxide releasing molecule having the following formula:

$$R_1 = -C(O)-(O-CH_2)_y(CH_2)_m-[O-(CH_2)_n]_p-(CH-ONO_2)_q-CH_2-ONO_2$$

wherein:

y=0 and $R_1$ is selected from the group consisting of:

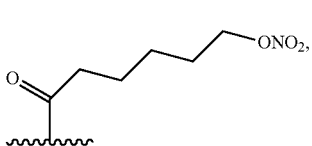

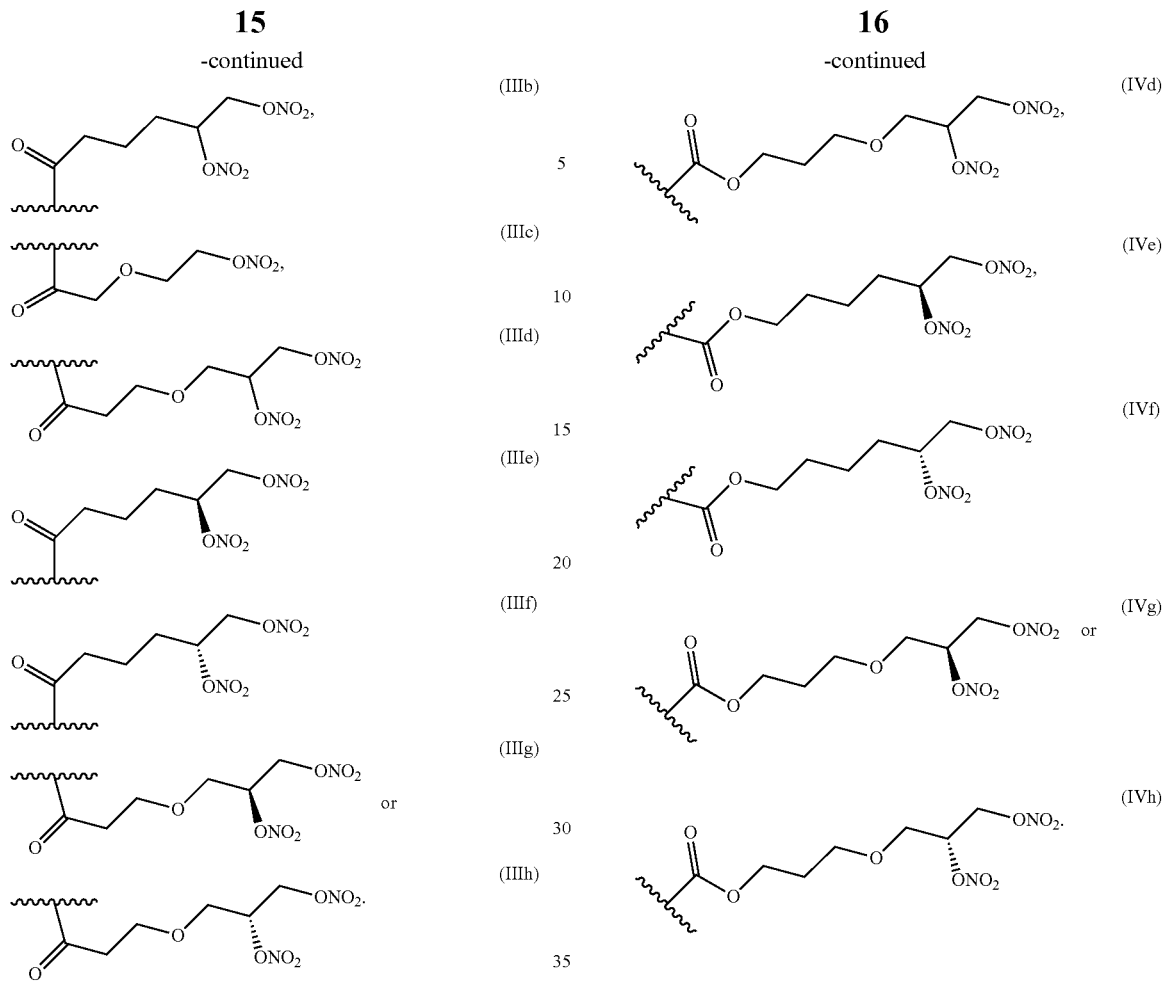

Another embodiment of the invention provides compounds of formula (II) stereoisomers or salts thereof as defined above wherein $R_1$ is the residue of a nitric oxide releasing molecule having the following formula:

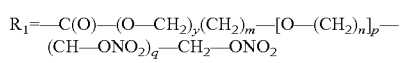

wherein:
y=1 and $R_1$ is selected from the group consisting of:

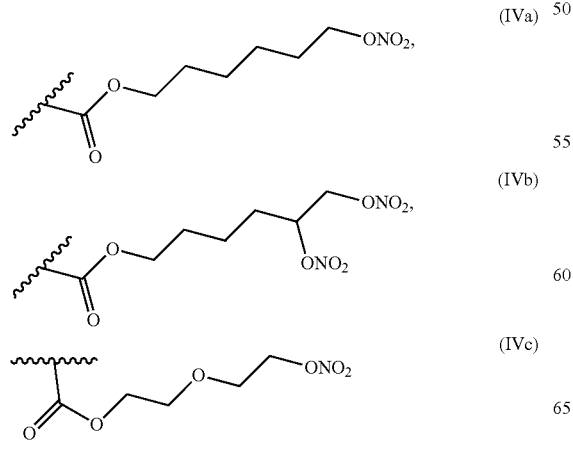

Another embodiment of the invention provides compounds of formula (Ib) stereoisomers or salts said compounds having formula

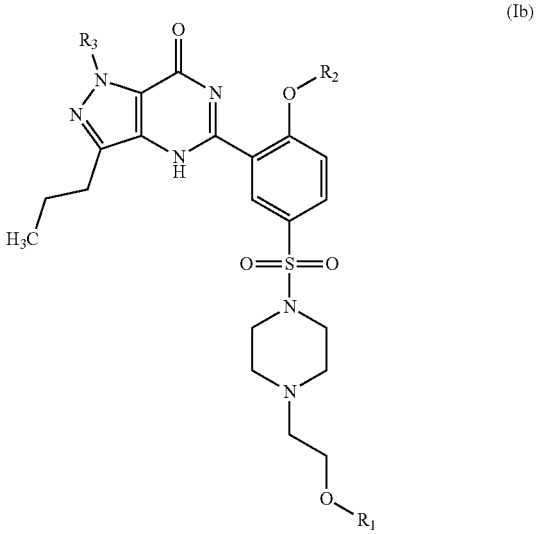

wherein:
$R_1$ is the residue of a nitric oxide releasing molecule having the following formula:

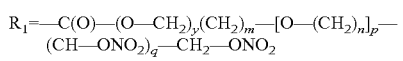

wherein:

y is 1 or 0;

p is 1 or 0;

q is 1 or 0;

m is an integer ranging from 1 to 10; preferably m is from 1 to 6;

n is an integer ranging from 1 to 6; preferably n is 1 or 2;

$R_2$ is ethyl or n-propyl;

$R_3$ is methyl or ethyl;

with the proviso that when $R_2$ is ethyl then $R_3$ is methyl; when $R_2$ is n-propyl then $R_3$ is ethyl; and with the proviso that when $R_2$ is ethyl and $R_3$ is methyl, y is 0, p and q are 0, then m is not 2.

When y is 0, the preferred compounds of formula (Ib) are those wherein $R_1$ is selected from the group consisting of the radicals of formula (IIIa)-(IIIh):

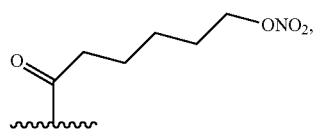
(IIIa)

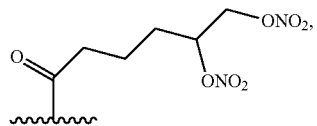
(IIIb)

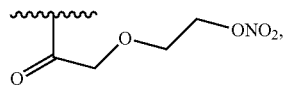
(IIIc)

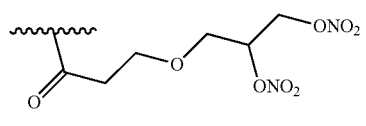
(IIId)

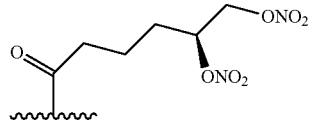
(IIIe)

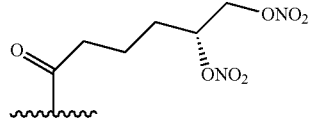
(IIIf)

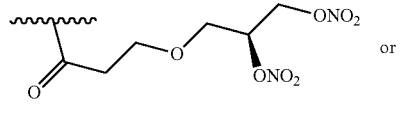
(IIIg)
or

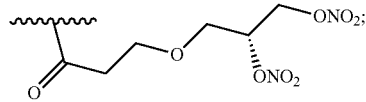
(IIIh)

When y is 1, the preferred compounds of formula (Ib) are those wherein $R_1$ is selected from the group consisting of the radicals of formula (IVa)-(IVh):

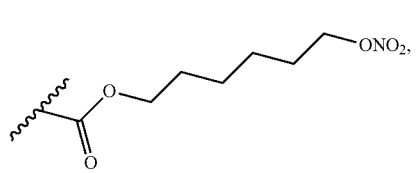
(IVa)

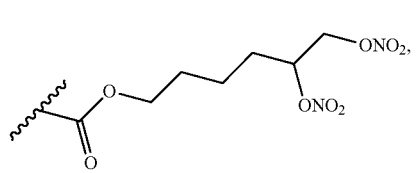
(IVb)

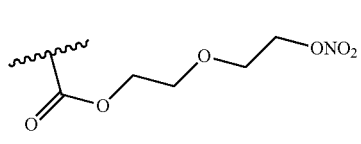
(IVc)

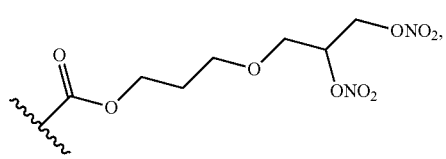
(IVd)

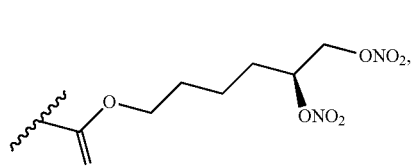
(IVe)

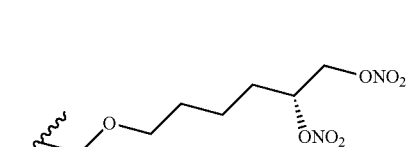
(IVf)

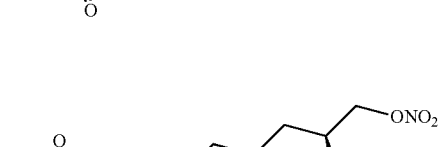
(IVg)
or

(IVh)

Another embodiment of the invention provides compounds of formula (Ib) stereoisomers or salts thereof as defined above wherein $R_1$, y, p, q, m and n, are as defined above, $R_2$ is ethyl and $R_3$ is methyl.

Another embodiment of the invention provides compounds of formula (Ib) stereoisomers or salts thereof

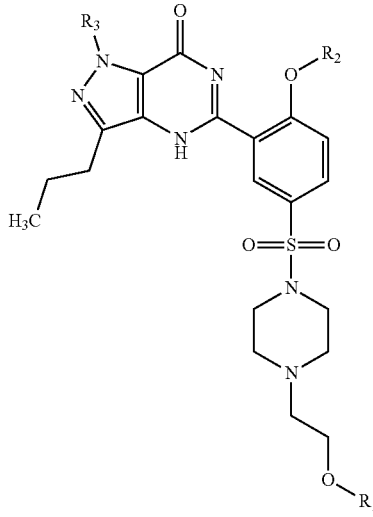

(Ib)

wherein:
R₁ is the residue of a nitric oxide releasing molecule having the following formula:

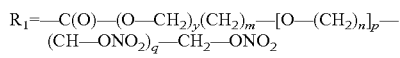

wherein:
y is 1;
p is 1 or 0;
q is 1 or 0;
m is an integer ranging from 1 to 10; preferably m is from 1 to 6;
n is an integer ranging from 1 to 6; preferably n is 1 or 2;
$R_2$ is ethyl or n-propyl;
$R_3$ is methyl or ethyl;
with the proviso that when $R_2$ is ethyl then $R_3$ is methyl and when $R_2$ is n-propyl then $R_3$ is ethyl.

Another embodiment of the invention provides compounds of formula (Ib) stereoisomers or salts thereof as defined above wherein p, q, m, n are as defined above, $R_2$ is ethyl, $R_3$ is methyl and $R_1$ is selected from the group consisting of the radicals of formulae (IIIa)-(IIIh) as defined above.

Another embodiment of the invention provides compounds of formula (Ib) stereoisomers or salts thereof as defined above wherein p, q, m, n are as defined above, $R_2$ is ethyl, $R_3$ is methyl and $R_1$ is selected from the group consisting of the radicals of formulae (IVa)-(IVb) as defined above.

Another embodiment of the invention provides compounds of formula (Ib) stereoisomers or salts thereof as defined above wherein $R_1$, y, p, q, m and n, are as defined above and $R_2$ is n-propyl and $R_3$ is ethyl.

Another embodiment of the invention provides compounds of formula (Ib) stereoisomers or salts thereof as defined above wherein p, q, m, n are as defined above, $R_2$ is n-propyl, $R_3$ is ethyl and $R_1$ is selected from the group consisting of the radicals of formulae (IIIa)-(IIIh) as defined above.

Another embodiment of the invention provides compounds of formula (Ib) stereoisomers or salts thereof as defined above wherein p, q, m, n are as defined above, $R_2$ is n-propyl, $R_3$ is ethyl and $R_1$ is selected from the group consisting of the radicals of formulae (IVa)-(IVh) as defined above.

Another embodiment of the invention provides a compound of formula (I) or (Ib) or stereoisomers or pharmaceutically acceptable salts thereof, selected from the group consisting of:

2-(4-(3-(5-ethyl-4-oxo-7-propyl-4,5-dihydro-3H-pyrrolo[3,2-d]pyrimidin-2-yl)-4-propoxyphenylsulfonyl)piperazin-1-yl)ethyl 3-[2,3-bis(nitrooxy)propoxy]propanoate (Compound (1))

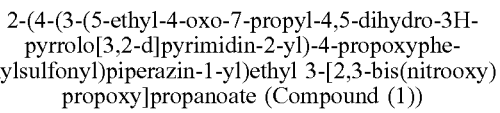

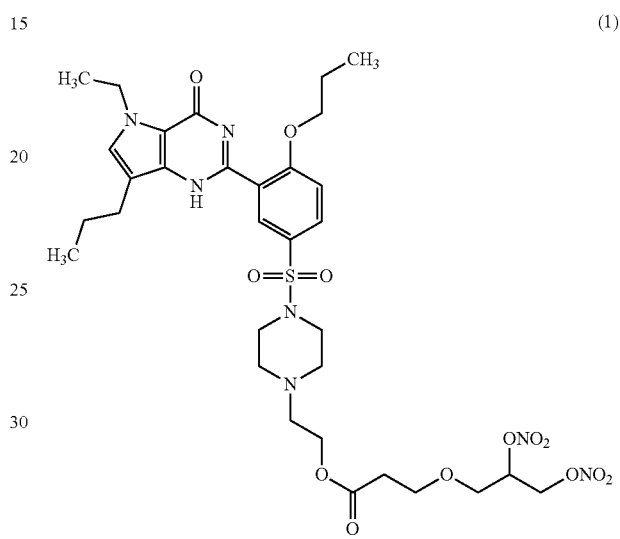

2-(4-((3-(5-ethyl-4-oxo-7-propyl-4,5-dihydro-3H-pyrrolo[3,2-d]pyrimidin-2-yl)-4-propoxyphenyl)sulfonyl)piperazin-1-yl)ethyl 2-(2-(nitrooxy)ethoxy)acetate (Compound (2))

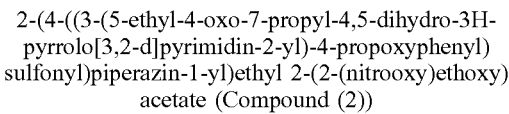

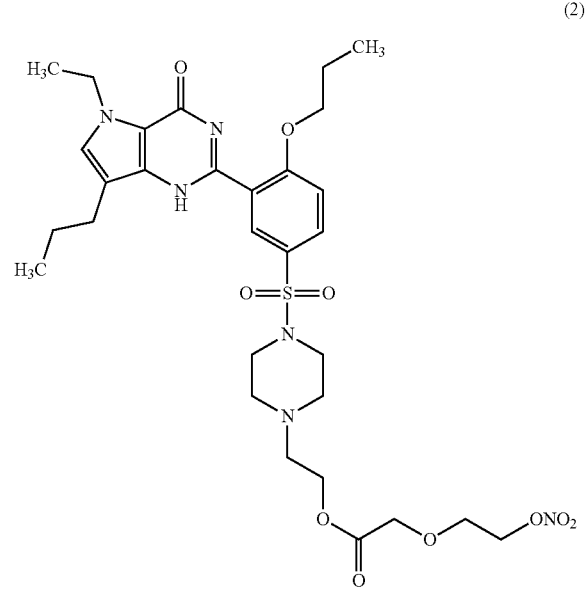

21

2-(4-(3-(5-ethyl-4-oxo-7-propyl-4,5-dihydro-3H-pyrrolo[3,2-d]pyrimidin-2-yl)-4-propoxyphenylsulfonyl)piperazin-1-yl)ethyl 5,6-bis(nitrooxy) hexanoate (Compound (3))

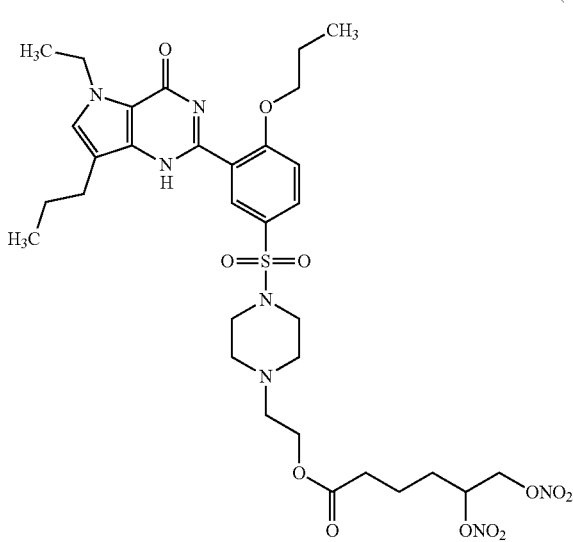

(3)

22

2-(4-(3-(5-ethyl-4-oxo-7-propyl-4,5-dihydro-3H-pyrrolo[3,2-d]pyrimidin-2-yl)-4-propoxyphenylsulfonyl)piperazin-1-yl)ethyl 6-(nitrooxy)hexyl Carbonate (Compound (5))

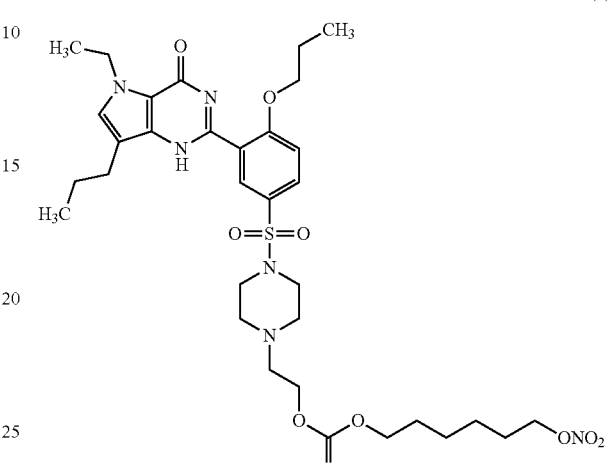

(5)

2-(4-((3-(5-ethyl-4-oxo-7-propyl-4,5-dihydro-3H-pyrrolo[3,2-d]pyrimidin-2-yl)-4-propoxyphenyl)sulfonyl)piperazin-1-yl)ethyl 6-(nitrooxy)hexanoate (Compound (4))

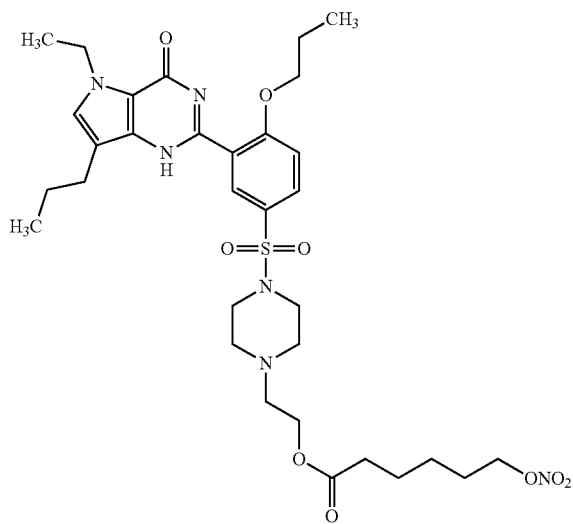

(4)

2-(4-(3-(5-ethyl-4-oxo-7-propyl-4,5-dihydro-3H-pyrrolo[3,2-d]pyrimidin-2-yl)-4-propoxyphenylsulfonyl)piperazin-1-yl)ethyl 5,6-bis(nitrooxy) hexyl Carbonate (Compound (6))

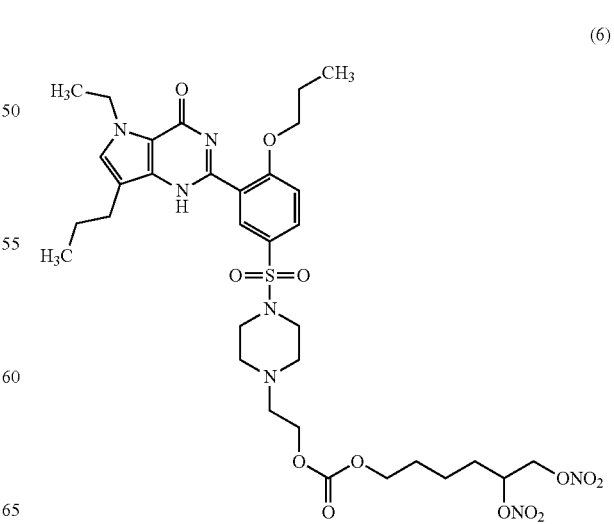

(6)

23

2-{4-[4-ethoxy-3-(5-methyl-4-oxo-7-propyl-4,5-dihydro-1H-pyrrolo[3,2-d]pyrimidin-2-yl)benzene-1-sulfonyl]piperazin-1-yl}ethyl 5,6-bis(nitrooxy)hexanoate (Compound (7))

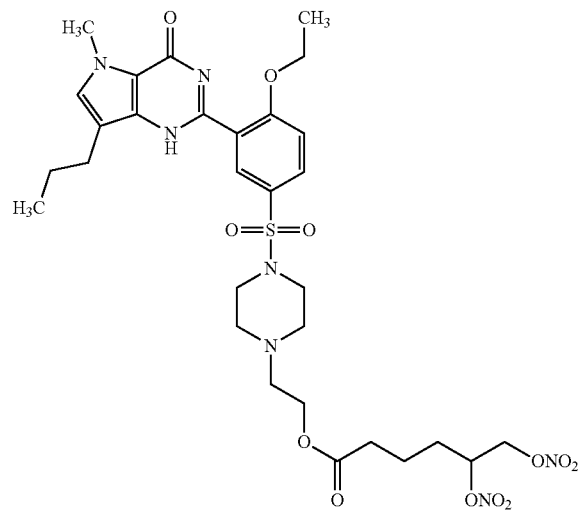

(7)

24

2-{4-[4-ethoxy-3-(1-methyl-7-oxo-3-propyl-6,7-dihydro-1H-pyrazolo[4,3-d]pyrimidin-5-yl)benzene-1-sulfonyl]piperazin-1-yl}ethyl 5,6-bis(nitrooxy)hexanoate (Compound (7b))

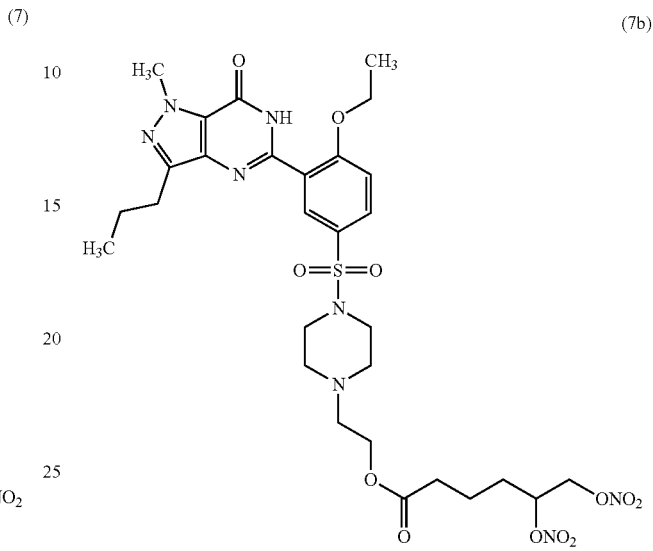

(7b)

2-{4-[4-ethoxy-3-(5-methyl-4-oxo-7-propyl-4,5-dihydro-1H-pyrrolo[3,2-d]pyrimidin-2-yl)benzene-1-sulfonyl]piperazin-1-yl 1 ethyl 6-(nitrooxy)hexanoate (Compound (8))

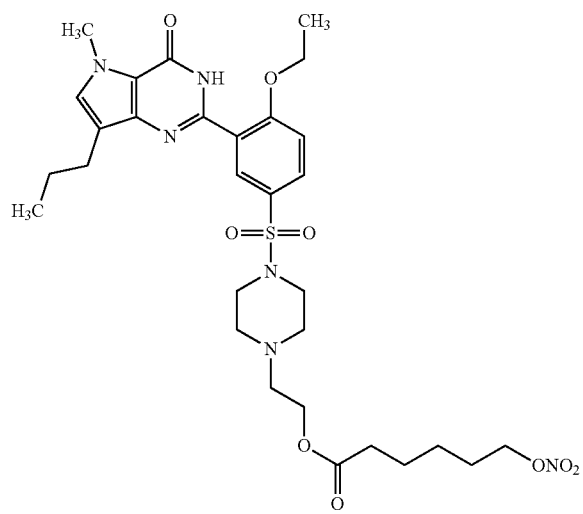

(8)

2-{4-[4-ethoxy-3-(1-methyl-7-oxo-3-propyl-6,7-dihydro-1H-pyrazolo[4,3-d]pyrimidin-5-yl)benzene-1-sulfonyl]piperazin-1-yl}ethyl 6-(nitrooxy)hexanoate (Compound (8b))

(8b)

25

2-{4-[4-ethoxy-3-(1-methyl-7-oxo-3-propyl-6,7-dihydro-1H-pyrazolo[4,3-d]pyrimidin-5-yl)benzene-1-sulfonyl]piperazin-1-yl}ethyl 3-[2,3-bis(nitrooxy)propoxy]propanoate (Compound 15)

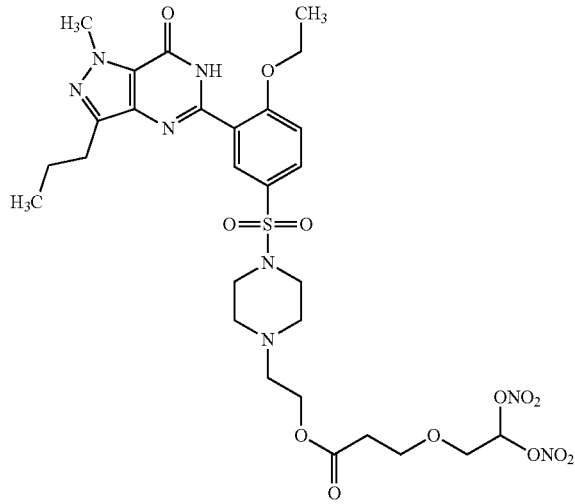

(15)

Another embodiment of the invention provides a compound of formula (II) or stereoisomers or pharmaceutically acceptable salts thereof, said compound of formula (II) is selected from:

(S)-(1-(4-(3-chloro-4-methoxybenzylamino)-5-(pyrimidin-2-ylmethylcarbamoyl) pyrimidin-2-yl)pyrrolidin-2-yl)methyl 6-(nitrooxy)hexanoate (Compound (9))

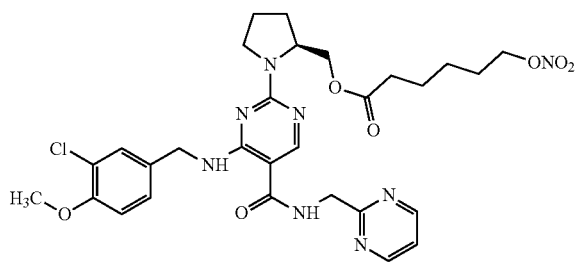

(9)

26

[(2S)-1-(4-{[(3-chloro-4-methoxyphenyl)methyl]amino}-5-{[(pyrimidin-2-yl) methyl]carbamoyl}pyrimidin-2-yl)pyrrolidin-2-yl]methyl 5,6-bis(nitrooxy)hexanoate (Compound (10))

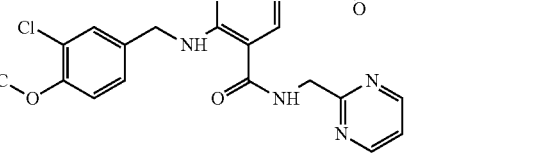

(10)

(S)-(1-(4-(3-chloro-4-methoxybenzylamino)-5-(pyrimidin-2-ylmethylcarbamoyl) pyrimidin-2-yl)pyrrolidin-2-yl)methyl 2-(2-(nitrooxy)ethoxy)acetate (Compound (11))

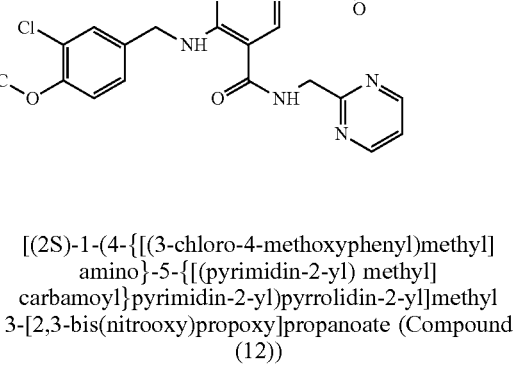

(11)

[(2S)-1-(4-{[(3-chloro-4-methoxyphenyl)methyl]amino}-5-{[(pyrimidin-2-yl) methyl]carbamoyl}pyrimidin-2-yl)pyrrolidin-2-yl]methyl 3-[2,3-bis(nitrooxy)propoxy]propanoate (Compound (12))

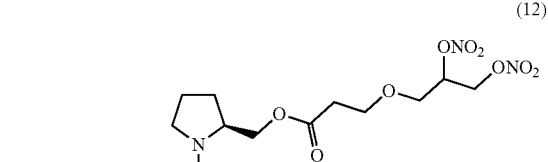

(12)

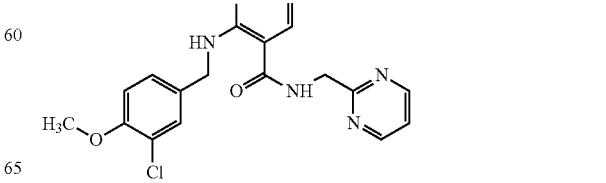

(S)-(1-(4-(3-chloro-4-methoxybenzylamino)-5-(pyrimidin-2-ylmethylcarbamoyl) pyrimidin-2-yl)pyrrolidin-2-yl)methyl 6-(nitrooxy)hexyl Carbonate (Compound (13))

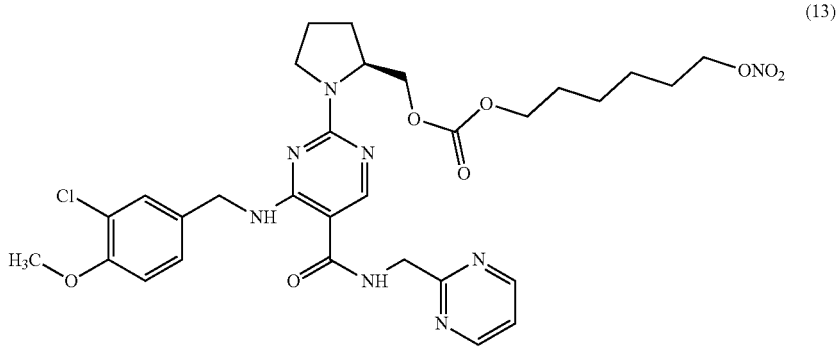

((S)-1-(4-(3-chloro-4-methoxybenzylamino)-5-(pyrimidin-2-ylmethylcarbamoyl) pyrimidin-2-yl)pyrrolidin-2-yl)methyl 5,6-bis(nitrooxy)hexyl Carbonate (Compound (14))

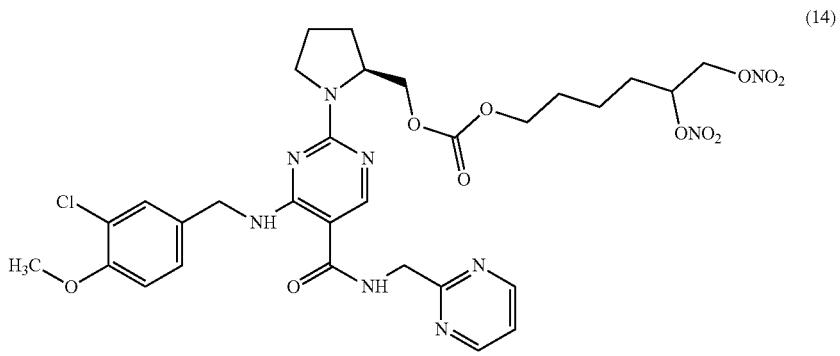

Another embodiment of the invention provides a compound of formula (I), (Ib) or (II) is selected from group consisting of:

- [(2S)-1-(4-{[(3-chloro-4-methoxyphenyl)methyl]amino}-5-{[(pyrimidin-2-yl) methyl]carbamoyl}pyrimidin-2-yl) pyrrolidin-2-yl]methyl (5S)-5,6-bis(nitrooxy) hexanoate (Compound (10)-(5S));
- [(2S)-1-(4-{[(3-chloro-4-methoxyphenyl)methyl]amino}-5-1[(pyrimidin-2-yl) methyl]carbamoyl}pyrimidin-2-yl) pyrrolidin-2-yl]methyl 3-[(2S)-2,3-bis(nitrooxy) propoxy]propanoate (Compound (12)-(2S));
- (S)-(1-(4-(3-chloro-4-methoxybenzylamino)-5-(pyrimidin-2-ylmethylcarbamoyl) pyrimidin-2-yl)pyrrolidin-2-yl) methyl 6-(nitrooxy)hexanoate 2-hydroxypropane-1,2,3-tricarboxylate (Compound (9))-citrate salt);
- (S)—((S)-1-(4-(3-chloro-4-methoxybenzylamino)-5-(pyrimidin-2-ylmethyl carbamoyl)pyrimidin-2-yl)pyrrolidin-2-yl)methyl (5S)-5,6-bis(nitrooxy)hexanoate 2-hydroxypropane-1,2,3-tricarboxylate (Compound (10)-(5S) citrate salt);
- (S)-(1-(4-(3-chloro-4-methoxybenzylamino)-5-(pyrimidin-2-ylmethylcarbamoyl) pyrimidin-2-yl)pyrrolidin-2-yl) methyl 2-(2-(nitrooxy)ethoxy)acetate 2-hydroxy propane-1,2,3-tricarboxylate (Compound (11) citrate salt);
- ((S)-1-(4-(3-chloro-4-methoxybenzylamino)-5-(pyrimidin-2-ylmethylcarbamoyl) pyrimidin-2-yl)pyrrolidin-2-yl) methyl 3-((S)-2,3-bis(nitrooxy)propoxy)propanoate 2-hydroxypropane-1,2,3-tricarboxylate (Compound (12)-(2S) citrate salt);
- (S)-2-(4-(3-(5-ethyl-4-oxo-7-propyl-4,5-dihydro-3H-pyrrolo[3,2-d]pyrimidin-2-yl)-4-propoxyphenylsulfonyl) piperazin-1-yl)ethyl 3-[2,3-bis(nitrooxy)propoxy]propanoate citrate (Compound (1)-(2S) citrate salt);
- 2-(4-(3-(5-ethyl-4-oxo-7-propyl-4,5-dihydro-3H-pyrrolo[3,2-d]pyrimidin-2-yl)-4-propoxyphenylsulfonyl)piperazin-1-yl)ethyl 6-(nitrooxy)hexanoate citrate (Compound (4) citrate salt);
- 2-hydroxypropane-1,2,3-tricarboxylic acid 2-{4-[3-(5-ethyl-4-oxo-7-propyl-4,5-dihydro-3H-pyrrolo[3,2-d]pyrimidin-2-yl)-4-propoxybenzene-1-sulfonyl]piperazin-1-yl}ethyl[2-(nitrooxy)ethoxy]acetate (Compound (2) citrate salt);
- (S)-2-(4-(3-(5-ethyl-4-oxo-7-propyl-4,5-dihydro-3H-pyrrolo[3,2-d]pyrimidin-2-yl)-4-propoxyphenylsulfonyl) piperazin-1-yl)ethyl 5,6-bis(nitrooxy)hexanoate citrate (Compound (3)-(5S) citrate salt);
- (S)-2-(4-(3-(5-ethyl-4-oxo-7-propyl-4,5-dihydro-3H-pyrrolo[3,2-d]pyrimidin-2-yl)-4-propoxyphenylsulfonyl) piperazin-1-yl)ethyl 3-(2,3-bis(nitrooxy)propoxy) propanoate dihydrochloride (Compound (1)-(2S) HCl salt);

((S)-1-(4-(3-chloro-4-methoxybenzylamino)-5-(pyrimidin-2-ylmethylcarbamoyl) pyrimidin-2-yl)pyrrolidin-2-yl)methyl (S)-5,6-bis(nitrooxy)hexyl carbonate (Compound (14)-(5S));

(S)-(1-(4-(3-chloro-4-methoxybenzylamino)-5-(pyrimidin-2-ylmethylcarbamoyl) pyrimidin-2-yl)pyrrolidin-2-yl)methyl 6-(nitrooxy)hexyl carbonate 2-hydroxypropane-1,2,3-tricarboxylate (Compound (13) citrate salt);

(S)-2-(4-((4-ethoxy-3-(1-methyl-7-oxo-3-propyl-6,7-dihydro-1H-pyrazolo[4,3-d]pyrimidin-5-yl)phenyl)sulfonyl)piperazin-1-yl)ethyl (S)-5,6-bis(nitrooxy)hexanoate (Compound (7b)-(5S));

(S)-2-(4-((4-ethoxy-3-(1-methyl-7-oxo-3-propyl-6,7-dihydro-1H-pyrazolo[4,3-d]pyrimidin-5-yl)phenyl)sulfonyl)piperazin-1-yl)ethyl-(S)-3-(2,3-bis(nitrooxy)propoxy)propanoate (Compound (15), (S) isomer);

(S)-(1-(4-(3-chloro-4-methoxybenzylamino)-5-(pyrimidin-2-ylmethylcarbamoyl) pyrimidin-2-yl)pyrrolidin-2-yl)methyl 6-(nitrooxy)hexanoate fumarate (Compound (9) fumarate salt);

(S)-(1-(4-(3-chloro-4-methoxybenzylamino)-5-(pyrimidin-2-ylmethylcarbamoyl) pyrimidin-2-yl)pyrrolidin-2-yl)methyl 6-(nitrooxy)hexanoate maleate (Compound (9) maleate salt).

Another embodiment of the present invention provides a compound of formula (I), or formula (Ib), or of formula (II) or a pharmaceutically acceptable salt thereof for use in a method of treating a disease or a condition associated with elevated intraocular pressure. Preferably said disease or condition is selected from ocular hypertension or glaucoma including open-angle glaucoma, normal-tension glaucoma, pigmentary glaucoma or pseudoexfoliative glaucoma or drug induced glaucoma.

Another embodiment of the present invention provides a compound of formula (I), or formula (Ib), or of formula (II) or a pharmaceutically acceptable salt thereof for use in a method of treating retinopathies including retinopathy of prematurity, retinal vein occlusion or diabetic macular edema.

Another embodiment of the present invention provides ophthalmic pharmaceutical compositions comprising a compound of formula (I), or formula (Ib), or of formula (II) or a stereoisomer or a pharmaceutically acceptable salt thereof and a pharmaceutically acceptable excipient and/or vehicle. The ophthalmic pharmaceutical compositions are in the form of solution, suspension, gel, cream or emulsions.

Certain specific compounds of the present invention may be converted into acid salts. Thus the compounds of the present invention may exist as salts. Examples of such salts are hydrochloric acid, hydrobromic acid, sulfuric acid, phosphoric acid, nitric acid and the like; or an organic acid such as, for example, acetic, hydroxyacetic, propanoic, lactic, pyruvic, malonic, fumaric acid, maleic acid, oxalic acid, tartaric acid, succinic acid, malic acid, ascorbic acid, benzoic acid, tannic acid, pamoic acid, citric, methylsulfonic, ethanesulfonic, benzenesulfonic, formic and the like.

Included within the scope of the present invention are the individual enantiomers of the compounds of formula (I), of formula (II), or of formula (Ib), as well as their diasteroisomers, racemic and non-racemic mixtures.

Another embodiment of the invention relates to a composition comprising a compound of formula (I), or of formula (Ib), or a compound of formula (II)) and at least another active agent selected from the following classes of drugs:

beta-adrenergic antagonists wherein the beta-adrenergic antagonist is selected from: carteolol, levobunolol, metipranolol or timolol;

prostaglandin analogues wherein the prostaglandin analogue is selected from: latanoprost, travoprost, tafluprost or bimatoprost or their respective NO donating derivatives;

adrenergic agonists wherein the adrenergic agonist is selected from: epinephrine borate, epinephrine hydrochloride, dipivefrin or apraclonidine;

carbonic anhydrase inhibitors wherein the carbonic anhydrase inhibitor is selected from: acetazolamide, dichlorphenamide, methazolamide, brinzolamide or dorzolamide;

cholinergic agonists wherein the cholinergic agonist is selected from: carbachol, pilocarpine hydrochloride, pilocarpine nitrate or pilocarpine;

steroids wherein the steroid is selected from: fluocinolone, fluticasone propionate, triamcinolone or dexamethasone;

cholinesterase inhibitors wherein the cholinesterase inhibitor is selected from: demecarium, echothiophate or physostigmine;

soluble guanylate cyclase activators (sCG activators), preferably the sCG activators are compounds disclosed in WO 2016/001875, more preferably the sCG activator is (+)-1-(6-(3-((4-(1-(cyclopropanecarbonyl)piperidin-4-yl)-2-methylphenyl)amino)-2,3-dihydro-1H-inden-4-yl)pyridin-2-yl)-5-methyl-1H-pyrazole-4-carboxylic (MGV-354) disclosed in WO 2016/001875;

Rho-kinase inhibitors which include Netarsudil, Ripasudil, Fasudil, Verosudil, (+)-(R)-trans-4-(1-aminoethyl)-N-(4-pyridyl)cyclohexanecarboxamide dihydrochloride (Y-27632) or (R)-(+)-N-(1H-pyrrolo[2,3-b]pyridin-4-yl)-4-(1-aminoethyl)benzamide (Y-39383) disclosed in US 2012/0288428;

the sGC activator cinaciguat.

The above compositions comprising a compound of formula (I), or a compound of formula (Ib), or a compound of formula (II) and at least another active agent selected from beta-adrenergic antagonists, prostaglandin analogues, adrenergic agonists, carbonic anhydrase inhibitors, cholinergic agonists, steroids, cholinesterase inhibitors, soluble guanylate cyclase activators or Rho-kinase inhibitors may be prepared in one dosage form containing a suitable mixing ratio of the two active compounds or as a kit for simultaneously or separately administration of the two active compounds that are prepared in separate dosage forms.

Another embodiment of the invention provides a composition which is a kit comprising a topical ocular dosage form comprising a compound of formula (I), or a compound of formula (Ib), or a compound of formula (II) or salts thereof and another topical ocular dosage form comprising an active agent selected from the following classes of drugs: prostaglandin analogues, beta-adrenergic antagonists, carbonic anhydrase inhibitors, cholinergic agonists, steroids, cholinesterase inhibitors, soluble guanylate cyclase activators or Rho-kinase inhibitors or the sGC activator cinaciguat.

Another embodiment provides the use of the compositions comprising a compound of formula (I), or a compound of formula (Ib), or a compound of formula (II) and at least another active agent reported above for use in a method of treating a disease or a condition associated with elevated ocular pressure. Preferably said disease or condition is selected from ocular hypertension or glaucoma including open-angle glaucoma, normal-tension glaucoma, pigmentary glaucoma, pseudoexfoliative glaucoma or drug induced glaucoma.

Another embodiment provides the use of the compositions comprising a compound of formula (I), or a compound of formula (Ib), or a compound of formula (II) and at least another active agent reported above for use in a method of treating retinopathies including retinopathy of prematurity, retinal vein occlusion or diabetic macular edema.

In the compositions for topical administration, the concentration of the compounds of the invention is generally from 0.0001% to 3% (w/v) or from 0.003% to 3% (w/v), preferably from 0.03% to 2% (w/v) and, most preferably from 0.3% to 1% (w/v).

Another embodiment of the invention provides 3-[(2S)-2,3-bis(nitrooxy)propoxy]propanoic acid (compound (IIIg)-OH) or 6-(nitrooxy)hexanoic acid (compound (IIIa)-OH) for use as intraocular pressure reducing agents for treating ocular diseases or conditions associated with elevated intraocular pressure Another embodiment of the invention provides 3-[(2S)-2,3-bis(nitrooxy)propoxy]propanoic acid (compound (IIIg)-OH) or 6-(nitrooxy)hexanoic acid (compound (IIIa)-OH) for use in a method of treating retinopathies including retinopathy of prematurity, retinal vein occlusion or diabetic macular edema.

Another embodiment of the invention provides ophthalmic composition comprising the compound 3-[(2S)-2,3-bis(nitrooxy)propoxy]propanoic acid ((IIIg)-OH) or the compound 6-(nitrooxy)hexanoic acid ((IIIa)-OH) and at least a pharmaceutical acceptable excipient and/or vehicle.

Another embodiment of the invention provides ophthalmic composition comprising the compound 3-[(2S)-2,3-bis(nitrooxy)propoxy]propanoic acid ((IIIg)-OH) or the compound 6-(nitrooxy)hexanoic acid ((IIIa)-OH) and at least another active agent selected from the following classes of drugs: beta-adrenergic antagonists, prostaglandin analogues, adrenergic agonists, carbonic anhydrase inhibitors, cholinergic agonists, steroids, cholinesterase inhibitors, soluble guanylate cyclase activators, Rho-kinase inhibitors or cinaciguat.

The composition may be prepared in one dosage form containing a suitable mixing ratio of the two active compounds or as a kit for simultaneous or separate administration of the two active compounds that are prepared in separate dosage forms.

General Synthesis
Compounds of Formula (I) and Formula (II)

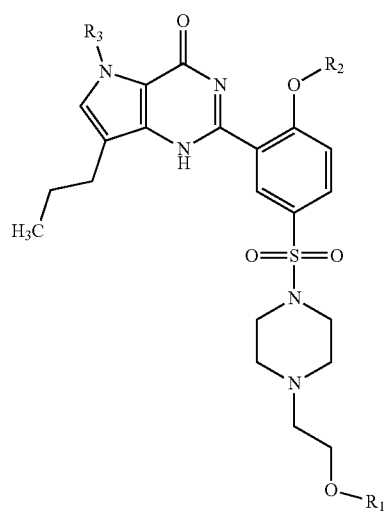

(I)

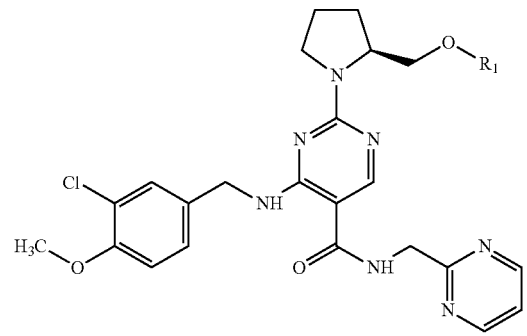

(II)

wherein:

$R_1$=—C(O)—(O—CH$_2$)$_y$(CH$_2$)$_m$—[O—(CH$_2$)$_n$]$_p$—(CH—ONO$_2$)$_q$—CH$_2$—ONO$_2$ y=0, p is 1 or 0, q is 1 or 0, m is an integer ranging from 1 to 10; preferably m is from 1 to 6, n is an integer ranging from 1 to 6; preferably n is 1 or 2, $R_2$ is n-propyl and $R_3$ is ethyl or $R_2$ is ethyl and $R_3$ is methyl, can be prepared by reacting a compound of formula A1, A2 or A3

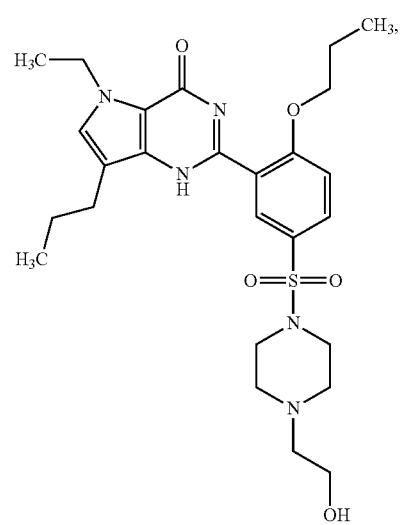

A1

-continued

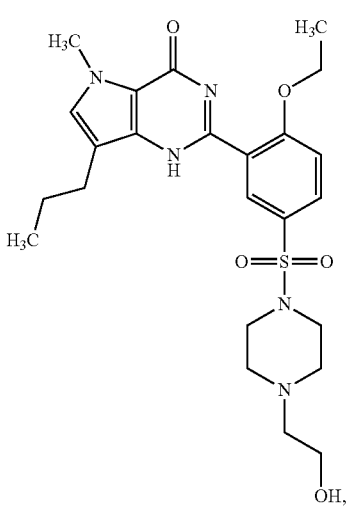
A2

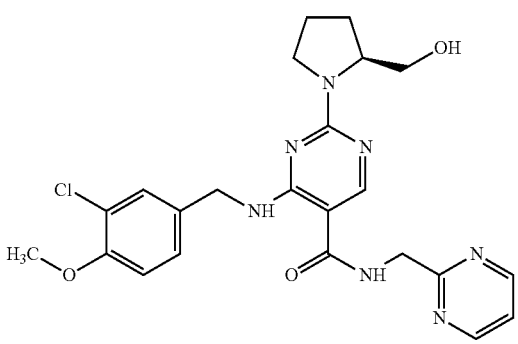
A3 with compounds of formula B1

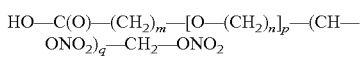
B1 wherein p, q, m and n are as previously defined; the reaction is carried out in a aprotic polar/non polar solvent such as THF, DMF or CH$_2$Cl$_2$, in presence of a coupling agent such as N,N'-dicyclohexylcarbodiimide (DCC), 1-ethyl-3-(3-dimethylaminopropyl)carbodiimide hydrochloride (EDC), O-(benzotriazol-1-yl)-N,N,N',N'-tetramethyluronium hexafluorophosphate (HBTU) or 1-[bis(dimethylamino)methylene]-1H-1,2,3-triazolo[4,5-b]pyridinium 3-oxid hexafluorophosphate (HATU), in presence of variable amount of DMAP at temperature ranging from –0° C. to 80° C.

Alternatively, the compounds of formula (I) can be prepared by reacting a compound of formula A1, A2 or A3 with compounds of formula B2:

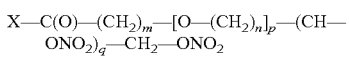
B2 wherein p, q, m and n are as previously defined and X is —Cl, p-nitrophenoxy, pentafluorophenoxy or 2,5-pyrrolidinedione, 1-oxy;

when X=—Cl the reaction is carried out in presence of a base such as DMAP, pyridine or triethylamine or K$_2$CO$_3$, Cs$_2$CO$_3$ in an aprotic/non polar solvent such as THF, DMF or CH$_2$Cl$_2$, at a temperature ranging from –20° C. to 60° C.

When X is selected from p-nitrophenoxy, pentafluorophenoxy or 2,5-pyrrolidinedione, 1-oxy, the reaction is carried out in a aprotic polar/non polar solvent such as THF, DMF or CH$_2$Cl$_2$, in presence of DMAP, with or without a catalyst such as scandium triflate at temperature ranging from 0° C. to 80° C.

Compound A1 is known in the literature as mirodenafil. Compounds A1 and A2 are disclosed in U.S. Pat. No. 6,962,911.

Compound A3 is known in the literature as avanafil, its synthesis is disclosed in U.S. Pat. No. 6,656,935.

Compound of formula B2 are generally prepared from compounds B1 with methods known in the literature.

Compounds B1 are known in the art or can be prepared by known methods from known compounds: for example, compounds B1 can be prepared from the corresponding alcohols of formula B3

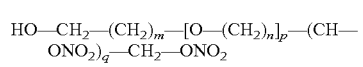
B3

Wherein m, n, p and q are as above defined by oxidation with known agents such as 2,2,6,6-Tetramethylpiperidinyloxy (TEMPO) or Ruthenium (IV) oxide/Sodium periodate.

Examples of synthesis of compounds (B1) are described in WO2009/098113 or in WO2016/155906.

Compounds of formula (I) and formula (II)

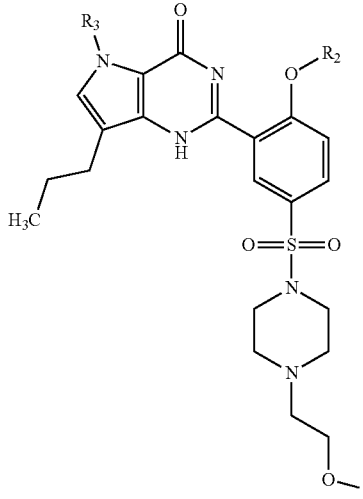
(I)

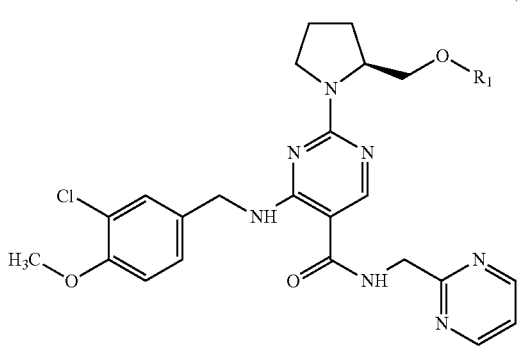
(II)

wherein:

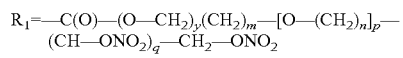

y=1,
p is 1 or 0,
q is 1 or 0, m is an integer ranging from 1 to 10; preferably m is from 1 to 6, n is an integer ranging from 1 to 6; preferably n is 1 or 2, R₂ is n-propyl and R₃ is ethyl or R₂ is ethyl and R₃ is methyl, can be generally prepared by reacting compound of formula A4, A5 or A6

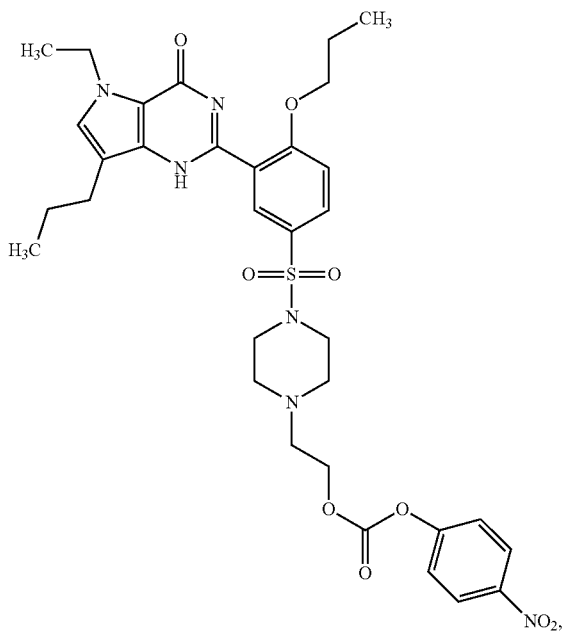

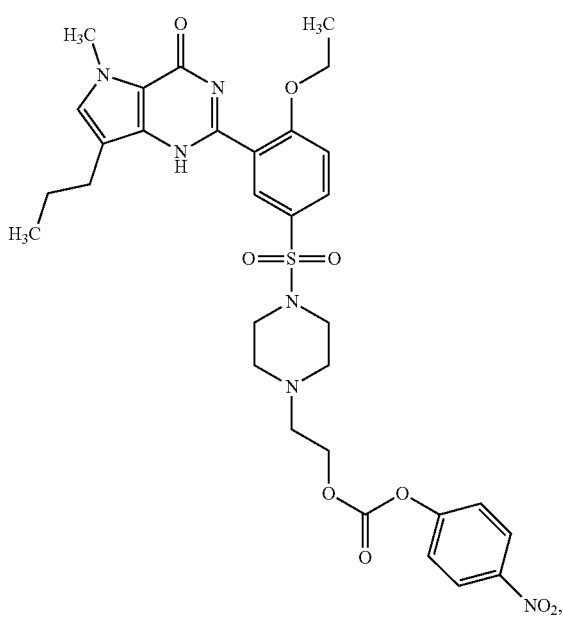

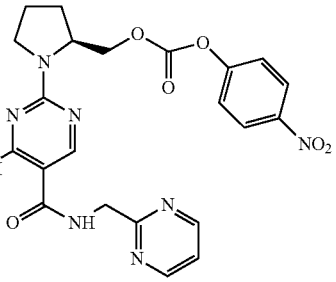

with one or more equivalent of compounds of formula B3

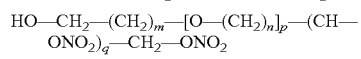

wherein p, q, and n are as previously defined in the presence of an organic or inorganic base such as DMAP, TEA, DIPEA, with or without catalyst such as Sc(OTf)₃ in an aprotic polar/apolar solvent such as THF, DMF CH₂Cl₂ at temperatures ranging between −20° C. to 100° C., following methods being well known in the literature.

Compounds of formula A4, A5 and A6 are prepared from compounds A1, A2 and A3 respectively by methods known in the art.

Alternatively, compounds (I) and (II) can be prepared by reacting compounds A1, A2 or A3 with compounds of formula B4

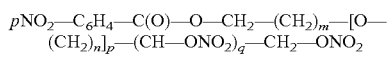

wherein p, q, and n are as previously defined in the presence of an organic or inorganic base such as DMAP, TEA, DIPEA, with or without a catalyst such as Sc(OTf)₃ in an aprotic polar/apolar solvent such as THF, DMF CH₂Cl₂ at temperatures ranging between −20° C. to 100° C., following methods being well known in the literature.

Compounds of formula B4, are easily prepared from compounds B3 by methods known in the art.

Compounds of formula (Ib)

(Ib)

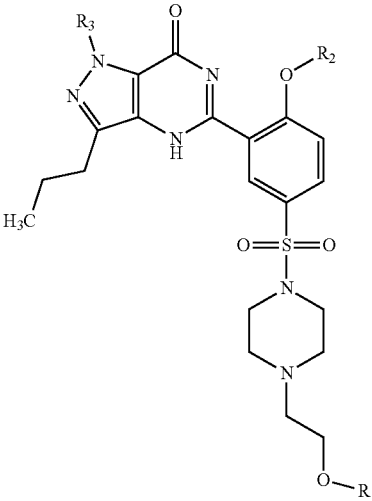

wherein:

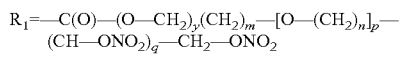

y=0,
p is 1 or 0,
q is 1 or 0,
m is an integer ranging from 1 to 10;
n is an integer ranging from 1 to 6;
$R_2$ is n-propyl and $R_3$ is ethyl or $R_2$ is ethyl and $R_3$ is methyl, can be prepared by reacting a compound of formula A1b, A2b

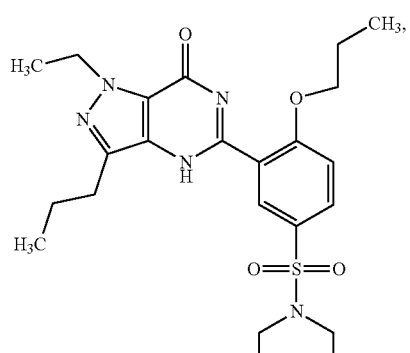

A1b

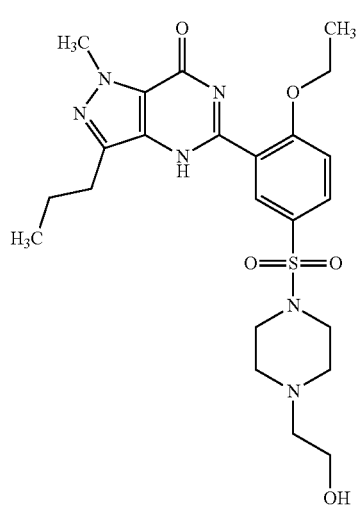

A2b with compounds of formula B1

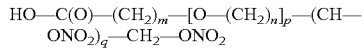

B1 wherein p, q, m and n are as previously defined; the reaction is carried out in a aprotic polar/non polar solvent such as THF, DMF or $CH_2Cl_2$, in presence of a coupling agent such as N,N'-dicyclohexylcarbodiimide (DCC), 1-ethyl-3-(3-dimethylaminopropyl)carbodiimide hydrochloride (EDC), O-(benzotriazol-1-yl)-N,N,N',N'-tetramethyluronium hexafluorophosphate (HBTU) or 1-[bis(dimethylamino)methylene]-1H-1,2,3-triazolo[4,5-b]pyridinium 3-oxid hexafluorophosphate (HATU), in presence of variable amount of DMAP at temperature ranging from –0° C. to 80° C.

Alternatively, the compounds of formula (Ib) can be prepared by reacting a compound of formula A1b or A2b with compounds of formula B2:

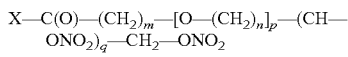

B2 wherein p, q, m and n are as previously defined and X is —Cl, p-nitrophenoxy, pentafluorophenoxy or 2,5-pyrrolidinedione, 1-oxy;

when X=—Cl the reaction is carried out in presence of a base such as DMAP, pyridine or triethylamine or $K_2CO_3$, $Cs_2CO_3$ in an aprotic/non polar solvent such as THF, DMF or $CH_2Cl_2$, at a temperature ranging from –20° C. to 60° C.

When X is selected from p-nitrophenoxy, pentafluorophenoxy or 2,5-pyrrolidinedione, 1-oxy, the reaction is carried out in a aprotic polar/non polar solvent such as THF, DMF or $CH_2Cl_2$, in presence of DMAP, with or without a catalyst such as scandium triflate at temperature ranging from 0° C. to 80° C.

Compounds A1b and A2b are disclosed in EP 0 463 756. A2b is known as lodenafil.

Compound of formula B2 are known in the literature or are generally prepared from compounds B1 with methods known in the literature.

Compounds B1 are known in the art or can be prepared by known methods from known compounds: for example, compounds B1 can be prepared from the corresponding alcohols of formula B3

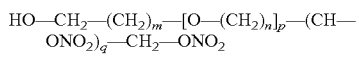

B3 wherein m, n, p and q are as above defined by oxidation with known agents such as 2,2,6,6-Tetramethylpiperidinyloxy (TEMPO) or Ruthenium (IV) oxide/Sodium periodate.

Examples of synthesis of compounds (B1) are described in WO2009/098113 or in WO2016/155906.

Compounds of formula (Ib)

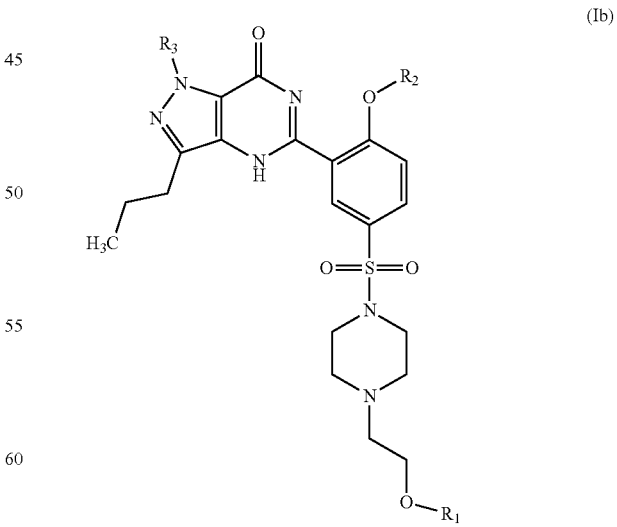

(Ib)

wherein:

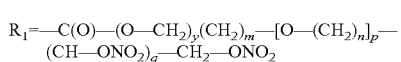

y=1,
p is 1 or 0,
q is 1 or 0,
m is an integer ranging from 1 to 10;
n is an integer ranging from 1 to 6;
$R_2$ is n-propyl and $R_3$ is ethyl (A5b) or $R_2$ is ethyl and $R_3$ is methyl (A4b), can be generally prepared by reacting compound of formula A4b or A5b A4b A5b with one or more equivalent of compounds of formula B3

HO—$CH_2$—$(CH_2)_m$—[O—$(CH_2)_n]_p$—(CH—$ONO_2)_q$—$CH_2$—$ONO_2$  B3 wherein m, p, q, and n are as previously defined in the presence of an organic or inorganic base such as DMAP, TEA, DIPEA, with or without catalyst such as Sc(OTf)$_3$ in an aprotic polar/apolar solvent such as THF, DMF CH$_2$Cl$_2$ at temperatures ranging between −20° C. to 100° C., following methods being well known in the literature.

Compounds of formula A4b and A5b are prepared from compounds A2b and A1b respectively by methods known in the art.

Alternatively, compounds (Ib) can be prepared by reacting compounds A1b or A2b with compounds of formula B4 pNO$_2$—C$_6$H$_4$—C(O)—O—CH$_2$—(CH$_2$)$_m$—[O—(CH$_2$)$_n$]$_p$—(CH—ONO$_2$)$_q$—CH$_2$—ONO$_2$  B4 wherein m, p, q, and n are as previously defined in the presence of an organic or inorganic base such as DMAP, TEA, DIPEA, with or without a catalyst such as Sc(OTf)$_3$ in an aprotic polar/apolar solvent such as THF, DMF CH$_2$Cl$_2$ at temperatures ranging between −20° C. to 100° C., following methods being well known in the literature.

Compounds of formula B4, are prepared from compounds B3 by methods known in the art.

Glossary

ACN: Acetonitrile
AC$_2$O: Acetic anhydride
DCC: Dicyclohexylcarbodiimide
DCM: Dichloromethane
DIPEA: N,N-Diisopropylethylamine
DMF: N, N-dimetilformamide
DMSO: Dimethyl sulfoxide
DMAP: 4-Dimethylaminopyridine
EtOAc: Ethyl Acetate
Et$_2$O: Ethyl ether
EtOH: Ethanol
iPrOH: Isopropanol
NBS: N-bromosuccinimide
MTBE: Methyl tert-Butyl ether
TEA: Triethylamine
TEMPO: 2,2,6,6-Tetramethylpiperidin-1-oxyl
THF: Tetrahydrofuran
PhP$_3$: Triphenyl phosphine

EXAMPLE 1

(S)-(1-(4-(3-chloro-4-methoxybenzylamino)-5-(pyrimidin-2-ylmethylcarbamoyl) pyrimidin-2-yl)pyrrolidin-2-yl)methyl 6-(nitrooxy)hexanoate (Compound (9))

(9)

To a solution of avanafil (1.00 g, 2.07 mmol) in dry DCM (15 ml), DMAP (252 mg, 2.07 mmol), DCC (512 mg, 2.48 mmol) and 6-(nitrooxy)hexanoic acid (440 mg, 2.48 mmol) were added.

The mixture was stirred overnight at room temperature and then diluted with DCM and water. The two phases were separated and the aqueous layer was extracted twice with DCM. The combined organic extracts were dried over MgSO$_4$ and concentrated under reduced pressure. The residue was purified by reversed-phase chromatography (H$_2$O/CH$_3$CN with 0.1% formic acid, from 70:30 to 40:60).

The residue was taken up in DCM and this solution was washed with an aqueous saturated solution of NaHCO$_3$. Then, the aqueous layer was extracted twice with DCM. The combined organic phases were dried over MgSO$_4$ and concentrated under reduced pressure, giving 1.23 g of the desired product (Compound (9)) (yield: 93.0%).

$^1$H NMR (400 MHz, DMSO-d$_6$) δ 9.19 (s, 1H), 8.81 (m, 1H), 8.75 (d, J=4.9 Hz, 2H), 8.54 (m, 1H), 7.50-7.14 (m, 3H), 7.06 (s, 1H), 4.54 (m, 4H), 4.37-3.90 (m, 3H), 3.81 (s, 3H), 3.59-3.39 (m, 4H), 2.32 (t, J=7.1 Hz, 2H), 2.09-1.73 (m, 4H), 1.66-1.52 (m, 4H), 1.32 (dt, J=5.2, 7.5 Hz, 2H).

EXAMPLE 2

[(2S)-1-(4-{[(3-chloro-4-methoxyphenyl)methyl]amino}-5-{[(pyrimidin-2-yl)methyl]carbamoyl}pyrimidin-2-yl)pyrrolidin-2-yl]methyl (5S)-5,6-bis(nitrooxy)hexanoate (Compound (10)-(5S)-isomer)

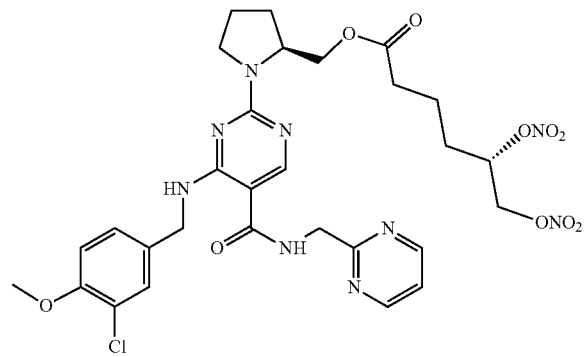

(10)-(5S)

To a solution of Avanafil (120 mg, 0.248 mmol) in dry DCM (1.5 ml), DMAP (30 mg, 0.248 mmol), DCC (56 mg, 0.273 mmol) and (5S)-5,6-bis(nitrooxy)hexanoic acid (65 mg, 0.273 mmol) were added.

The mixture was stirred overnight at room temperature, then diluted with DCM and water. The two phases were separated and the aqueous phase extracted twice with DCM. The combined organic phases were dried over MgSO$_4$ and concentrated under reduced pressure. The residue was purified by reversed-phase chromatography (H$_2$O/CH$_3$CN with 0.01% Formic acid, from 70:30 to 40:60).

After purification DCM and a saturated solution of NaHCO$_3$ were added to the residue. The two phases were separated and the aqueous phase extracted twice with DCM. The combined organic phases were dried over MgSO$_4$ and concentrated under reduced pressure, giving 165 mg of the desired product (Compound (10)-(5S)-isomer) (yield: 94.5%).

$^1$H NMR (400 MHz, DMSO-d$_6$) δ 9.16 (t, J=6.0 Hz, 1H), 8.79 (m, 1H), 8.75 (d, J=4.9 Hz, 2H), 8.54 (s, 1H), 7.38 (t, J=4.9 Hz, 1H), 7.34-7.23 (m, 1H), 7.19 (d, J=7.4 Hz, 1H), 7.05 (t, J=9.8 Hz, 1H), 5.41 (m, 1H), 4.91 (m, 1H), 4.71 (m, 1H), 4.54 (m, 4H), 4.16 (m, 3H), 3.98 (s, 3H), 3.50 (m, 2H), 2.38 (t, J=6.7 Hz, 2H), 1.92 (m, 4H), 1.79-1.51 (m, 4H).

EXAMPLE 3

(S)-(1-(4-(3-chloro-4-methoxybenzylamino)-5-(pyrimidin-2-ylmethylcarbamoyl) pyrimidin-2-yl)pyrrolidin-2-yl)methyl 2-(2-(nitrooxy)ethoxy) acetate (Compound (11))

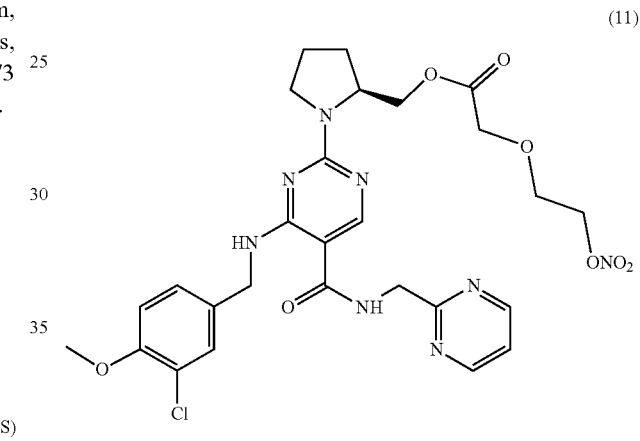

(11)

To a solution of Avanafil (160 mg, 0.331 mmol) in dry DCM (1.5 ml), DMAP (40 mg, 0.327 mmol), DCC (82 mg, 0.397 mmol) and 2-(2-(nitrooxy)ethoxy)acetic acid (82 mg, 0.497 mmol) were added.

The mixture was stirred over weekend at room temperature and then diluted with DCM and water. The two phases were separated and the aqueous phase extracted twice with DCM. The combined organic phases were dried over MgSO$_4$ and concentrated under reduced pressure. The residue was purified by reversed-phase chromatography (H$_2$O/CH$_3$CN with 0.01% formic acid, from 90:10 to 65:35).

After purification DCM and a saturated solution of NaHCO$_3$ were added to the residue. The two phases were separated and the aqueous phase extracted twice with DCM. The combined organic phases were dried over MgSO$_4$ and concentrated under reduced pressure, giving 109 mg of the desired product (Compound (11)) (yield: 52%).

$^1$H NMR (400 MHz, DMSO-d$_6$) δ 9.16 (t, J=6.0 Hz, 1H), 8.79 (s, 1H), 8.75 (d, J=4.9 Hz, 2H), 8.54 (s, 1H), 7.38 (t, J=4.9 Hz, 1H), 7.24 (m, 1H), 7.06 (s, 1H), 4.70 (m, 2H), 4.54 (m, 4H), 4.26 (dd, J=10.5, 3.4 Hz, 1H), 4.18 (s, 2H), 3.80 (s, 3H), 3.78 (m, 2H), 3.50 (m, 2H), 2.02-1.79 (m, 4H).

EXAMPLE 4

[(2S)-1-(4-{[(3-chloro-4-methoxyphenyl)methyl]amino}-5-{[(pyrimidin-2-yl)methyl]carbamoyl}pyrimidin-2-yl)pyrrolidin-2-yl]methyl 3-[(2S)-2,3-bis(nitrooxy)propoxy]propanoate (Compound (12)-(2S)-isomer)

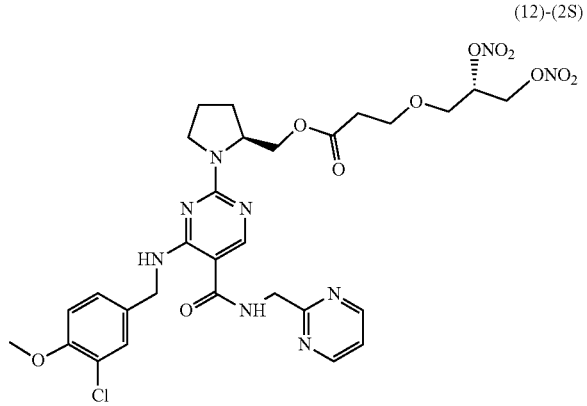

(12)-(2S)

To a solution of Avanafil (160 mg, 0.331 mmol) and 4-nitrophenyl 3-[(2S)-2,3-bis(nitrooxy)propoxy]propanoate (82 mg, 0.497 mmol) in dry DCM (1.5 ml), DMAP (40 mg, 0.327 mmol) was added.

The mixture was stirred over weekend at room temperature, then diluted with DCM and water. The two phases were separated and the aqueous phase extracted twice with DCM. The combined organic phases were dried over $MgSO_4$ and concentrated under reduced pressure. The residue was purified by reversed-phase chromatography ($H_2O/CH_3CN$ with 0.01% formic acid, from 85:15 to 55:45).

After purification DCM and a saturated solution of $NaHCO_3$ were added to the residue. The two phases were separated and the aqueous phase extracted twice with DCM. The combined organic phases were dried over $MgSO_4$ and concentrated under reduced pressure, giving 227 mg of the desired product (Compound (12)-(2S)-isomer) (yield: 95.0%).

$^1$H NMR (400 MHz, DMSO-$d_6$) δ 9.16 (t, J=6.0 Hz, 1H), 8.78 (s, 1H), 8.75 (d, J=4.9 Hz, 1H), 8.53 (s, 1H), 7.38 (t, J=4.9 Hz, 1H), 7.34-7.16 (m, 1H), 7.05 (t, J=9.4 Hz, 1H), 5.55 (q, 1H), 4.89 (d, J=12.9 Hz, 1H), 4.75 (m, 1H), 4.54 (m, 4H), 4.41-3.93 (m, 3H), 3.80 (s, 3H), 3.78-3.63 (m, 4H), 3.51 (m, 2H), 2.57 (t, J=6.1 Hz, 2H), 1.92 (m, 4H).

Synthesis of 4-nitrophenyl 3-[(2S)-2,3-bis(nitrooxy)propoxy]propanoate

Step 1: Synthesis of (S)-4-(allyloxymethyl)-2,2-dimethyl-1,3-dioxolane

NaH (60%) (3.4 g; 85.54 mmol) was suspended in dry THF (140 ml) together with S(+)-1,2-isopropylidenglycerol (5.65 g; 42.75 mmol) and 15-Crown-5 (0.9 g; 4.28 mmol).

The mixture was cooled to 0° C. and allyl bromide (7.2 ml; 85.54 mmol) was added dropwise. The suspension was stirred for 6 h at rt, than $NH_4Cl$ saturated solution (100 ml) was added dropwise at 0° C. and then the mixture extracted with $Et_2O$ (3×100 ml). The combined organic layers were washed once with brine and concentrated under reduced pressure carefully. The residue was purified by flash chromatography (Biotage SP4 instrument, SNAP 100 column, isocratic elution $Et_2O$/Cyclohexane 1:9), affording 5.8 g, (yield 78.5%) of the title compound ((S)-4-(allyloxymethyl)-2,2-dimethyl-1,3-dioxolane).

$^1$HNMR (300 MHz, Chloroform-d) δ 6.00-5.78 (m, 1H), 5.35-5.13 (m, 2H), 4.35-4.21 (m, 1H), 4.11-3.98 (m, 3H), 3.73 (m, 1H), 3.57-3.40 (m, 2H), 1.51-1.32 (m, 6H).

Step 2: Synthesis of (S)-3-((2,2-dimethyl-1,3-dioxolan-4-yl)methoxy)propan-1-ol To a stirred solution of (S)-4-(allyloxymethyl)-2,2-dimethyl-1,3-dioxolane (2.0 g, 10.64 mmol) in dry THF (180 ml) cooled at 0° C., 9BBN 0.5M (241.8 ml, 121 mmol) was added dropwise. The reaction was stirred 30 minutes at 0° C. and overnight at room temperature. The reaction mixture was cooled at 0° C. and NaOH 2N (84 ml) was added together with $H_2O_2$ 30% (58 ml). The mixture was diluted with $Et_2O$ (100 ml) and NaOH 1N (100 ml). The 2 phases were separated and aqueous layer was extracted with $Et_2O$ (3×120 ml). The combined organic layers were washed once with brine, dried over $Na_2SO_4$ and concentrated under reduced pressure. The residue was purified by flash chromatography (Biotage SP4 instrument, SNAP 100 column, EtOAC in cyclohexane, from 30% to 80% in 10 c.v. affording 6.4 g (yield: 100%) of the title compound ((S)-3-((2,2-dimethyl-1,3-dioxolan-4-yl)methoxy)propan-1-ol).

$^1$HNMR (300 MHz, Chloroform-d) δ 4.35-4.20 (m, 1H), 4.11-4.01 (m, 1H), 3.85-3.63 (m, 5H), 3.58-3.46 (m, 2H), 1.97-1.80 (m, 2H), 1.45 (s, 3H), 1.38 (s, 3H).

Step 3: Synthesis of (S)-3-((2,2-dimethyl-1,3-dioxolan-4-yl)methoxy)propanoic Acid To a solution of (S)-3-((2,2-dimethyl-1,3-dioxolan-4-yl)methoxy)propan-1-ol (2.03 g; 10.51 mmol) in acetone (50 ml) cooled at 0° C., $NaHCO_3$ sat solution (56 ml), NaBr (0.45 g, 4.20 mmol) and TEMPO (0.34 g, 2.10 mmol) were added. Trichloroisocyanuric acid (4.91 g, 21.02 mmol) was then added portionwise. The mixture was allowed to reach room temperature and stirred for 3 h. The mixture was then cooled at 0° C. and isopropanol (20 ml) was added slowly. The mixture was stirred at 0° C. 30 minutes. The formation of a white solid was observed. The precipitate was filtered off and the solvent concentrated. NaOH 2N was added to the residue (pH=12) and the aqueous solution was washed twice with EtOAc. To the aqueous phase HCl 1N was added until pH 2-3 and it was extracted with EtOAc (5×50 ml). The combined organic phases were dried over $Na_2SO_4$ and then evaporated affording 0.82 g (Yield: 38%) of the title compound ((S)-3-((2,2-dimethyl-1,3-dioxolan-4-yl)methoxy)propanoic acid).

$^1$HNMR (300 MHz, Chloroform-d) δ 4.34-4.16 (m, 1H), 4.11-3.97 (m, 1H), 3.85-3.68 (m, 3H), 3.63-3.42 (m, 2H), 2.74-2.55 (m, 2H), 1.41 (s, 3H), 1.35 (s, 3H).

Step 4: Synthesis of (S)-4-nitrophenyl 3-((2,2-dimethyl-1,3-dioxolan-4-yl)methoxy) propanoate To a solution of (S)-3-((2,2-dimethyl-1,3-dioxolan-4-yl)methoxy)propanoic acid (0.82 g, 4.02 mmol), DCC (0.83 mg, 4.02 mmol) and DMAP (0.1 g, 0.80 mmol) in DCM (15 ml), 4-nitrophenol (0.56 g; 4.02 mmol) was added portionwise. The mixture was stirred overnight at room temperature, then the precipitate was filtered off and the solvent evaporated. The residue was purified by flash chromatography (Biotage SP4 instrument, EtOAc in cyclohexane from 5% to 50% in 12 CV) affording 0.97 g of the title compound ((S)-4-nitrophenyl 3-((2,2-dimethyl-1,3-dioxolan-4-yl)methoxy) propanoate) (Yield: 74%).

$^1$H NMR (300 MHz, Chloroform-d) δ 8.33-8.21 (m, 2H), 7.37-7.20 (m, 2H), 4.37-4.20 (m, 1H), 4.09-4.00 (m, 1H), 3.96-3.84 (m, 2H), 3.80-3.66 (m, 1H), 3.63-3.47 (m, 2H), 2.96-2.78 (m, 2H), 1.42 (s, 3H), 1.36 (s, 3H).

Step 5: Synthesis of (R)-4-nitrophenyl 3-(2,3-dihydroxypropoxy) propanoate

To a stirred solution of (S)-4-nitrophenyl 3-((2,2-dimethyl-1,3-dioxolan-4-yl)methoxy) propanoate (0.97 g, 2.97 mmol) in THF (10 ml), HCl 3N (2 ml) was added and the solution stirred for 4 h at room temperature. Then EtOAc (5 ml) and H$_2$O (5 ml) were added and the two phases were separated. The aqueous phase was extracted with EtOAc (2×5 ml). The combined organic layers were washed with brine, dried over Na$_2$SO$_4$ and concentrated under reduced pressure affording 0.89 g of the title compound ((R)-4-nitrophenyl 3-(2,3-dihydroxypropoxy) propanoate), which was used in the next step without further purification.

Step 6: Synthesis of 4-nitrophenyl 3-[(2S)-2,3-bis(nitrooxy)propoxy]propanoate To a solution of Ac$_2$O (0.76 ml, 8.07 mmol) in DCM (5 ml) at −40° C., fuming HNO3 (0.38 ml, 9.32 mmol) was added dropwise. A solution of (R)-4-nitrophenyl 3-(2,3-dihydroxypropoxy) propanoate (0.89 g, 3.11 mmol) in DCM (7 ml) was then added dropwise. The mixture was allowed to reach 0° C. and stirred for 4 hours. The mixture was then poured into ice and NaHCO$_3$ was added portionwise. The two phases were separated and the aqueous phase washed twice with DCM. The combined organic phases were dried over Na$_2$SO$_4$ and concentrated affording 0.56 g of the title compound (4-nitrophenyl 3-[(2S)-2,3-bis(nitrooxy)propoxy]propanoate) (yield of two steps: 38%).

$^1$H NMR (300 MHz, Chloroform-d) δ 8.35-8.22 (m, 2H), 7.35-7.22 (m, 2H), 5.48-5.34 (m, 1H), 4.88-4.73 (m, 1H), 4.73-4.56 (m, 1H), 3.94-3.85 (m, 2H), 3.85-3.77 (m, 2H), 2.88 (t, 2H).

Synthesis of 3-[(2S)-2,3-bis(nitrooxy)propoxy]propanoic Acid (Compound (IIIg)-OH)

A solution of 4-nitrophenyl 3-[(2S)-2,3-bis(nitrooxy)propoxy]propanoate (Step 6) (500 mg, 1.33 mmol) in 5 ml of a 1/1 (vol/vol) mixture of EtOH/THF was cooled to 0° C. Then 1.33 ml (2.66 mmol) of 2N NaOH solution was dropwise added to the stirred solution in 45 minutes.

The mixture was left under stirring for 1 h. Then the organic solvents were removed under vacuum and EtOAc (25 ml) and water (25 ml) were added. The organic phase was removed and the pH of the aqueous phase was set to 1 using HCl 2N. The aqueous phase was extracted with DCM (2×15 ml) dried over sodium sulfate and evaporated under vacuum.

The obtained raw product was purified on a 4 g 25µ C18 cartridge using a gradient of (ACN)/(H$_2$O+0.1% HCOOH) from 5/95 to 30/70 over 30 minutes.

The fractions containing clean product were pooled and lyophilized to give 210 mg of the title compound (3-[(2S)-2,3-bis(nitrooxy)propoxy]propanoic acid as a clear oil) (yield 61%).

$^1$H NMR (400 MHz, DMSO-d$_6$) δ ppm 2.43-2.48 (m, 2H) 3.61-3.78 (m, 4H) 4.76 (dd, J=12.89, 6.54 Hz, 1H) 4.92 (dd, J=12.89, 2.93 Hz, 1H) 5.54-5.59 (m, 1H) 12.23 (br s, 1H)

EXAMPLE 5

(S)-(1-(4-(3-chloro-4-methoxybenzylamino)-5-(pyrimidin-2-ylmethylcarbamoyl) pyrimidin-2-yl)pyrrolidin-2-yl)methyl 6-(nitrooxy)hexanoate 2-hydroxypropane-1,2,3-tricarboxylate (Compound (9) Citrate Salt)

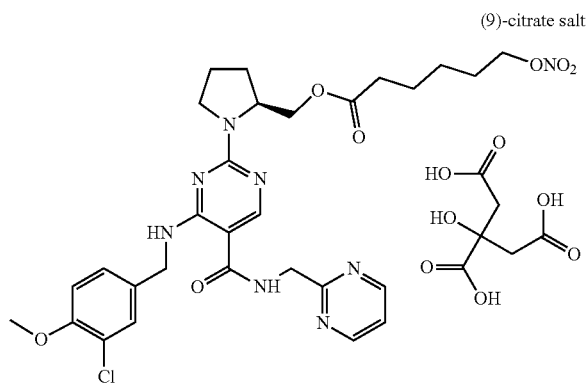

(9)-citrate salt

To a solution of compound (9), prepared as described in Example 1, (100 mg, 0.155 mmol) in Methanol (1.5 ml), citric acid monohydrate (33 mg, 0.155 mmol) was added. The mixture was stirred for 10 minutes at room temperature, then concentrated and the solid washed with MTBE. The solid was filtered and dried under reduced pressure, giving 125 mg of the desired product (Compound (9) citrate salt) (crude yield: 96.6%).

$^1$H NMR (600 MHz, DMSO-d6) δ 12.39-12.36 (m, 3H), 9.19 (s, 1H), 8.80 (m, 1H), 8.75 (d, J=4.9 Hz, 2H), 8.53 (m, 1H)), 7.42-7.15 (m, 3H), 7.06 (m, 1H), 4.65-4.38 (m, 6H), 4.37-4.11 (m, 3H), 3.80 (s, 3H) 3.59-3.39 (m, 2H), 2.75 (d, J=15.4 Hz, 2H), 2.65 (d, J=15.4 Hz, 2H), 2.32 (m, 2H), 2.05-1.80 (m, 4H), 1.47-1.08 (m, 4H), 1.32 (q, 2H)

EXAMPLE 6

((S)-1-(4-(3-chloro-4-methoxybenzylamino)-5-(pyrimidin-2-ylmethylcarbamoyl) pyrimidin-2-yl)pyrrolidin-2-yl)methyl (5S)-5,6-bis(nitrooxy) hexanoate 2-hydroxypropane-1,2,3-tricarboxylate (Compound (10)-(5S)-isomer, Citrate Salt)

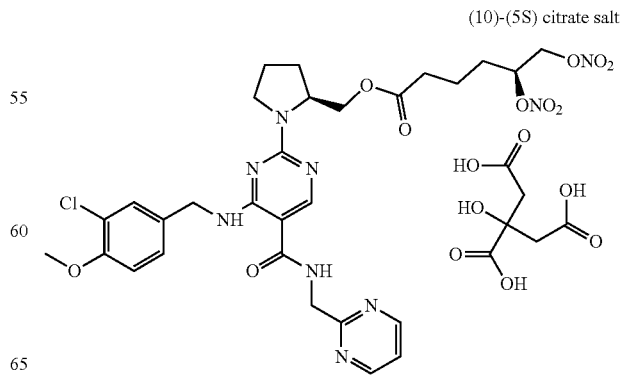

(10)-(5S) citrate salt

To a solution of Compound (10)-(5S)-isomer, prepared as described in Example 2, (165 mg, 0.234 mmol) in Methanol (1.5 ml), citric acid monohydrate (49 mg, 0.233 mmol) was added. The mixture was stirred for 10 minutes at room temperature, then concentrated and the residue was washed with diethyl ether. The solid was filtered and dried under reduced pressure, giving 205 mg of the desired product (Compound (10)-(5S)-isomer-citrate salt) (crude yield: 97.8%).

$^1$H NMR (600 MHz, DMSO-d6) δ 12.37 (s, 3H), 9.18 (s, 1H), 8.85-8.70 (m, 3H), 8.53 (m, 1H), 7.42-7.36 (m, 2H), 7.34-7.15 (m, 1H), 7.10-7.01 (m, 1H), 5.41 (m, 1H), 4.91 (d, J=12.4 Hz, 1H), 4.70 (m, 1H), 4.63-4.42 (m, 4H), 4.38-3.92 (m, 3H), 3.81 (s, 3H), 3.51 (m, 2H), 2.75 (d, J=15.4 Hz, 2H), 2.66 (d, J=15.4 Hz, 2H), 2.38 (m, 2H), 1.92 (m, 4H), 1.79-1.58 (m, 4H).

EXAMPLE 7

(S)-(1-(4-(3-chloro-4-methoxybenzylamino)-5-(pyrimidin-2-ylmethylcarbamoyl) pyrimidin-2-yl)pyrrolidin-2-yl)methyl 2-(2-(nitrooxy)ethoxy) acetate 2-hydroxy propane-1,2,3-tricarboxylate (Compound (11) Citrate Salt)

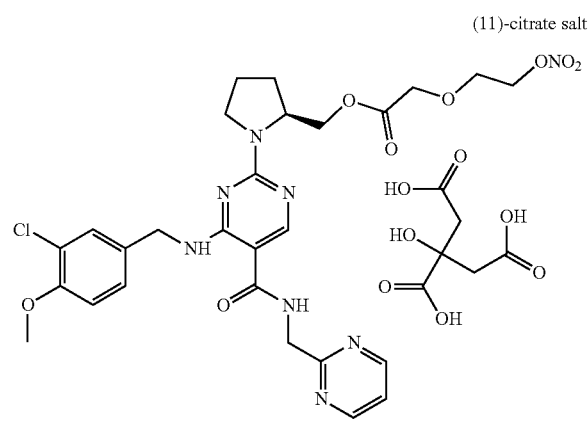

(11)-citrate salt

To a solution of Compound 11, prepared as described in Example 3, (109 mg, 0.173 mmol) in Methanol (1.0 ml), citric acid monohydrate (36 mg, 0.171 mmol) was added. The mixture was stirred for 10 minutes at room temperature, then concentrated and the residue was washed with diethyl ether. The solid was filtered and dried under reduced pressure, giving 139 mg of the desired product (Compound (11) citrate salt) (crude yield: 97.6%).

$^1$H NMR (600 MHz, DMSO-d6) δ 12.36 (s, 3H), 9.18 (s, 1H), 8.85-8.72 (m, 3H), 8.53 (m, 1H), 7.41-7.35 (m, 2H), 7.34-7.15 (m, 1H), 7.06 (m, 1H), 4.70-4.64 (m, 2H), 4.62-4.46 (m, 4H), 4.40-3.99 (m, 5H), 3.80 (s, 3H), 3.78 (m, 2H), 3.58-3.43 (m, 2H), 2.75 (d, J=15.4 Hz, 2H), 2.66 (d, J=15.4 Hz, 2H), 1.93 (m, 4H).

EXAMPLE 8

((S)-1-(4-(3-chloro-4-methoxybenzylamino)-5-(pyrimidin-2-ylmethylcarbamoyl) pyrimidin-2-yl)pyrrolidin-2-yl)methyl 3-((S)-2,3-bis(nitrooxy)propoxy) propanoate 2-hydroxypropane-1,2,3-tricarboxylate (Compound (12)-(2S)-isomer, Citrate Salt)

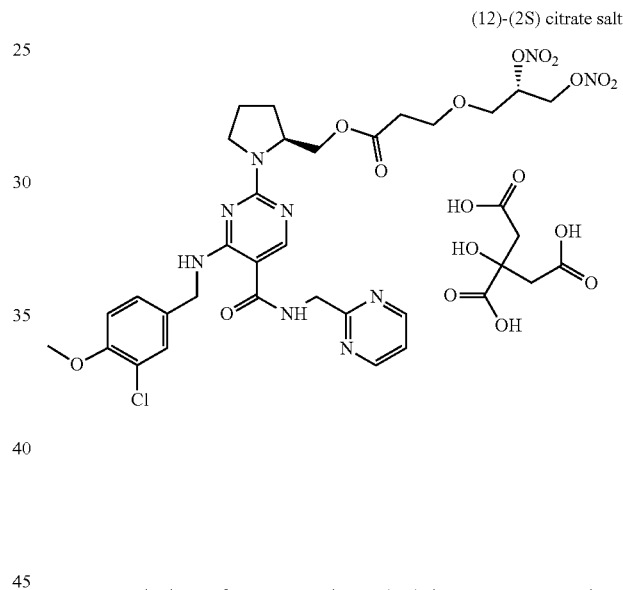

(12)-(2S) citrate salt

To a solution of compound 12, (2S)-isomer, prepared as described in Example 4 (227 mg, 0.315 mmol) in Methanol (2 ml), citric acid monohydrate (66 mg, 0.315 mmol) was added. The mixture was stirred for 10 minutes at room temperature, then concentrated and the residue was washed with diethyl ether. The solid was filtered and dried under reduced pressure, giving 280 mg of the desired product (Compound (12)-(2S)-isomer, citrate salt) (crude yield: 97.4%).

$^1$H NMR (600 MHz, DMSO-d6) δ 12.35 (s, 3H), 9.18 (s, 1H), 8.77 (m, 2H), 8.55 (m, 1H), 7.46-7.33 (m, 1H), 7.34-7.17 (m, 1H), 7.06 (dd, J=16.6, 8.3 Hz, 1H), 5.55 (s, 1H), 4.81 (m, 4H), 4.63-4.42 (m, 4H), 4.38-3.96 (m, 3H), 3.81 (s, 3H), 3.71 (m, 2H), 3.57-3.42 (m, 2H), 2.75 (d, J=15.4 Hz, 2H), 2.65 (d, J=15.4 Hz, 2H), 2.57 (t, J=5.9 Hz, 2H), 1.92 (m, 4H).

EXAMPLE 9

(S)-2-(4-(3-(5-ethyl-4-oxo-7-propyl-4,5-dihydro-3H-pyrrolo[3,2-d]pyrimidin-2-yl)-4-propoxyphenylsulfonyl)piperazin-1-yl)ethyl 3-[2,3-bis(nitrooxy)propoxy]propanoate citrate (Compound (1)-(2S)-isomer, Citrate Salt)

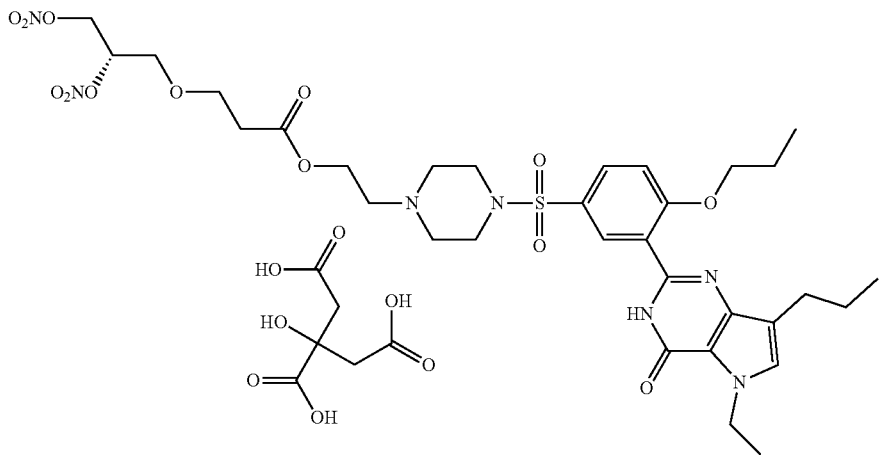

(1)-(2S) citrate salt

To a solution of Mirodenafil (500 mg, 0.940 mmol) and 4-nitrophenyl 3-[(2S)-2,3-bis(nitrooxy)propoxy]propanoate (see Example 4) (423 mg, 1.128 mmol) in dry DCM (5 ml), DMAP (115 mg, 0.940 mmol) was added.

The mixture was stirred at room temperature for 48 h, then it was diluted with DCM and water. The two phases were separated and the aqueous phase extracted twice with DCM. The combined organic phases were dried over MgSO$_4$ and concentrated under reduced pressure. The residue was purified by reversed-phase chromatography (H$_2$O/CH$_3$CN with 0.01% formic acid, from 70:30 to 20:80).

After purification DCM and a saturated solution of NaHCO$_3$ were added to the residue. The two phases were separated and the aqueous phase extracted twice with DCM. The combined organic phases were dried over MgSO$_4$ and concentrated under reduced pressure, giving 540 mg of (S)-2-(4-(3-(5-ethyl-4-oxo-7-propyl-4,5-dihydro-3H-pyrrolo[3,2-d]pyrimidin-2-yl)-4-propoxyphenylsulfonyl)piperazin-1-yl)ethyl 3-(3-nitro-2-(nitrooxy)propoxy)propanoate (compound (1), yield: 75.0%).

Compound (1) (295 mg, 0.384 mmol) was re-dissolved in Methanol (1.5 ml), and citric acid monohydrate (81 mg, 0.384 mmol) was added. The mixture was stirred for 10 minutes at room temperature, then concentrated and the solid washed with diethyl ether. The solid was filtered and dried under reduced pressure, giving 361 mg of the title compound (Compound (1)-(2S)-isomer, citrate salt) (crude yield: 98%).

$^1$H NMR (400 MHz, DMSO-d6) δ 2.30 (bs, 1H), 7.89 (d, J=2.4 Hz, 1H), 7.80 (dd, J=8.8, 2.5 Hz, 1H), 7.38 (d, J=8.9 Hz, 1H), 7.31 (s, 1H), 5.53 m, J=10.3, 6.7, 3.9 Hz, 1H), 4.88 (dd, J=12.8, 3.0 Hz, 1H), 4.72 (dd, J=12.9, 6.5 Hz, 1H), 4.37 (q, J=7.1 Hz, 2H), 4.10 (dt, J=11.4, 6.0 Hz, 4H), 3.77-3.58 (m, 4H), 2.90 (s, 4H), 2.75 (d, J=15.4 Hz, 2H), 2.65 (d, J=15.4 Hz, 2H), 2.61-2.52 (m, 10H), 1.80-1.58 (m, 4H), 1.36 (t, J=7.1 Hz, 3H), 0.97 (t, 3H), 0.94 (t, 3H).

EXAMPLE 10

2-(4-(3-(5-ethyl-4-oxo-7-propyl-4,5-dihydro-3H-pyrrolo[3,2-d]pyrimidin-2-yl)-4-propoxyphenylsulfonyl)piperazin-1-yl)ethyl 6-(nitrooxy)hexanoate citrate (Compound (4) Citrate Salt)

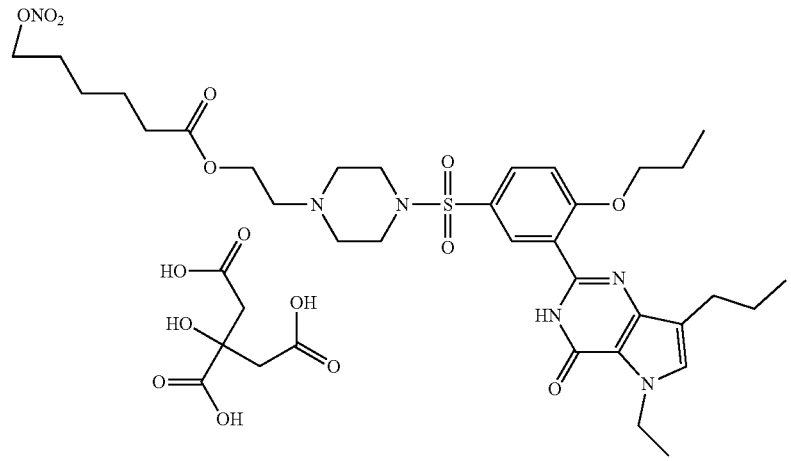

(4) citrate salt

To a solution of Mirodenafil (500 mg, 0.940 mmol) in dry DCM (5 ml), DMAP (115 mg, 0.940 mmol), DCC (233 mg, 1.128 mmol) and 6-(nitrooxy)hexanoic acid (200 mg, 1.128 mmol) were added.

The mixture was stirred overnight at room temperature and then diluted with DCM and water. The two phases were separated and the aqueous layer was extracted twice with DCM. The combined organic extracts were dried over MgSO₄ and concentrated under reduced pressure. The residue was purified by reversed-phase chromatography (H₂O/CH₃CN with 0.1% Formic acid, from 70:30 to 20:80).

After purification DCM and a saturated solution of NaHCO₃ were added to the residue. The two phases were separated and the aqueous phase extracted twice with DCM. The combined organic phases were dried over MgSO₄ and concentrated under reduced pressure, giving 450 mg of 2-(4-(3-(5-ethyl-4-oxo-7-propyl-4,5-dihydro-3H-pyrrolo[3,2-d]pyrimidin-2-yl)-4-propoxyphenylsulfonyl)piperazin-1-yl)ethyl 6-(nitrooxy)hexanoate (compound (4), yield: 69.0%).

To a solution of Compound (4) (200 mg, 0.290 mmol) in Methanol (1.5 ml), citric acid monohydrate (61 mg, 0.290 mmol) was added. The mixture was stirred for 10 minutes at room temperature, then concentrated and the solid washed with diethyl ether. The solid was filtered and dried under reduced pressure, giving 253 mg of the Title compound (Compound (4) citrate salt) (yield 98.8%).

¹H NMR (400 MHz, DMSO-d6) δ 11.67 (s, 1H), 7.90 (d, J=2.4 Hz, 1H), 7.80 (dd, J=8.8, 2.5 Hz, 1H), 7.38 (d, J=8.9 Hz, 1H), 7.31 (s, 1H), 4.47-4.32 (m, 4H), 4.09 (dt, J=11.3, 6.0 Hz, 4H), 2.90 (s, 4H), 2.75 (d, J=15.4 Hz, 2H), 2.65 (d, J=15.4 Hz, 2H), 2.55 (ddd, J=11.8, 8.4, 4.7 Hz, 8H), 2.26 (t, J=7.3 Hz, 2H), 1.81-1.69 (m, 2H), 1.69-1.55 (m, 4H), 1.50 (m, 2H), 1.39-1.33 (m, 3H), 1.29 (q, 2H), 0.94 (m, 6H).

EXAMPLE 11

2-hydroxypropane-1,2,3-tricarboxylic acid 2-{4-[3-(5-ethyl-4-oxo-7-propyl-4,5-dihydro-3H-pyrrolo[3,2-d]pyrimidin-2-yl)-4-propoxybenzene-1-sulfonyl]piperazin-1-yl}ethyl [2-(nitrooxy)ethoxy]acetate (Compound (2) Citrate Salt)

To a solution of Mirodenafil (500 mg, 0.940 mmol) in dry DCM (5 ml), DMAP (115 mg, 0.940 mmol), DCC (233 mg, 1.128 mmol) and [2-(nitrooxy)ethoxy]acetic acid (186 mg, 1.128 mmol) were added.

The mixture was stirred at room temperature for 48 h then it was diluted with DCM and water. The two phases were separated and the aqueous phase extracted twice with DCM. The combined organic phases were dried over MgSO₄ and concentrated under reduced pressure. The residue was purified by reversed-phase chromatography (H₂O/CH₃CN with 0.1% formic acid, from 70:30 to 40:60).

After purification DCM and a saturated solution of NaHCO₃ were added to the residue. The two phases were separated and the aqueous phase extracted twice with DCM. The combined organic phases were dried over MgSO₄ and concentrated under reduced pressure, giving 338 mg of 2-{4-[3-(5-ethyl-4-oxo-7-propyl-4,5-dihydro-3H-pyrrolo[3,2-d]pyrimidin-2-yl)-4-propoxybenzene-1-sulfonyl]piperazin-1-yl}ethyl [2-(nitrooxy)ethoxy]acetate (compound (2), yield: 53.0%).

To a solution of Compound (2) (172 mg, 0.253 mmol) in Methanol (1.5 ml), citric acid monohydrate (53 mg, 0.276 mmol) was added. The mixture was stirred 10 minutes at room temperature, then concentrated and the solid washed with diethyl ether. The solid was filtered and dried under reduced pressure, giving 220 mg of the title compound (Compound (2) citrate salt) (crude yield: 99.8%).

¹H NMR (400 MHz, DMSO-d6) δ 11.68 (s, 1H), 7.90 (t, J=5.8 Hz, 1H), 7.80 (m, 1H), 7.38 (d, J=8.9 Hz, 1H), 7.31 (s, 1H), 4.67-4.59 (m, 2H), 4.45-4.27 (m, 2H), 4.20-4.04 (m, 6H), 3.78-3.71 (q, 2H), 2.90 (s, 4H), 2.75 (t, J=15.4 Hz, 2H), 2.65 (t, J=15.4 Hz, 2H), 2.61-2.52 (m, 8H), 1.81-1.55 (m, 4H), 1.36 (t, J=7.1 Hz, 3H), 0.94 (t, 6H).

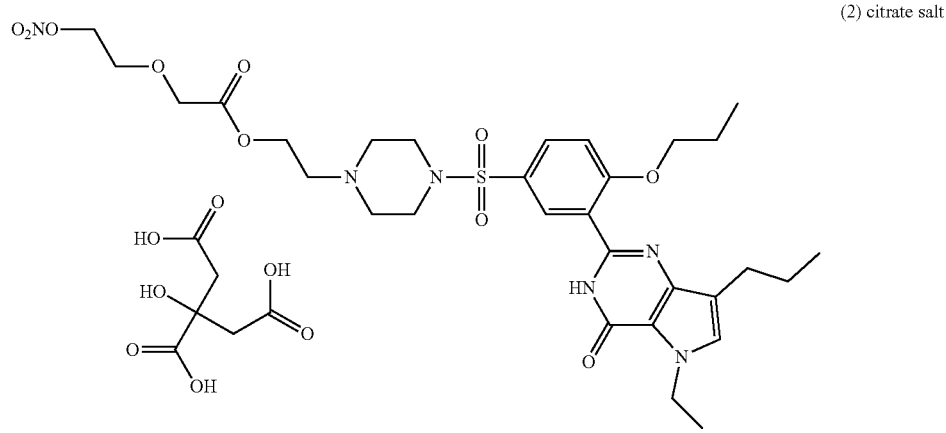

(2) citrate salt

EXAMPLE 12

(S)-2-(4-(3-(5-ethyl-4-oxo-7-propyl-4,5-dihydro-3H-pyrrolo[3,2-d]pyrimidin-2-yl)-4-propoxyphenylsulfonyl)piperazin-1-yl)ethyl 5,6-bis(nitrooxy) hexanoate Citrate (Compound (3)-(5S) Isomer, Citrate Salt)

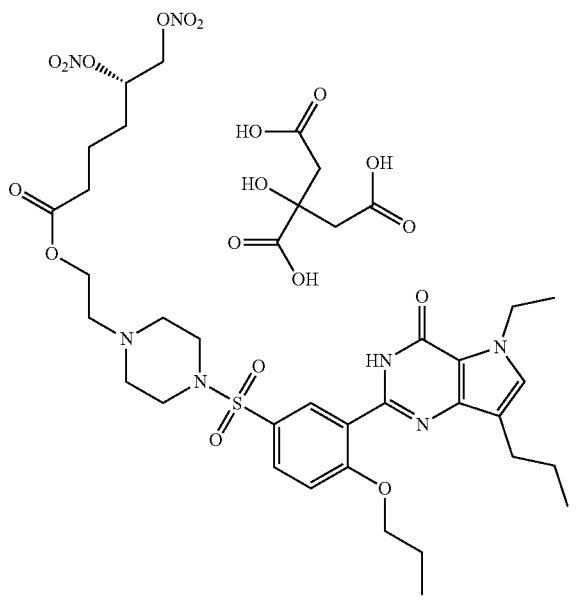

(3)-(5S) citrate salt

To a solution of Mirodenafil (500 mg, 0.940 mmol) in dry DCM (5 ml), DMAP (115 mg, 0.940 mmol), DCC (233 mg, 1.128 mmol) and (5S)-5,6-bis(nitrooxy)hexanoic acid (270 mg, 1.128 mmol) were added.

The mixture was stirred overnight at room temperature, then diluted with DCM and water. The two phases were separated and the aqueous phase extracted twice with DCM. The combined organic phases were dried over $MgSO_4$ and concentrated under reduced pressure. The residue was purified by reversed-phase chromatography ($H_2O/CH_3CN$ with 0.1% formic acid, from 70:30 to 40:60).

After purification DCM and a saturated solution of $NaHCO_3$ were added to the residue. The two phases were separated and the aqueous phase extracted twice with DCM. The combined organic phases were dried over $MgSO_4$ and concentrated under reduced pressure, giving 550 mg of (S)-2-(4-(3-(5-ethyl-4-oxo-7-propyl-4,5-dihydro-3H-pyrrolo[3,2-d]pyrimidin-2-yl)-4-propoxyphenylsulfonyl)piperazin-1-yl)ethyl 5,6-bis(nitrooxy)hexanoate (Compound (3), yield: 77.8%).

To a solution of Compound (3) (207 mg, 0.275 mmol) in Methanol (1.5 ml), citric acid monohydrate (58 mg, 0.302 mmol) was added. The mixture was stirred for 10 minutes at room temperature, then concentrated and the solid washed with diethyl ether. The solid was filtered and dried under reduced pressure, giving 254 mg of the title compound (Compound (3)-(5S) isomer, citrate salt) (yield: 97.8%).

$^1$H NMR (400 MHz, DMSO-d6) δ 11.67 (s, 1H), 7.89 (d, J=2.4 Hz, 1H), 7.80 (dd, J=8.8, 2.5 Hz, 1H), 7.38 (d, J=8.9 Hz, 1H), 7.31 (s, 1H), 5.38 (m, J=13.1, 5.9, 2.6 Hz, 1H), 4.89 (dd, J=12.9, 2.6 Hz, 2H), 4.70 (m, 2H), 4.37 (q, J=7.1 Hz, 2H), 4.09 (dt, J=11.3, 6.0 Hz, 4H), 2.90 (s, 4H), 2.75 (t, 2H), 2.65 (d, J=15.4 Hz, 2H), 2.61-2.52 (m, 8H), 2.32 (t, J=7.1 Hz, 2H), 1.82-1.55 (m, 8H), 1.36 (t, J=7.1 Hz, 3H), 0.94 (t, 6H).

EXAMPLE 13

2-(4-(3-(5-ethyl-4-oxo-7-propyl-4,5-dihydro-3H-pyrrolo[3,2-d]pyrimidin-2-yl)-4-propoxyphenylsulfonyl)piperazin-1-yl)ethyl 6-(nitrooxy)hexyl Carbonate (Compound (5))

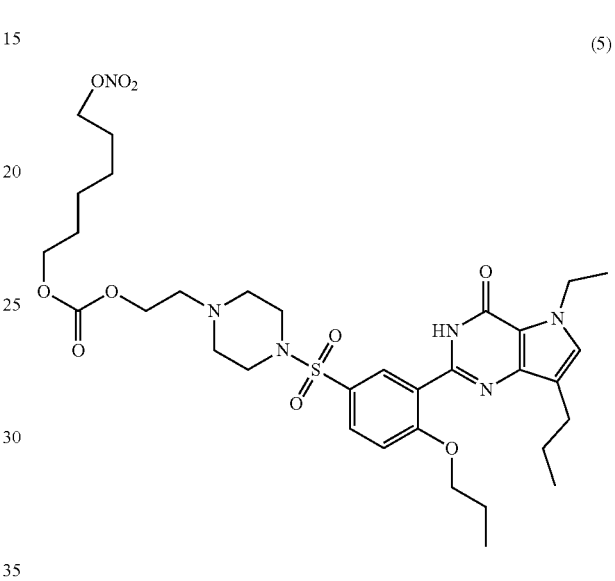

(5)

Step 1: 2-(4-((3-(5-ethyl-4-oxo-7-propyl-4,5-dihydro-3H-pyrrolo[3,2-d]pyrimidin-2-yl)-4-propoxyphenyl)sulfonyl)piperazin-1-yl)ethyl (4-nitrophenyl) Carbonate To a solution of Mirodenafil (290 mg, 0.545 mmol) in dry DCM (5 ml), 4-Nitrophenyl chloroformate (121 mg, 0.600 mmol) and DMAP (74 mg, 0.600 mmol) were added. The mixture was stirred overnight at room temperature, then it was diluted with DCM and water. The two phases were separated and the aqueous phase extracted twice with DCM. The combined organic phases were dried over $MgSO_4$ and concentrated under reduced pressure. The residue was purified by flash chromatography (Cyclohexane:EtOAc:MeOH 5:5:0.1%). Then the fraction was collected and dried under reduced pressure, affording 310 mg of the title compound (2-(4-((3-(5-ethyl-4-oxo-7-propyl-4,5-dihydro-3H-pyrrolo [3,2-d]pyrimidin-2-yl)-4-propoxyphenyl)sulfonyl) piperazin-1-yl)ethyl (4-nitrophenyl) carbonate) (yield: 81.7%) as a colorless oil.

Step 2: 2-(4-(3-(5-ethyl-4-oxo-7-propyl-4,5-dihydro-3H-pyrrolo[3,2-d]pyrimidin-2-yl)-4-propoxyphenylsulfonyl)piperazin-1-yl)ethyl 6-(nitrooxy) hexyl Carbonate To a solution of 2-(4-((3-(5-ethyl-4-oxo-7-propyl-4,5-dihydro-3H-pyrrolo[3,2-d]pyrimidin-2-yl)-4-propoxyphenyl) sulfonyl)piperazin-1-yl)ethyl (4-nitrophenyl) carbonate (150 mg, 0.21 mmol)) in dry DCM (1 ml), DMAP (30 mg, 0.24 mmol) and 6-hydroxyhexyl nitrate (39 mg, 0.24 mmol)

were added. The mixture was stirred overnight at room temperature, then it was diluted with DCM and water. The two phases were separated and the aqueous phase extracted twice with DCM. The combined organic phases were dried over MgSO$_4$ and concentrated under reduced pressure. The residue was purified by reversed-phase chromatography (H$_2$O/CH$_3$CN with 0.1% formic acid, from 90:10 to 20:80). Dichloromethane and a saturated solution of NaHCO$_3$ were added to the residue after purification. The two phases were separated and the aqueous phase extracted twice with DCM. Then the fraction was collected and dried under reduced pressure, affording 150 mg of the title compound (Compound (5)) (yield: 97%) as a sticky oil.

$^1$H NMR (600 MHz, DMSO-d6) δ 11.65 (s, 1H), 7.89 (d, J=2.4 Hz, 1H), 7.80 (dd, J=8.8, 2.4 Hz, 1H), 7.38 (d, J=8.9 Hz, 1H), 7.31 (s, 1H), 4.47 (t, J=6.6 Hz, 2H), 4.37 (q, J=7.1 Hz, 2H), 4.13 (t, J=5.9 Hz, 2H), 4.00 (t, J=6.6 Hz, 2H), 2.88 (t, 2H), 2.60-2.51 (m, 8H), 1.79-1.70 (m, 2H), 1.68-1.57 (m, 4H), 1.56-1.48 (m, 2H), 1.36 (t, J=7.2 Hz, 3H), 1.33-1.22 (m, 4H), 0.97 (t, J=7.4 Hz, 3H), 0.92 (t, J=7.3 Hz, 3H).

EXAMPLE 14

(S)-5,6-bis (nitrooxy)hexyl 2-(4-(3-(5-ethyl-4-oxo-7-propyl-4,5-dihydro-3H-pyrrolo [3,2-d]pyrimidin-2-yl)-4-propoxyphenylsulfonyl)piperazin-1-yl)ethyl Carbonate (Compound (6))

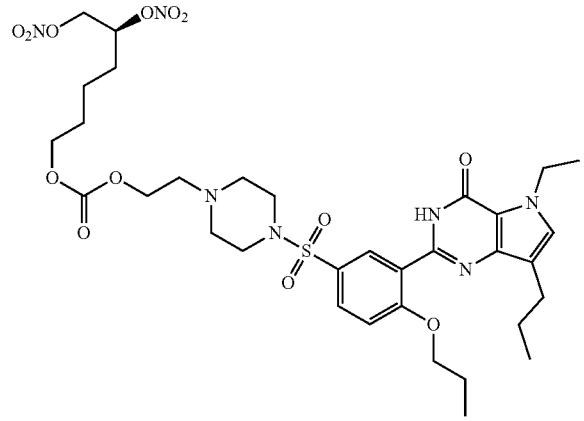

(6)

To a solution of 2-(4-((3-(5-ethyl-4-oxo-7-propyl-4,5-dihydro-3H-pyrrolo[3,2-d]pyrimidin-2-yl)-4-propoxyphenyl)sulfonyl)piperazin-1-yl)ethyl (4-nitrophenyl) carbonate, prepared as described in Example 13, Step 1 (200 mg, 0.29 mmol)) in dry DCM (2 ml), DMAP (39 mg, 0.32 mmol) and 6-hydroxyhexane-1,2-diyl dinitrate (72 mg, 0.32 mmol) were added.

The mixture was stirred overnight at room temperature then it was diluted with DCM and water. The two phases were separated and the aqueous phase extracted twice with DCM. The combined organic phases were dried over MgSO$_4$ and concentrated under reduced pressure. The residue was purified by reversed-phase chromatography (H$_2$O/CH$_3$CN with 0.1% formic acid, from 85:15 to 20:80). Dichloromethane and a saturated solution of NaHCO$_3$ were added to the residue after purification. The two phases were separated and the aqueous phase extracted twice with DCM. Then the fraction was collected and dried under reduced pressure, affording 150 mg of the desired product (Compound (6)) (yield: 73.5%) as a sticky oil.

$^1$H NMR (400 MHz, DMSO-d6) δ 11.66 (s, 1H), 7.88 (d, J=2.4 Hz, 1H), 7.80 (dd, J=8.8, 2.5 Hz, 1H), 7.38 (d, J=8.9 Hz, 1H), 7.31 (s, 1H), 5.38 (dt, J=6.2, 4.3 Hz, 1H), 4.90 (dd, J=12.9, 2.6 Hz, 1H), 4.67 (dd, J=12.9, 6.1 Hz, 1H), 4.37 (q, J=7.2 Hz, 2H), 4.20-3.96 (m, 6H), 2.75 (m, 6H), 2.62-2.51 (m, 8H), 1.82-1.52 (m, 8H), 1.46-1.29 (m, 3H), 0.94 (t, J=7.4 Hz, 6H).

EXAMPLE 15

(S)-(1-(4-(3-chloro-4-methoxybenzylamino)-5-(pyrimidin-2-ylmethylcarbamoyl) pyrimidin-2-yl)pyrrolidin-2-yl)methyl 6-(nitrooxy)hexyl Carbonate (Compound (13))

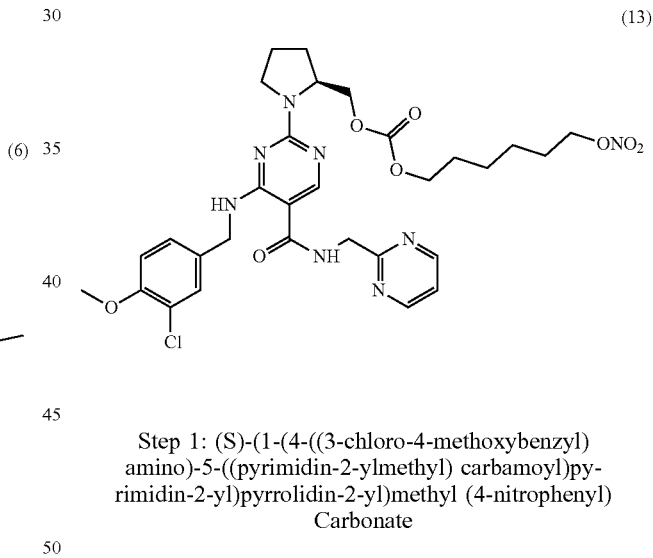

(13)

Step 1: (S)-(1-(4-((3-chloro-4-methoxybenzyl)amino)-5-((pyrimidin-2-ylmethyl) carbamoyl)pyrimidin-2-yl)pyrrolidin-2-yl)methyl (4-nitrophenyl) Carbonate To a solution of Avanafil (500 mg, 1.033 mmol) in dry DCM (10 ml), 4-Nitrophenyl chloroformate (416 mg, 2.066 mmol) and Pyridine (184 μL, 2.346 mmol) were added. The mixture was stirred for 2 h at room temperature then diluted with DCM and water. The two phases were separated and the aqueous layer extracted twice with DCM, giving 1.02 g of the desired product ((S)-(1-(4-((3-chloro-4-methoxybenzyl)amino)-5-((pyrimidin-2-ylmethyl) carbamoyl)pyrimidin-2-yl)pyrrolidin-2-yl)methyl (4-nitrophenyl) carbonate).

Step 2: (S)-(1-(4-(3-chloro-4-methoxybenzylamino)-5-(pyrimidin-2-ylmethyl carbamoyl)pyrimidin-2-yl) pyrrolidin-2-yl)methyl 6-(nitrooxy)hexyl Carbonate To a solution of (S)-(1-(4-((3-chloro-4-methoxybenzyl) amino)-5-((pyrimidin-2-ylmethyl)carbamoyl)pyrimidin-2- yl)pyrrolidin-2-yl)methyl (4-nitrophenyl) carbonate (1.02 g, 1.57 mmol) in dry DCM (20 ml), DMAP (211 mg, 1.73 mmol) and 6-hydroxyhexyl nitrate (282 mg, 1.73 mmol) were added. The mixture was stirred overnight at room temperature, then it was diluted with DCM and water. The two phases were separated and the aqueous phase extracted twice with DCM. The combined organic phases were dried over MgSO$_4$ and concentrated under reduced pressure. The residue was purified by flash chromatography (DCM/iPrOH from 100:0 to 90:10). Then the fraction was collected and dried under reduced pressure, affording 405 mg of title compound (Compound (13)) (yield: 38%) as a sticky oil.

$^1$H NMR (600 MHz, DMSO-d6) δ 9.17 (t, J=6.0 Hz, 1H), 8.79 (m, 1H), 8.75 (d, J=4.9 Hz, 2H), 8.55 (m, 1H), 7.45-7.15 (m, 3H), 7.04 (d, J=8.3 Hz, 1H), 4.61-4.43 (m, 6H), 4.29 (m, 3H), 4.05 (t, J=6.4 Hz, 2H), 3.81 (s, 3H), 3.56-3.42 (m, 2H), 2.05-1.80 (m, 4H), 1.60 (m, 4H), 1.32 (t, 4H).

EXAMPLE 16

(S)-2-(4-(3-(5-ethyl-4-oxo-7-propyl-4,5-dihydro-3H-pyrrolo[3,2-d]pyrimidin-2-yl)-4-propoxyphenylsulfonyl)piperazin-1-yl)ethyl 3-(2,3-bis(nitrooxy) propoxy)propanoate Dihydrochloride (Compound (1)-(2S) Dihydrochloride Salt)

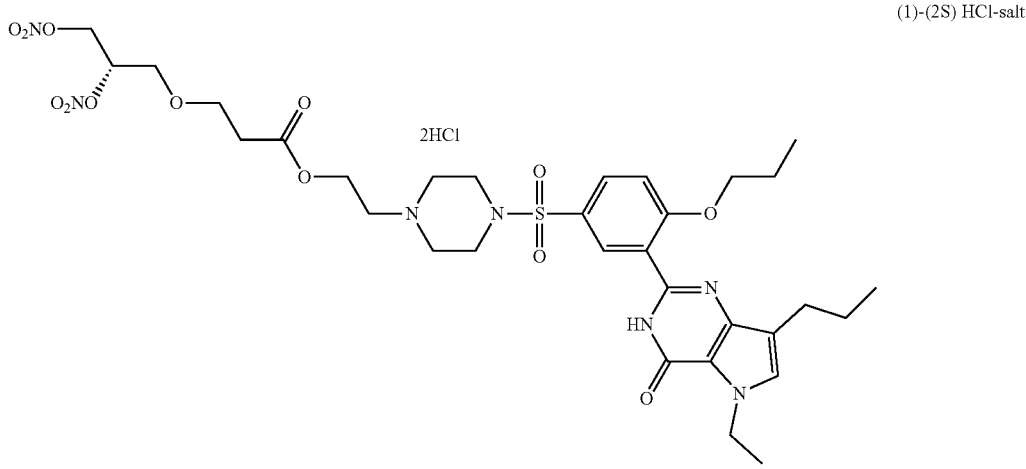

To a solution of Compound (1), obtained in Example 9 (72 mg, 0.094 mmol) in Methanol (1.0 ml), HCl 3M methanolic solution (63 uL, 0.188 mmol) was added. The mixture was stirred for 10 minutes at room temperature, then concentrated and the solid washed with Et$_2$O. The solid was filtered and dried under reduced pressure, giving 68 mg of the title compound (Compound (1)-(2S) dihydrochloride salt) (yield: 86%).

$^1$H NMR (600 MHz, DMSO-d6) δ 11.73 (s, 1H), 11.05 (s, 1H), 8.07-7.76 (m, 2H), 7.42 (d, J=8.7 Hz, 1H), 7.32 (s, 1H), 5.59-5.52 (m, 1H), 4.90 (dd, J=12.8, 2.8 Hz, 1H), 4.75 (dd, J=12.8, 6.5 Hz, 1H), 4.38 (q, J=7.1 Hz, 3H), 4.14 (t, J=6.3 Hz, 2H), 3.77-3.66 (m, 6H), 2.60-2.49 (m, 14H), 1.80-1.72 (m, 2H), 1.69-1.60 (m, 2H), 1.36 (t, J=7.2 Hz, 3H), 0.97 (t, J=7.4 Hz, 3H), 0.93 (t, J=7.3 Hz, 3H).

EXAMPLE 17

((S)-1-(4-(3-chloro-4-methoxybenzylamino)-5-(pyrimidin-2-ylmethylcarbamoyl) pyrimidin-2-yl)pyrrolidin-2-yl)methyl (S)-5,6-bis(nitrooxy)hexyl Carbonate (Compound (14)-(5S) Isomer)

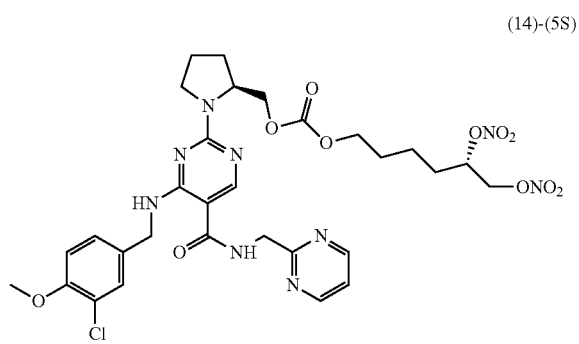

To a solution of (S)-(1-(4-((3-chloro-4-methoxybenzyl) amino)-5-((pyrimidin-2-ylmethyl)carbamoyl)pyrimidin-2-yl)pyrrolidin-2-yl)methyl (4-nitrophenyl) carbonate (prepared as described in Example 15, Step 1 (758 mg, 1.167 mmol) in dry DCM (10 ml), DMAP (157 mg, 1.284 mmol) and (2S)-6-hydroxyhexane-1,2-diyl dinitrate (288 mg, 1.284 mmol) were added.

The mixture was stirred overnight at room temperature and then diluted with DCM and water. The two phases were separated and the aqueous layer extracted twice with DCM. The combined organic phases were dried over MgSO$_4$ and concentrated under reduced pressure. The residue was purified by flash chromatography (DCM/iPrOH from 100:0 to 90:10) and then by reversed-phase chromatography (H$_2$O/CH$_3$CN, from 100:0 to 0:100), giving 334 mg of the desired product (Compound (14)-(5S) isomer) (yield: 39%) as a sticky solid.

$^1$H NMR (600 MHz, DMSO-d6) δ 9.17 (d, J=5.5 Hz, 1H), 8.79 (m, 1H), 8.75 (d, J=4.9 Hz, 2H), 8.55 (s, 1H), 7.44-7.16 (m, 3H), 7.04 (d, J=7.7 Hz, 1H), 5.41 (m, 1H), 4.92 (d, J=12.8 Hz, 1H), 4.69 (dd, J=12.7, 6.0 Hz, 1H), 4.64-4.42 (m, 4H), 4.39-4.14 (m, 3H), 4.06 (m, 2H), 3.81 (m, 3H), 3.49 (m, 2H), 1.92 (m, 4H), 1.66 (m, 4H), 1.42 (m, 2H).

EXAMPLE 18

(S)-(1-(4-(3-chloro-4-methoxybenzylamino)-5-(pyrimidin-2-ylmethylcarbamoyl) pyrimidin-2-yl)pyrrolidin-2-yl)methyl 6-(nitrooxy) hexylcarbonate 2-hydroxypropane-1,2,3-tricarboxylate (Compound (13) Citrate Salt)

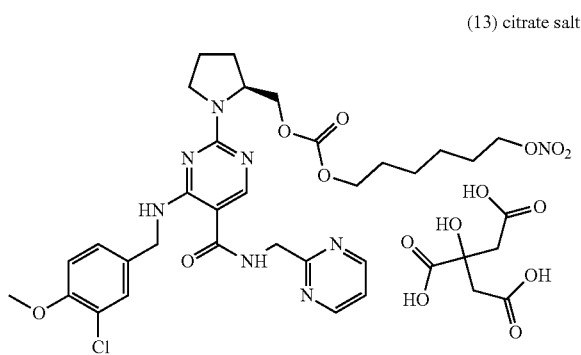

(13) citrate salt

To a solution of (S)-(1-(4-(3-chloro-4-methoxybenzylamino)-5-(pyrimidin-2-ylmethylcarbamoyl)pyrimidin-2-yl)pyrrolidin-2-yl)methyl 6-(nitrooxy)hexyl carbonate (Compound (13), prepared as described in Example 15 (218 mg, 0.324 mmol) in Methanol (1.0 ml), citric acid monohydrate (68 mg, 0.324 mmol) was added. The mixture was stirred for 10 minutes at room temperature, then concentrated and the solid washed with MTBE. The solid was filtered and dried under reduced pressure, giving 265 mg of the desired product (Compound (13) citrate salt) (crude yield: 94.5%).

$^1$H NMR (400 MHz, DMSO-d6) δ 9.19 (t, J=5.8 Hz, 1H), 8.80 (m, 1H), 8.75 (d, J=4.9 Hz, 2H), 8.54 (m, 1H), 7.38 (t, J=4.9 Hz, 1H), 7.35-7.15 (m, 2H), 7.06 (s, 1H), 4.64-4.43 (m, 6H), 4.29 (m, 3H), 4.05 (t, J=6.5 Hz, 2H), 3.81 (s, 3H), 3.49 (t, J=7.1 Hz, 2H), 2.76 (d, J=15.4 Hz, 2H), 2.65 (d, J=15.4 Hz, 2H), 2.06-1.81 (m, 4H), 1.61 (m, 4H), 1.33 (m, 4H).

EXAMPLE 19

2-{4-[4-ethoxy-3-(1-methyl-7-oxo-3-propyl-6,7-dihydro-1H-pyrazolo[4,3-d]pyrimidin-5-yl)benzene-1-sulfonyl]piperazin-1-yl}ethyl 6-(nitrooxy)hexanoate (Compound (8b))

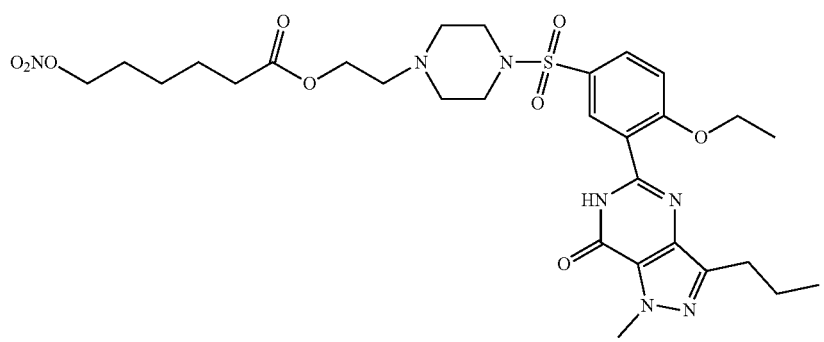

(8b)

To a solution of Lodenafil (400 mg, 0.793 mmol) in dry DCM (5 ml), DMAP (97 mg, 0.793 mmol), DCC (196 mg, 0.951 mmol) and 6-(nitrooxy)hexanoic acid (168 mg, 0.951 mmol) were added.

The mixture was stirred overnight at room temperature then it was diluted with DCM and water. The two phases were separated and the aqueous phase extracted twice with DCM. The combined organic phases were dried over MgSO$_4$ and concentrated under reduced pressure. The residue was purified by reversed-phase chromatography (H$_2$O/CH$_3$CN with 0.01% formic acid, from 90:10 to 20:80). Dichloromethane and a saturated solution of NaHCO$_3$ were added to the residue after purification. The two phases were separated and the aqueous phase extracted twice with DCM. The combined organic phases were dried over MgSO$_4$ and concentrated under reduced pressure, affording 150 mg of the desired product (Compound (8b)) (yield: 69.0%).

$^1$H NMR (400 MHz, DMSO-d6) δ 12.17 (s, 1H), 7.81 (m, 2H), 7.36 (d, J=8.7 Hz, 1H), 4.43 (t, J=6.6 Hz, 2H), 4.19 (q, J=6.9 Hz, 2H), 4.14 (s, 3H), 4.03 (t, J=5.7 Hz, 2H), 2.86 (bs, 4H), 2.75 (t, J=7.5 Hz, 2H), 2.58-2.37 (m, 5H), 2.23 (t, J=7.3 Hz, 2H), 1.72 (dd, J=14.9, 7.4 Hz, 2H), 1.63-1.53 (m, 2H), 1.53-1.40 (m, 2H), 1.35-1.20 (m, 6H), 0.92 (t, J=7.4 Hz, 3H).

EXAMPLE 20

(S)-2-(4-((4-ethoxy-3-(1-methyl-7-oxo-3-propyl-6,7-dihydro-1H-pyrazolo[4,3-d]pyrimidin-5-yl)phenyl)sulfonyl)piperazin-1-yl)ethyl (S)-5,6-bis(nitrooxy)hexanoate (Compound (7b)-(5S)) Isomer)

(7b)-(5S)

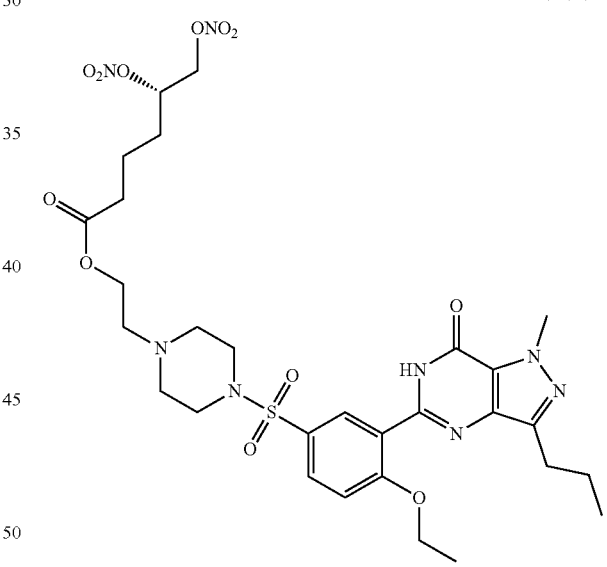

To a solution of Lodenafil (400 mg, 0.793 mmol) in dry DCM (5 ml), DMAP (97 mg, 0.793 mmol), DCC (196 mg, 0.951 mmol) and (5S)-5,6-bis(nitrooxy)hexanoic acid (226 mg, 0.951 mmol) were added. The mixture was stirred overnight at room temperature, then it was diluted with DCM and water. The two phases were separated and the aqueous phase extracted twice with DCM. The combined organic phases were dried over $MgSO_4$ and concentrated under reduced pressure. The residue was purified by reversed-phase chromatography ($H_2O/CH_3CN$ with 0.01% Formic acid, from 85:15 to 10:90). Dichloromethane and a saturated solution of $NaHCO_3$ were added to the residue after purification. The two phases were separated and the aqueous phase extracted twice with DCM. The combined organic phases were dried over $MgSO_4$ and concentrated under reduced pressure, affording 150 mg of the desired product (Compound (7b)-(5S)) isomer) (yield: 78.0%).

$^1$H NMR (400 MHz, DMSO-d6) δ 12.17 (s, 1H), δ 7.85-7.76 (m, 2H), 7.36 (d, J=8.7 Hz, 1H), 5.36 (m, J=6.0, 3.4 Hz, 1H), 4.87 (dd, J=12.9, 2.6 Hz, 1H), 4.65 (dd, J=12.9, 5.9 Hz, 1H), 4.26-4.12 (m, 5H), 4.02 (t, J=5.7 Hz, 2H), 2.87 (bs, 4H), 2.75 (t, J=7.6 Hz, 2H), 2.59-2.41 (m, 3H), 2.30 (t, J=7.1 Hz, 2H), 2.08 (s, 2H), 1.78-1.33 (m, 7H), 1.32 (t, J=6.9 Hz, 3H), 0.92 (t, J=7.4H).

EXAMPLE 21—(COMPARATIVE EXAMPLE)—PDE5 INHIBITOR NITRATE ESTER 2-(4-(3-(5-ethyl-4-oxo-7-propyl-4,5-dihydro-3H-pyrrolo[3,2-d]pyrimidin-2-yl)-4-propoxyphenylsulfonyl)piperazin-1-yl)ethyl Nitrate

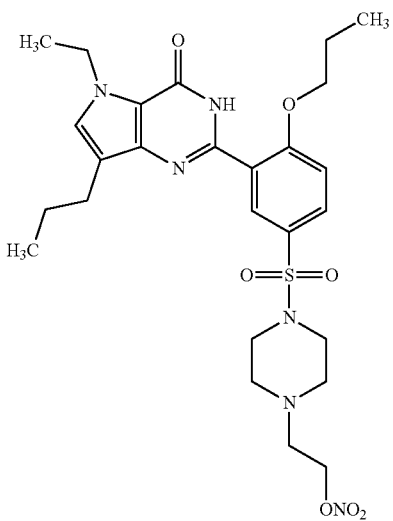

The nitrate ester of mirodenafil was prepared from mirodenafil following procedure described in WO 2017/085056 (Example 29): the hydroxyl group of mirodenafil was first transformed into the corresponding bromide with known method ($PPh_3$/NBS) and then nitrated with Silver nitrate in acetonitrile.

$^1$H NMR (600 MHz, CHLOROFORM-d) δ ppm 10.71 (br s, 1H) 7.80 (dd, J=8.65, 2.49 Hz, 1H) 7.15 (d, J=8.80 Hz, 1H) 5.30 (s, 1H) 4.41-4.55 (m, 5H) 4.25 (t, J=6.45 Hz, 3H) 3.11 (br s, 5H) 2.72 (t, J=7.48 Hz, 4H) 2.53-2.69 (m, 5H) 2.00-2.09 (m, 3H) 1.74 (sxt, J=7.39 Hz, 4H) 1.48 (t, J=7.19 Hz, 5H) 1.20 (t, J=7.33 Hz, 5H) 1.00 (t, J=7.33 Hz, 5H).

EXAMPLE 22

Intraocular Pressure (IOP) Lowering Effect in Laser-Induced Ocular Hypertensive Non-Human Primates In this study the efficacy in lowering intraocular pressure of a compound of formula (Ia), compound (1)-(2S)-citrate salt (disclosed in Example 9), the NO-donor 3-[(2S)-2,3-bis(nitrooxy)propoxy]propanoic acid ((IIIg)-OH) and the reference PDE5 inhibitor (mirodenafil) were evaluated in laser-induced ocular hypertensive non-human primates.

Experimental Procedure

Compound (1)-(2S)-citrate salt (0.48 µmoles/eye equal to 1.59% w/v, 30 µL), Mirodenafil (0.48 µmoles/eye equal to 1% w/v, 30 µL), NO-donor ((IIIg)-OH=3-[(2S)-2,3-bis(nitrooxy)propoxy]propanoic acid; 1.17 µmoles/eye equal to 1% w/v, 30 µL) or vehicle (phosphate buffer pH 6, cremophor EL 5% w/v, DMSO 0.3% w/v, benzalkonium chloride 0.02% w/v) were administered to laser induced ocular hypertensive non-human primates in a masked fashion. The contralateral eye was not treated.

Intraocular pressure was measured at selected time points using a pneumatonometer (Model 30™ Reichert, Depew, NY, USA) prior to (basal) and at selected time point following ocular dosing. One topical drop of proparacaine HCl 0.13% was applied to the eye prior to each intraocular pressure measurement.

Results

Data are reported as mean±SEM of n=13. Efficacy (E) as IOP change was calculated versus basal and vehicle values using the following equation: $(IOP_{drug}-IOP_{basal\ drug})-(IOP_{veh}-IOP_{basal\ veh})$. Values reported refer to maximum IOP change ($E_{max}$) and the IOP lowering effect detected at 300 min post-dose ($E_{300min}$).

The results demonstrated that the nitric oxide releasing phosphodiesterase type 5 inhibitor of the invention (compound (1)-(2S)-citrate salt) showed higher maximum intraocular-pressure lowering effect ($E_{max}$) and a longer duration with respect to the single administrations of the compound (IIIg)-OH (NO-donor) and mirodenafil (reference PDE5 inhibitor). Of note, the NO-donor (IIIg-OH) was administered at doses 2.4 times higher than the compound of the invention ((1)-(2S) citrate salt).

TABLE 1

IOP lowering activity following topical dosing in laser-induced ocular hypertensive non-human primates

| Compound | Amount administered (µmoles/eye) | IOP change (mmHg) | |
|---|---|---|---|
| | | $E_{max}$/time post-dosing | $E_{300\ min}$ |
| (1)-(2S)-citrate salt | 0.48 | −7.0 ± 0.9 (60 min) | −5.3 ± 1.9 |
| Mirodenafil | 0.48 | −5.0 ± 2.1 (180 min) | −3.4 ± 2.3 |
| (IIIg)-OH | 1.17 | −6.0 ± 2.7 (180 min) | −2.8 ± 2.8 |

EXAMPLE 23

Intraocular Pressure (IOP) Lowering Effect in Laser-Induced Ocular Hypertensive Non-Human Primates In independent experiments the efficacies in lowering intraocular pressure of a compound of formula (II), compound (9)-citrate salt (disclosed in Example 5), and the NO-donor 6-(nitrooxy)hexanoic acid ((IIIa)-OH) were evaluated in laser-induced ocular hypertensive non-human primates.

Experimental Procedure

Compound (9)-citrate salt (0.79 μmoles/eye equal to 2.2% w/v, 30 μL) or the NO-donor ((IIIa)-OH=6-(nitrooxy) hexanoic acid; (0.79 μmoles/eye equal to 0.47% w/v, 30 μL) or vehicle (phosphate buffer pH 6, cremophor EL 5% w/v, DMSO 0.3% w/v, benzalkonium chloride 0.02% w/v) were administered to laser induced ocular hypertensive non-human primates. The contralateral eye was not treated.

Intraocular pressure was measured using a pneumatonometer (Model 30™ Reichert, Depew, NY, USA) prior to (basal) and at selected time point following ocular dosing. One topical drop of proparacaine HCl 0.13% was applied to the eye prior to each intraocular pressure measurement.

Results

Efficacy (E) as TOP change was calculated versus basal and vehicle values using the following equation: $(IOP_{drug} - IOP_{basal\ drug}) - (IOP_{veh} - IOP_{basal\ veh})$ where TOP values are taken at 30, 60, 180, 300 and 480 minutes post-dosing.

The results reported in Table 2 demonstrated that the nitric oxide releasing phosphodiesterase type 5 inhibitor of the invention (compound (9)-citrate salt) showed higher maximum intraocular-pressure lowering efficacy (compare $E_{max}$ of compound (IIIa)-OH of −5.2±1.0 mmHg at 60 min to the $E_{max}$ of compound (9)-citrate salt of −6.0±2.1 at 480 min) and a longer duration (compare $E_{480}$ of compound (IIIa)-OH of −2.7±1.5 mmHg to that of compound (9)-citrate salt of −6.0±2.1 mmHg at the same time-point).

TABLE 2

IOP lowering activity following topical dosing in laser-induced ocular hypertensive non-human primates

| Compound | Amount administered (μmoles/eye) | IOP change (mmHg) $E_{max}$/time post dosing | $E_{480}$ |
|---|---|---|---|
| (9)-citrate salt | 0.79 | −6.0 ± 2.1 (480 min) | −6.0 ± 2.1 |
| (IIIa)-OH | 0.79 | −5.2 ± 1.0 (60 min) | −2.7 ± 1.5 |

Data reported are mean±SEM of three independent experiments each performed on n=8 eye for compound 6-(nitrooxy)hexanoic acid ((IIIa)-OH) and mean±SEM of one experiment performed on n=8 eye for compound (9)-citrate salt.

EXAMPLE 24

Intraocular Pressure (IOP) Lowering Effects in Ocular Normotensive New Zealand White Rabbits In this study the efficacy in lowering intraocular pressure of the NO-donor that is compound 3-[(2S)-2,3-bis(nitrooxy) propoxylpropanoic acid ((IIIg)-OH) (disclosed in Example 4) and the reference PDE5 inhibitor (mirodenafil) were assessed in ocular normotensive New Zealand white rabbits.

Experimental Procedure

Male New Zealand white (NZW) rabbits were topically administered (50 μL) with vehicle (phosphate buffer pH 6.0, cremophor EL 5% w/v, DMSO 0.3% w/v, benzalkonium chloride 0.02% w/v), 0.5 μmoles/eye equal to 0.63% w/v mirodenafil (50 μL dose), 0.5 μmoles/eye equal to 0.26% w/v compound (IIIg-OH) (50 μL dose) alone or concomitantly with 0.5 μmoles/eye of mirodenafil (50 μL dose).

Intraocular pressure was determined using a pneumatonometer (Model 30™ Reichert, Depew, NY, USA) prior to (basal) and at selected time point following ocular dosing. One topical drop of NOVESINA 0.4% (purchased from Thea Pharma) was applied to the eye prior to each intraocular pressure measurement.

Results Data are expressed as mean±SEM of n=6-9. Efficacy (E) as intraocular pressure (TOP) change was calculated versus basal and vehicle values using the following equation:

$$(IOP_{drug} - IOP_{basal\ drug}) - (IOP_{veh} - IOP_{basal\ veh})$$

The IOP values are taken at maximal effect and at 300 min post-dosing.

The results reported in Table 3 demonstrated that the combined instillation of mirodenafil (reference PDE5 inhibitor) with compound (3-[(2S)-2,3-bis(nitrooxy)propoxy]propanoic acid ((IIIg)-OH) did not show any improvement of the intraocular pressure lowering effect compared with single instillation of each compound; indeed the efficacy ($E_{max}$) of Mirodenafil is comparable to the efficacy of the combined instillation of mirodenafil and compound (IIIg)-OH.

TABLE 3

IOP lowering activity following topical dosing in ocular normotensive New Zealand white rabbits

| Compound | Amount administered (μmoles/eye) | IOP change (mmHg) $E_{max}$/time post-dosing | $E_{300\ min}$ |
|---|---|---|---|
| Mirodenafil | 0.5 | −3.68 ± 0.89 120 min | −1.46 ± 0.79 |
| (IIIg)-OH | 0.5 | −2.88 ± 0.36 30 min | −0.08 ± 0.23 |
| Mirodenafil + (IIIg)-OH (coadministration) | 0.5 each compound | −3.20 ± 0.46 30 min | −0.19 ± 0.27 |

EXAMPLE 25

Intraocular Pressure (IOP) Lowering Effects in Ocular Normotensive New Zealand White Rabbits In this study the efficacies in lowering intraocular pressure of the compound of the invention (1)-(2S)-citrate salt (disclosed in Example 9), that is a NO-releasing derivative of Mirodenafil, and of Mirodenafil nitrate ester in which the nitrooxy group ($ONO_2$) is directly linked to the hydroxyl group of the Mirodenafil molecule (PDE5-nitrate ester disclosed in the comparative example 21) were assessed in ocular normotensive New Zealand white rabbits.

Experimental Procedure

Male New Zealand white (NZW) rabbits were topically administered (50 μL) with vehicle (phosphate buffer pH 6.0, cremophor EL 5% w/v, DMSO 0.3% w/v, benzalkonium chloride 0.02% w/v), 0.5 µmoles/eye equal to 1% w/v (1)-(2S)-citrate salt (504 dose), 0.5 µmoles/eye equal to 0.6% w/v the PDE5 nitrate ester (504 dose).

Intraocular pressure was determined using a pneumatonometer (Model 30™ Reichert, Depew, NY, USA) prior to (basal) and at selected time point following ocular dosing. One topical drop of NOVESINA 0.4% (purchased from Thea Pharma) was applied to the eye prior to each intraocular pressure measurement.

Results

Data are expressed as mean±SEM of n=6-9. Efficacy (E) as intraocular pressure (TOP) change was calculated versus basal and vehicle values as follow:

$$(IOP_{drug} - IOP_{basal\ drug}) - (IOP_{veh} - IOP_{basal\ veh})$$

The IOP values are taken at min at 30, 60 and 180 minutes post-dosing.

The results reported in Table 4 demonstrated that the nitric oxide releasing phosphodiesterase type 5 inhibitor of the invention (compound (1)-(2S)-citrate salt) showed higher intraocular pressure-lowering efficacy (compare the $E_{max}$ of compound (1)-(2S)-citrate salt to the corresponding $E_{max}$ of PDE5 nitrate ester) and a longer duration (compare IOP change at 180 min of compound (1)-(2S)-citrate salt to that of PDE5 nitrate ester) with respect to the correspondent PDE5 nitrate ester.

TABLE 4

IOP lowering activity following topical dosing in ocular normotensive New Zealand white rabbits

| | IOP change (mmHg) | |
|---|---|---|
| Compound | $E_{max}$/time post dosing | $E_{180\ min}$ |
| (1)-(2S)-citrate salt | −3.8 ± 0.5 (60 min) | −1.8 ± 0.8 |
| PDE5 nitrate ester | −2.6 ± 0.5 (60 min) | 0.3 ± 0.8 |

EXAMPLE 26

Intraocular Pressure (IOP) Lowering Effect in Laser-Induced Ocular Hypertensive Non-Human Primates In this experiment the efficacy in lowering intraocular pressure of a compound of formula (II), compound (9)-fumarate (disclosed in Example 29), was evaluated in laser-induced ocular hypertensive non-human primates.

Experimental Procedure

Compound (9)-fumarate (2.0% w/v, 30 µL) or vehicle (phosphate buffer pH 6, cremophor EL 5% w/v, DMSO 0.3% w/v, benzalkonium chloride 0.02% w/v) were administered to laser induced ocular hypertensive non-human primates. The contralateral eye was not treated.

Intraocular pressure was measured using a pneumatonometer (Model 30™ Reichert, Depew, NY, USA) prior to (basal) and at selected time point following ocular dosing. One topical drop of proparacaine HCl 0.13% was applied to the eye prior to each intraocular pressure measurement.

Results

Efficacy (E) as TOP change was calculated versus basal and vehicle values using the following equation: $(IOP_{drug} - IOP_{basal\ drug}) - (IOP_{veh} - IOP_{basal\ veh})$ where IOP values are taken at 30, 60, 300, 480 and 1440 minutes post-dosing.

The results reported in Table 5 demonstrated that compound (9)-fumarate salt showed maximum intraocular pressure-lowering efficacy, $E_{max}$ of −4.1±2.7 mmHg, at 300 min. Moreover, the IOP-lowering effect of compound (9)-fumarate salt persisted for 24 hours post-dosing time at which the IOP change was still −2.8±2.0 mmHg.

TABLE 5

IOP lowering activity following topical dosing in laser-induced ocular hypertensive non-human primates

| | IOP change (mmHg) | | | | |
|---|---|---|---|---|---|
| Compound | 30 min | 60 min | 300 min | 480 min | 1440 min |
| (9)-fumarate salt | −4.0 ± 1.3 | −3.5 ± 1.6 | −4.1 ± 2.7 | −3.0 ± 2.8 | −2.8 ± 2.0 |

Data reported are mean±SEM of one experiment performed on n=8 eye.

EXAMPLE 27

Intraocular Pressure (IOP) Lowering Effect in Laser-Induced Ocular Hypertensive Non-Human Primates In this study the efficacies in lowering intraocular pressure of compound (1)-(2S)-citrate salt (disclosed in Example 9), the NO-donor 3-[(2S)-2,3-bis(nitrooxy)propoxy]propanoic acid (compound (IIIg)-OH, disclosed in Example 4), the reference PDE5 inhibitor (Mirodenafil) and of the combined administration of Mirodenafil and the NO-donor 3-[(2S)-2,3-bis(nitrooxy)propoxy]propanoic acid were evaluated in laser-induced ocular hypertensive non-human primates.

Experimental Procedure

Compound (1)-(2S)-citrate salt (0.31 µmoles/eye equal to 1.0% w/v, 30 µL), Mirodenafil (0.31 µmoles/eye equal to 0.63% w/v, 30 µL), (IIIg)-OH (0.31 µmoles/eye equal to 0.26% % w/v, 30 µL), Mirodenafil concomitantly dosed with (IIIg)-OH or vehicle (phosphate buffer pH 6, cremophor EL 5% w/v, DMSO 0.3% w/v, benzalkonium chloride 0.02% w/v) were administered to laser induced ocular hypertensive non-human primates in a masked fashion. The contralateral eye was not treated.

Intraocular pressure was measured at selected time points using a pneumatonometer (Model 30™ Reichert, Depew, NY, USA) prior to (basal) and at selected time point following ocular dosing. One topical drop of proparacaine HCl 0.13% was applied to the eye prior to each intraocular pressure measurement.

Results

Data are reported as mean±SEM of n=13. Efficacy (E) as IOP change was calculated versus basal and vehicle values using the following equation: $(IOP_{drug} - IOP_{basal\ drug}) - (IOP_{veh} - IOP_{basal\ veh})$. Values reported refer to maximum TOP change ($E_{max}$) and the TOP lowering effect detected at 300 min post-dose ($E_{300min}$).

The results reported in Table 6 demonstrated that the nitric oxide releasing phosphodiesterase type 5 inhibitor of the invention (compound (1)-(2S)-citrate salt) showed higher intraocular-pressure lowering effect compared to equimolar doses of the NO-donor ((IIIg)-OH), Mirodenafil or the combination of Mirodenafil and the NO-donor at the majority of time-points of analyzed.

TABLE 6

IOP lowering activity following topical dosing in laser-induced ocular hypertensive non-human primates

| Compound | Dose (µmoles/eye) | IOP change (mmHg) | | | | |
|---|---|---|---|---|---|---|
| | | 30 min | 60 min | 180 min | 300 min | 1440 min |
| (1)-(2S)-citrate salt | 0.31 | −4.0 ± 0.9 | −5.3 ± 1.0 | −4.9 ± 1.5 | −4.4 ± 0.9 | −2.6 ± 1.3 |
| Mirodenafil | 0.31 | −2.2 ± 1.4 | −4.1 ± 1.5 | −3.8 ± 1.0 | −2.2 ± 1.1 | −1.0 ± 1.1 |
| (IIIg)-OH | 0.31 | −1.2 ± 0.7 | −3.9 ± 1.5 | −2.4 ± 1.4 | −3.9 ± 1.6 | −3.2 ± 1.6 |
| Mirodenafil + (IIIg)-OH | 0.31 (each compound) | −2.2 ± 0.9 | −3.0 ± 1.0 | −2.9 ± 1.2 | −2.1 ± 0.8 | −0.6 ± 0.9 |

EXAMPLE 28

(S)-2-(4-((4-ethoxy-3-(1-methyl-7-oxo-3-propyl-6,7-dihydro-1H-pyrazolo[4,3-d]pyrimidin-5-yl)phenyl)sulfonyl)piperazin-1-yl)ethyl-(S)-3-(2,3-bis(nitrooxy) propoxy)propanoate (Compound (15), (S) Isomer)

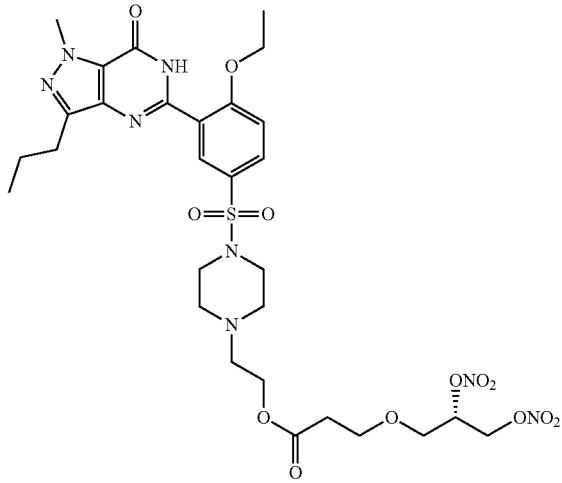

(15) (S)-isomer

To a solution of Lodenafil (400 mg, 0.794 mmol) and 4-nitrophenyl 3-[(2S)-2,3-bis(nitrooxy)propoxy]propanoate (see Example 4) (226 mg, 0.951 mmol) in dry DCM (5 ml), DMAP (97 mg, 0.794 mmol) was added.

The mixture was stirred over weekend at room temperature, then it was diluted with DCM and water. The two phases were separated and the aqueous phase extracted twice with DCM. The combined organic phases were dried over MgSO$_4$ and concentrated under reduced pressure. The residue was purified by reversed-phase chromatography (H$_2$O/CH$_3$CN with 0.01% FA, from 80:20 to 20:80). Dichloromethane and a saturated solution of NaHCO$_3$ were added to the residue after purification. The two phases were separated and the aqueous phase extracted twice with DCM. The combined organic phases were dried over MgSO$_4$ and concentrated under reduced pressure, affording 170 mg of the desired product ((Compound (15), (S) isomer) (yield: 30.0%).

$^1$H NMR (600 MHz, dmso) δ 12.19 (s, 1H), 7.83 (dt, J=8.7, 2.4 Hz, 2H), 7.38 (d, J=8.8 Hz, 1H), 5.53 (m, 1H), 4.88 (dd, J=12.8, 3.0 Hz, 1H), 4.72 (dd, J=12.8, 6.5 Hz, 1H), 4.21 (q, 2H), 4.16 (s, 3H), 4.06 (t, 2H), 3.77-3.59 (m, 4H), 2.89 (bs, 4H), 2.77 (t, 2H), 2.55 (m, 8H), 1.74 (dd, J=14.9, 7.4 Hz, 2H), 1.33 (t, J=6.9 Hz, 3H), 0.94 (t, J=7.4 Hz, 3H).

EXAMPLE 29

(S)-(1-(4-(3-chloro-4-methoxybenzylamino)-5-(pyrimidin-2-ylmethylcarbamoyl) pyrimidin-2-yl)pyrrolidin-2-yl)methyl 6-(nitrooxy)hexanoate Fumarate (Compound (9) Fumarate Salt)

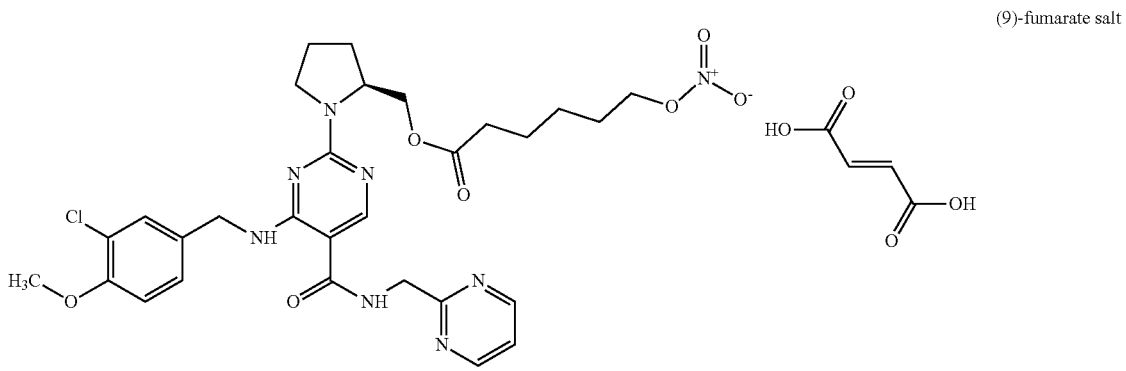

(9)-fumarate salt

To a solution of compound (9), prepared as described in Example 1, (100 mg, 0.155 mmol) in Methanol (1.5 ml), fumaric acid (18 mg, 0.155 mmol) was added. The mixture was stirred 10 minutes at room temperature, then concentrated and the solid washed with MTBE. The solid was filtered and dried under reduced pressure, yielding 103 mg of (S)-(1-(4-(3-chloro-4-methoxybenzylamino)-5-(pyrimidin-2-ylmethylcarbamoyl) pyrimidin-2-yl)pyrrolidin-2-yl)methyl 6-(nitrooxy)hexanoate fumarate (Compound (9) fumarate, yield: 87%).

$^1$H NMR (600 MHz, DMSO-d6) δ 13.13 (m, 2H), 9.17 (m, 1H), 8.76 (m, 3H), 8.54 (m, 1H), 7.38 (m, 1H), 7.24 (m, 2H), 7.04 (m, 1H), 6.63 (s, 2H), 4.52 (m, 5H), 4.20 (m, 2H), 3.81 (s, 3H), 3.52 (m, 2H), 3.32 (m, 2H), 2.31 (m, 2H), 1.92 (m, 4H), 1.64 (m, 2H), 1.50 (m, 2H), 1.32 (m, 2H).

EXAMPLE 30

(S)-(1-(4-(3-chloro-4-methoxybenzylamino)-5-(pyrimidin-2-ylmethylcarbamoyl) pyrimidin-2-yl)pyrrolidin-2-yl)methyl 6-(nitrooxy)hexanoate Maleate (Compound (9) Maleate Salt)

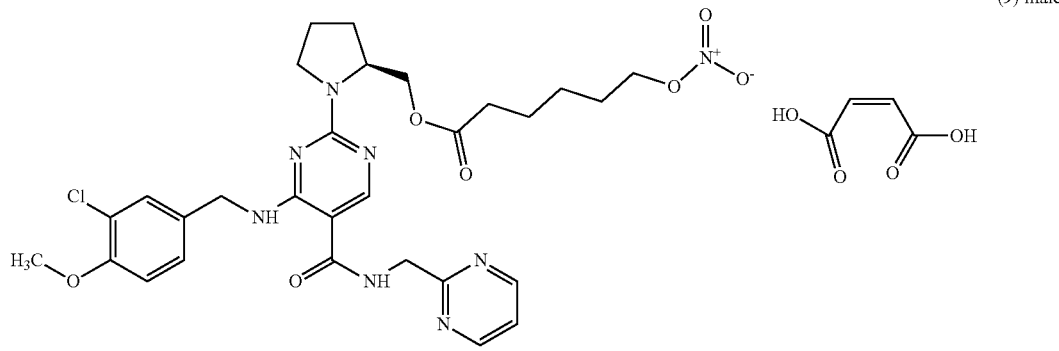

(9)-maleate salt

To a solution of compound (9), prepared as described in Example 1, (100 mg, 0.155 mmol) in Methanol (1.5 ml), maleic acid (18 mg, 0.155 mmol) was added. The mixture was stirred 10 minutes at room temperature, then concentrated and the solid washed with MTBE. The solid was filtered and dried under reduced pressure, giving 113 mg of (S)-(1-(4-(3-chloro-4-methoxybenzylamino)-5-(pyrimidin-2-ylmethylcarbamoyl) pyrimidin-2-yl)pyrrolidin-2-yl)methyl 6-(nitrooxy)hexanoate 2-maleate (Compound (9) maleate, yield: 96%).

$^1$H NMR (600 MHz, DMSO-d6) δ 12.35 (m, 3H), 9.18 (m, 1H), 8.77 (m, 3H), 8.54 (s, 1H), 7.38 (m, 2H), 7.22 (m, 1H), 7.04 (m, 1H), 4.55 (m, 6H), 4.20 (m, 3H), 3.98 (m, 1H), 3.80 (s, 3H), 3.49 (m, 2H), 2.75 (m, 2H), 2.65 (m, 2H), 2.31 (m, 2H), 1.92 (m, 4H), 1.56 (m, 4H), 1.32 (m, 2H).

EXAMPLE 31

Intraocular Pressure (IOP) Lowering Effects in Ocular Normotensive New Zealand White Rabbits In this study the efficacies in lowering intraocular pressure of the compound of the invention (12)-(2S)-citrate salt (disclosed in Example 8) was assessed in ocular normotensive New Zealand white rabbits.

Experimental Procedure

Male New Zealand white (NZW) rabbits were topically administered (50 μL) with vehicle (phosphate buffer pH 6.0, cremophor EL 5% w/v, DMSO 0.3% w/v, benzalkonium chloride 0.02% w/v), or (12)-(2S)-citrate salt at 1% concentration.

Intraocular pressure was determined using a pneumatonometer (Model 30™ Reichert, Depew, NY, USA) prior to (basal) and at selected time point following ocular dosing. One topical drop of NOVESINA 0.4% (purchased from Thea Pharma) was applied to the eye prior to each intraocular pressure measurement.

Results

Data are expressed as mean±SEM of n=9. Efficacy (E) as intraocular pressure (IOP) change was calculated versus basal and vehicle values as follow: $(IOP_{drug}-IOP_{basal\ drug})-(IOP_{veh}-IOP_{basal\ veh})$. The TOP values are taken at 30, 60 and 120 minutes post-dosing. The results reported in Table 7 demonstrated that the nitric oxide releasing phosphodiesterase type 5 inhibitor of the invention (compound (12)-(2S)-citrate salt) efficiently lowered TOP at several time points post dosing.

TABLE 7

IOP lowering activity following topical dosing in ocular normotensive New Zealand white rabbits

| Compound | IOP change (mmHg) | | |
|---|---|---|---|
| | 30 min | 60 min | 120 min |
| (12)-(2S)-citrate salt | −5.6 ± 0.9 | −3.9 ± 1.0 | −2.4 ± 0.8 |

The invention claimed is:

1. A compound of formula (II) or a stereoisomer or a pharmaceutically acceptable salt thereof:

(II)

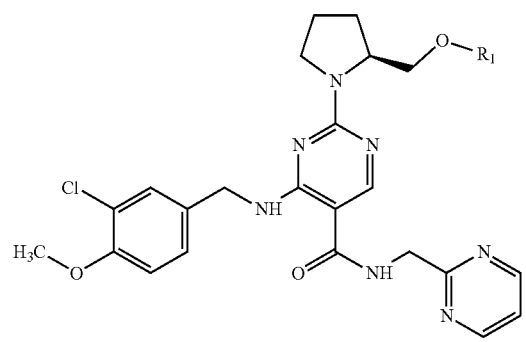

wherein:
R₁ is a residue of a nitric oxide releasing molecule having a formula:

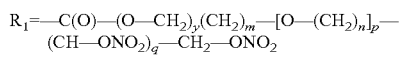

wherein:
y is 1 or 0;
p is 1 or 0;
q is 1 or 0;
m is an integer ranging from 1 to 10;
n is an integer ranging from 1 to 6.

2. A compound of formula (II) or a stereoisomer or a pharmaceutically acceptable salt thereof according to claim 1 wherein y is 0.

3. A compound of formula (II) or a stereoisomer or a pharmaceutically acceptable salt thereof according to claim 2 wherein R₁ is selected from the group consisting of:

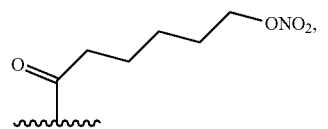 (IIIa)

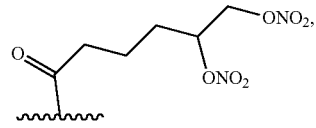 (IIIb)

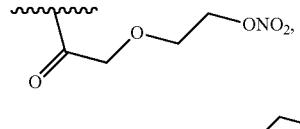 (IIIc)

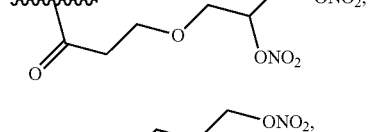 (IIId)

 (IIIe)

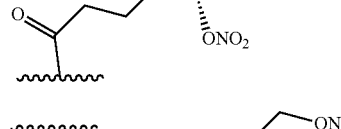 (IIIf)

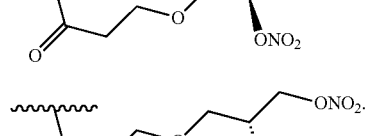 (IIIg) and

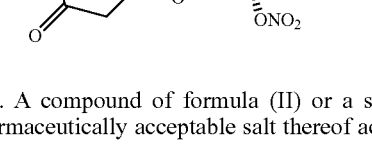 (IIIh)

4. A compound of formula (II) or a stereoisomer or a pharmaceutically acceptable salt thereof according to claim 1 where y is 1.

5. A compound of formula (II) or a stereoisomer or a pharmaceutically acceptable salt thereof according to claim 4 wherein R₁ is selected from the group consisting of:

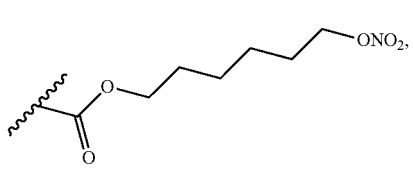 (IVa)

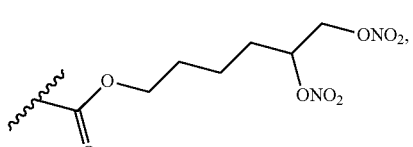 (IVb)

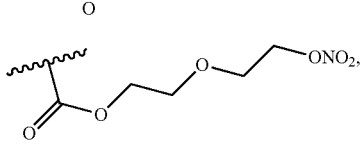 (IVc)

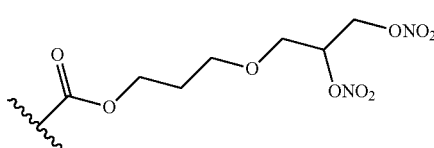 (IVd)

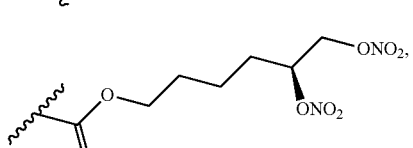 (IVe)

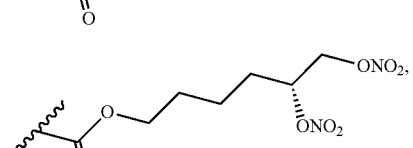 (IVf)

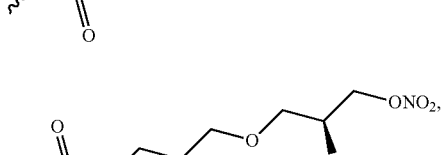 (IVg) and

 (IVh)

6. A compound of formula (II) or a stereoisomer or a pharmaceutically acceptable salt thereof according to claim 1 selected from the group consisting of:
- (S)-(1-(4-(3-chloro-4-methoxybenzylamino)-5-(pyrimidin-2-yl-methylcarbamoyl) pyrimidin-2-yl)pyrrolidin-2-yl)methyl 6-(nitrooxy)hexanoate (Compound (9));
- [(2S)-1-(4-{[(3-chloro-4-methoxyphenyl)methyl]amino}-5-{[(pyrimidin-2-yl) methyl]carbamoyl}pyrimidin-2-yl)pyrrolidin-2-yl]methyl 5,6-bis(nitrooxy)hexanoate (Compound (10));
- (S)-(1-(4-(3-chloro-4-methoxybenzylamino)-5-(pyrimidin-2-yl-methylcarbamoyl) pyrimidin-2-yl)pyrrolidin-2-yl)methyl 2-(2-(nitrooxy)ethoxy)acetate (Compound (11));
- [(2S)-1-(4-{[(3-chloro-4-methoxyphenyl)methyl]amino}-5-{[(pyrimidin-2-yl) methyl]carbamoyl}pyrimidin-2-yl)pyrrolidin-2-yl]methyl 3-[2,3-bis(nitrooxy)propoxy] propanoate (Compound (12));

(S)-(1-(4-(3-chloro-4-methoxybenzylamino)-5-(pyrimidin-2-yl-methylcarbamoyl) pyrimidin-2-yl)pyrrolidin-2-yl)methyl 6-(nitrooxy)hexylcarbonate (Compound (13)); and ((S)-1-(4-(3-chloro-4-methoxybenzylamino)-5-(pyrimidin-2-yl-methylcarbamoyl) pyrimidin-2-yl)pyrrolidin-2-yl)methyl 5,6-bis(nitrooxy)hexyl carbonate and (Compound (14)).

7. A compound of formula (I) according to claim 1 selected from the group consisting of:

[(2S)-1-(4-{[(3-chloro-4-m ethoxyphenyl)methyl]amino}-5-{[(pyrimidin-2-yl) methyl]carbamoyl}pyrimidin-2-yl)pyrrolidin-2-yl]methyl (5 S)-5,6-bis(nitrooxy) hexanoate (Compound (10)-(5S));

[(2S)-1-(4-{[(3-chloro-4-m ethoxyphenyl)methyl]amino}-5-{[(pyrimidin-2-yl) methyl]carbamoyl}pyrimidin-2-yl)pyrrolidin-2-yl]methyl 3-[(2 S)-2,3-bis(nitrooxy) propoxy] propanoate (Compound (12)-(2S));

(S)-(1-(4-(3-chloro-4-methoxybenzylamino)-5-(pyrimidin-2-yl-methylcarbamoyl) pyrimidin-2-yl)pyrrolidin-2-yl)methyl 6-(nitrooxy)hexanoate 2-hydroxypropane-1,2,3-tricarboxylate (Compound (9)-citrate salt);

((S)-1-(4-(3-chloro-4-methoxybenzylamino)-5-(pyrimidin-2-ylmethyl carbamoyl)pyrimidin-2-yl)pyrrolidin-2-yl)methyl (5 S)-5,6-bis(nitrooxy)hexanoate 2-hydroxypropane-1,2,3-tri carb oxyl ate (Compound (10)-(5S) citrate salt);

(S)-(1-(4-(3-chloro-4-methoxybenzylamino)-5-(pyrimidin-2-yl-methylcarbamoyl) pyrimidin-2-yl)pyrrolidin-2-yl)methyl 2-(2-(nitrooxy)ethoxy)acetate 2-hydroxy propane-1,2,3-tricarboxylate (Compound (11) citrate salt);

((S)-1-(4-(3-chloro-4-methoxybenzylamino)-5-(pyrimidin-2-yl-methylcarbamoyl) pyrimidin-2-yl)pyrrolidin-2-yl)methyl 3-((S)-2,3-bis(nitrooxy)propoxy)propanoate 2-hydroxypropane-1,2,3-tri carb oxyl ate (Compound (12)-(2S) citrate salt);

((S)-1-(4-(3-chloro-4-methoxybenzylamino)-5-(pyrimidin-2-yl-methylcarbamoyl) pyrimidin-2-yl)pyrrolidin-2-yl)methyl (S)-5,6-bis(nitrooxy)hexyl carbonate (Compound (14)-(5 S));

(S)-(1-(4-(3-chloro-4-methoxybenzylamino)-5-(pyrimidin-2-yl-methylcarbamoyl) pyrimidin-2-yl)pyrrolidin-2-yl)methyl 6-(nitrooxy)hexylcarbonate 2-hydroxypropane-1,2,3-tricarboxylate (Compound (13) citrate salt);

(S)-(1-(4-(3-chloro-4-methoxybenzylamino)-5-(pyrimidin-2-yl-methylcarbamoyl) pyrimidin-2-yl)pyrrolidin-2-yl)methyl 6-(nitrooxy)hexanoate fumarate (Compound (9) fumarate salt); and (S)-(1-(4-(3-chloro-4-methoxybenzylamino)-5-(pyrimidin-2-yl-methylcarbamoyl) pyrimidin-2-yl)pyrrolidin-2-yl)methyl 6-(nitrooxy)hexanoate maleate (Compound (9) maleate salt).

8. A method of treating ocular pressure resulting from a disease or condition, the method comprising administering a compound of or formula (II) or a stereoisomer or a pharmaceutically acceptable salt thereof according to claim 1 to a subject in need thereof to a subject in need thereof, wherein the disease or condition is selected from ocular hypertension, glaucoma, open-angle glaucoma, normal-tension glaucoma, pigmentary glaucoma, pseudoexfoliative glaucoma, and drug induced-glaucoma.

9. A method of treating retinopathies, the method comprising administering a compound of formula (II) or a stereoisomer or a pharmaceutically acceptable salt thereof according to claim 1 to a subject in need thereof.

10. An ophthalmic pharmaceutical composition comprising a compound of formula (II) or stereoisomer or a pharmaceutical salt thereof according to claim 1 and a pharmaceutically acceptable excipient or vehicle.

11. A composition comprising a compound of formula (II) according to claim 1 and at least another active agent selected from beta-adrenergic antagonists, prostaglandin analogues, adrenergic agonists, carbonic anhydrase inhibitors, cholinergic agonists, steroids, cholinesterase inhibitors, soluble guanylate cyclase activators, Rho-kinase inhibitors, and cinaciguat.

12. The composition according to claim 11 in the form of a kit including a dosage form comprising the compound of formula (II) and a dosage form comprising the other active agent.

13. The compound of claim 1, wherein m is from 1 to 6.

14. The compound of claim 1, wherein n is 1 or 2.

* * * * *